US012678438B2

(12) United States Patent
Asangani

(10) Patent No.: US 12,678,438 B2
(45) Date of Patent: Jul. 14, 2026

(54) TREATMENT OF CANCER WITH CDK INHIBITORS

(71) Applicant: THE TRUSTEES OF THE UNIVERSITY OF PENNSYLVANIA, Philadelphia, PA (US)

(72) Inventor: Irfan Asangani, Wallingford, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 1158 days.

(21) Appl. No.: 17/605,971

(22) PCT Filed: Apr. 24, 2020

(86) PCT No.: PCT/US2020/029883
§ 371 (c)(1),
(2) Date: Oct. 22, 2021

(87) PCT Pub. No.: WO2020/219926
PCT Pub. Date: Oct. 29, 2020

(65) Prior Publication Data
US 2022/0288067 A1    Sep. 15, 2022

Related U.S. Application Data

(60) Provisional application No. 62/838,271, filed on Apr. 24, 2019.

(51) Int. Cl.
| | |
|---|---|
| *A61K 31/506* | (2006.01) |
| *A61K 31/4164* | (2006.01) |
| *A61P 35/00* | (2006.01) |
| *C12Q 1/6886* | (2018.01) |

(52) U.S. Cl.
CPC ........ *A61K 31/506* (2013.01); *A61K 31/4164* (2013.01); *A61P 35/00* (2018.01); *C12Q 1/6886* (2013.01); *C12Q 2600/106* (2013.01); *C12Q 2600/118* (2013.01); *C12Q 2600/158* (2013.01)

(58) Field of Classification Search
CPC ... A61K 31/506; A61K 31/4164; A61P 35/00; C12Q 1/6886; C12Q 2600/106; C12Q 2600/118; C12Q 2600/158
USPC ........................................................ 514/275
See application file for complete search history.

(56) References Cited

FOREIGN PATENT DOCUMENTS

| WO | WO-2012/131594 | 10/2012 |
|---|---|---|
| WO | WO-2013/173517 | 11/2013 |
| WO | WO 2018/098361 A1 * | 5/2018 |
| WO | WO 2018/106729 A1 * | 6/2018 |

OTHER PUBLICATIONS

International Preliminary Report on Patentability dated Nov. 4, 2021 in respect of PCT Int'l Application No. PCT/US20/029882.

* cited by examiner

*Primary Examiner* — Kortney L. Klinkel
*Assistant Examiner* — Grace Ching Hsu
(74) *Attorney, Agent, or Firm* — Mark S. Cohen; PEARL COHEN ZEDEK LATZER BARATZ LLP

(57) ABSTRACT

The present invention relates to methods of treating cancer by administration of a cyclin dependent kinase (CDK) inhibitor to a subject.

7 Claims, 55 Drawing Sheets
Specification includes a Sequence Listing.

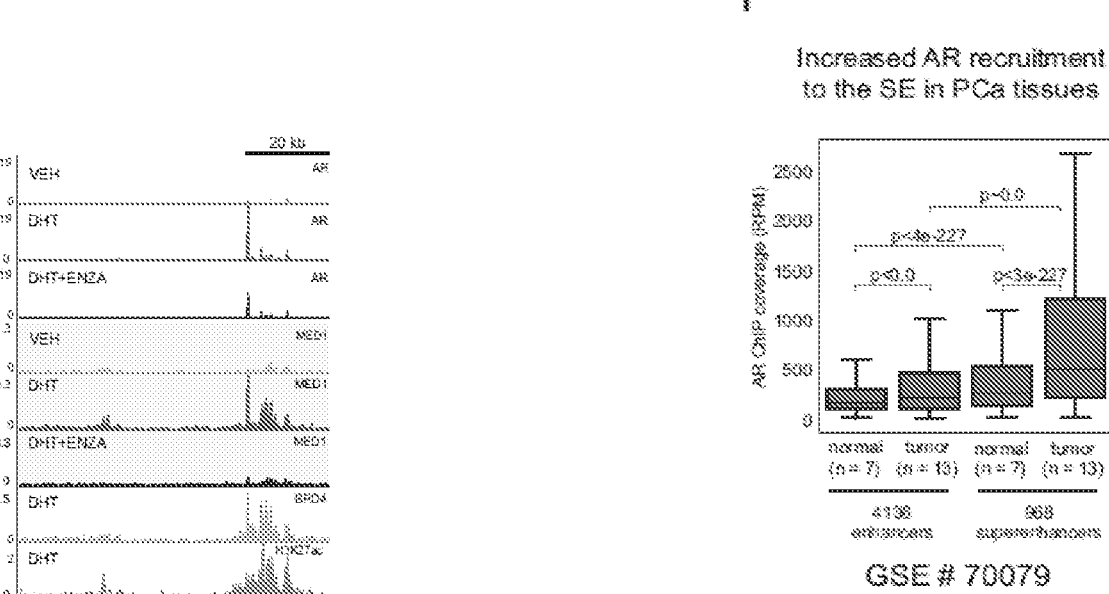
Figure 1E
Figure 1F
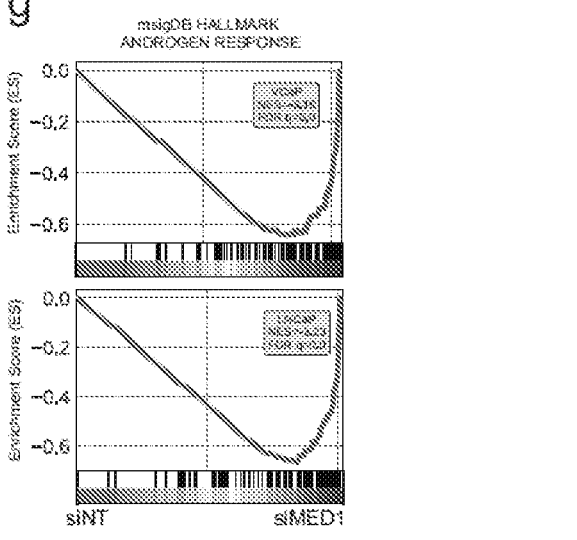
Figure 1G
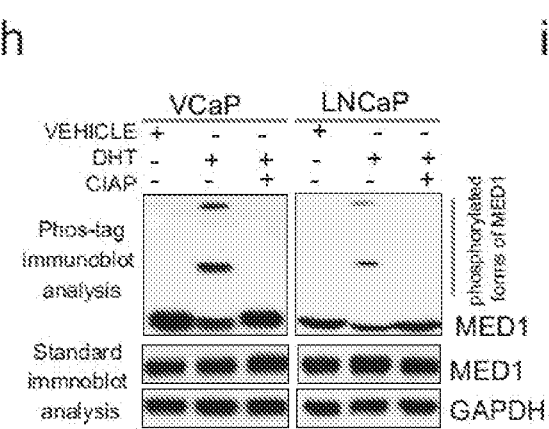
Figure 1H

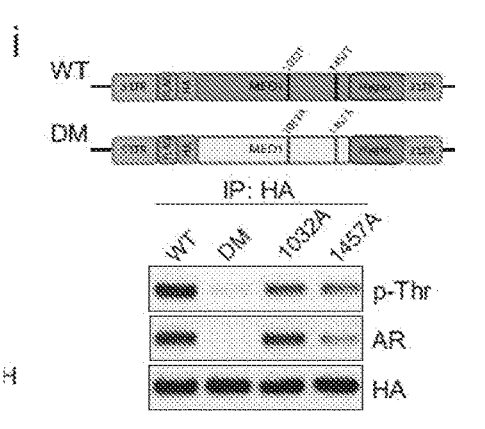
Figure 1I
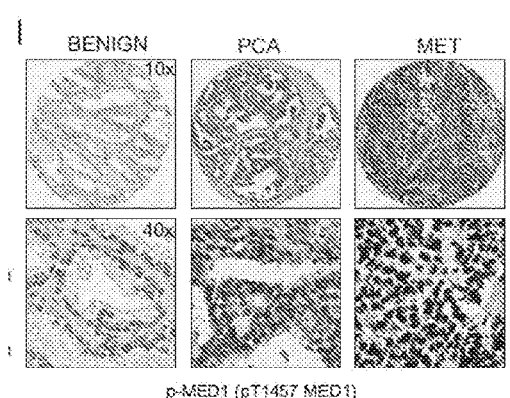
Figure 1J
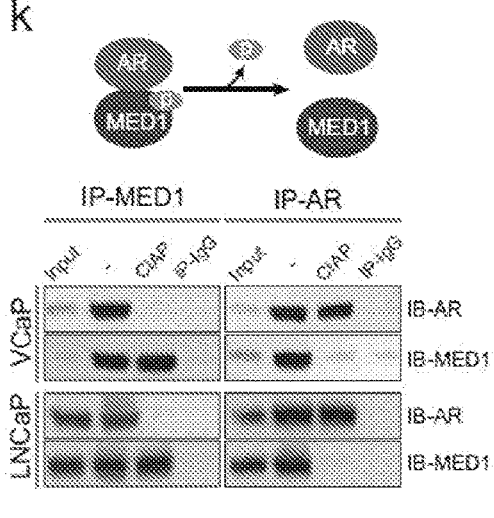
Figure 1K
Figure 1L
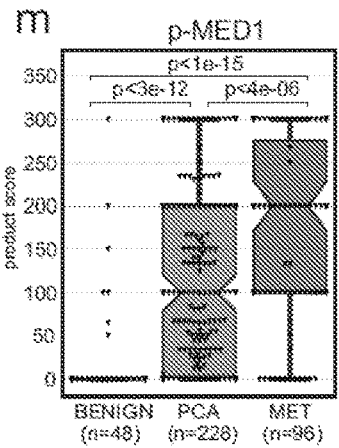
Figure 1M

Figure 2E                                    Figure 2F

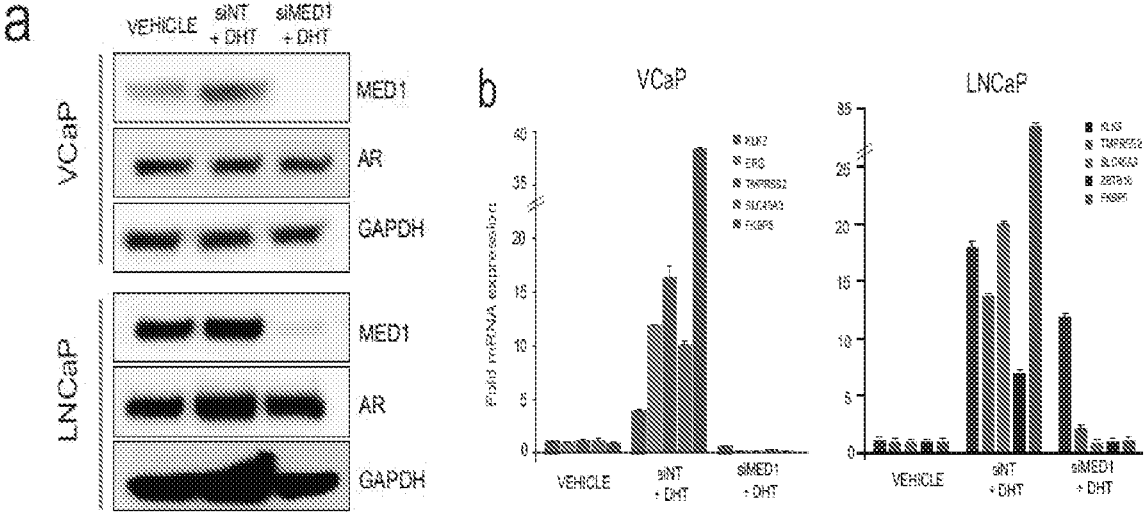
Figure 3A                    Figure 3B
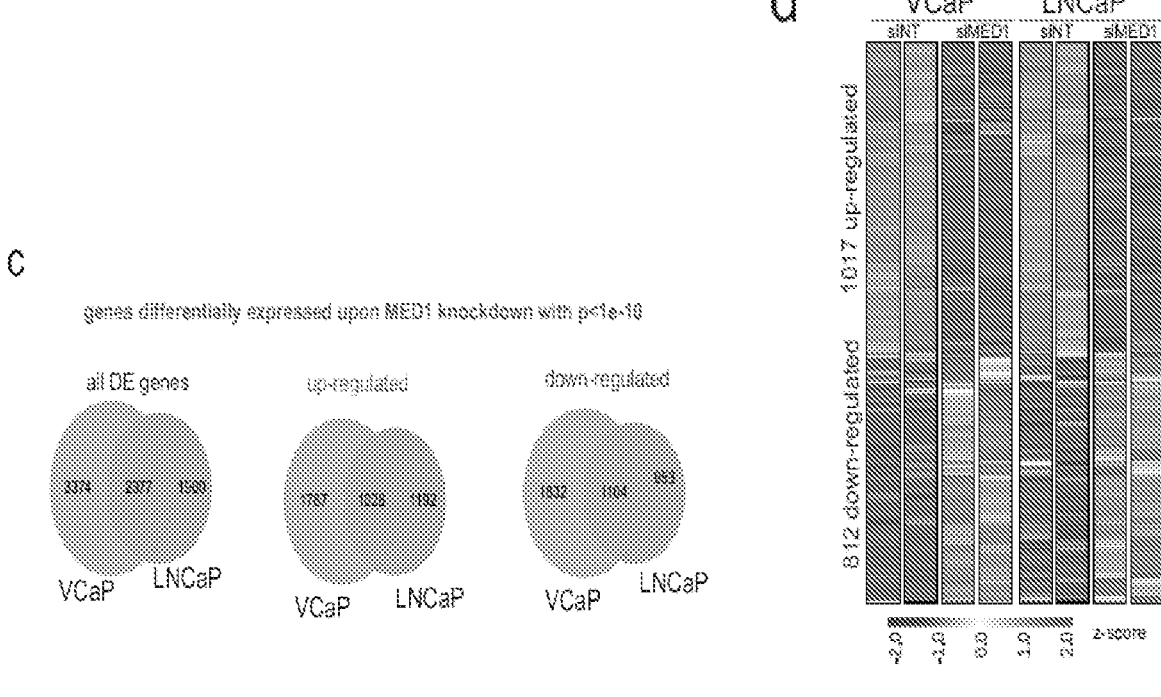
Figure 3C                    Figure 3D

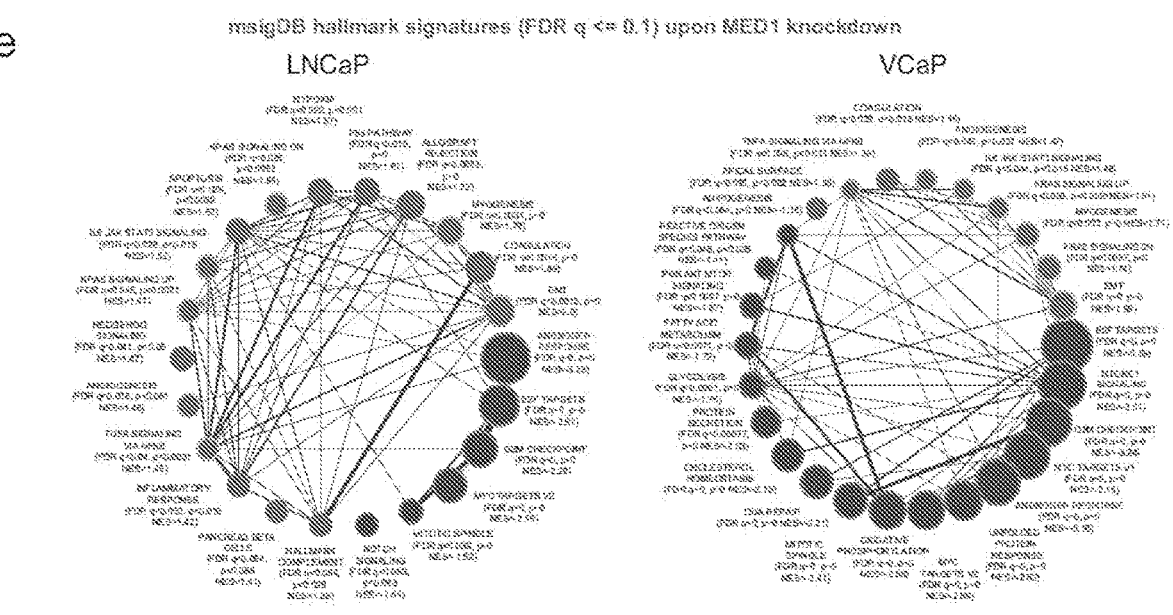
Figure 3E
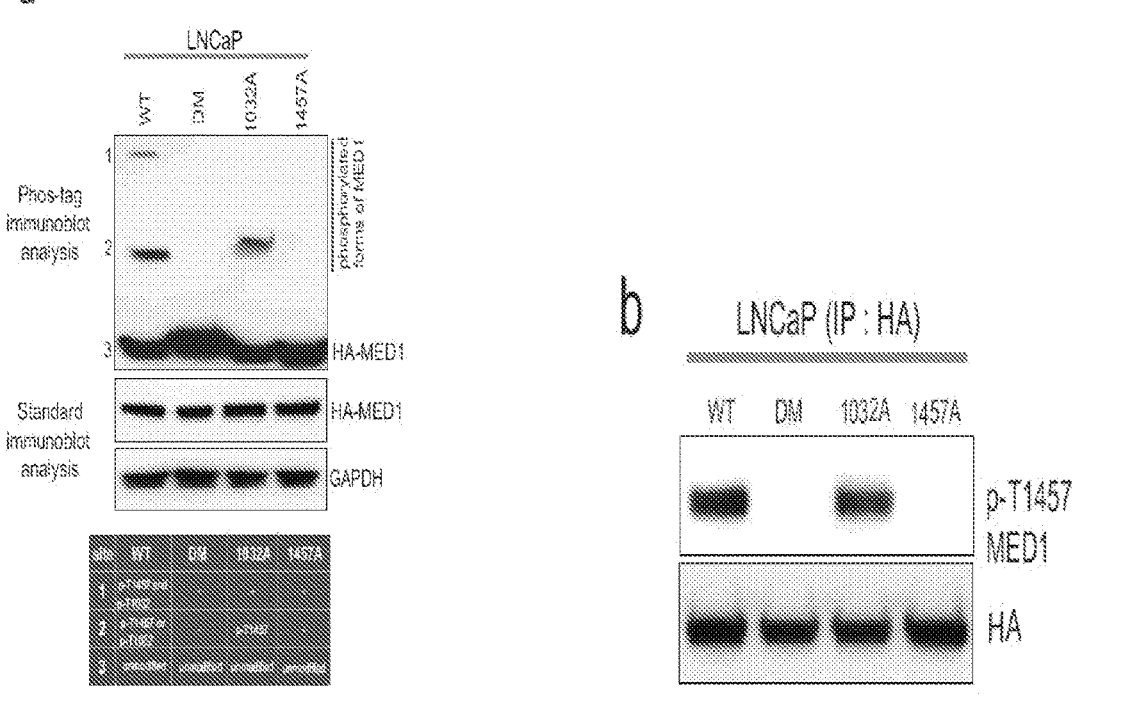
Figure 4A                    Figure 4B

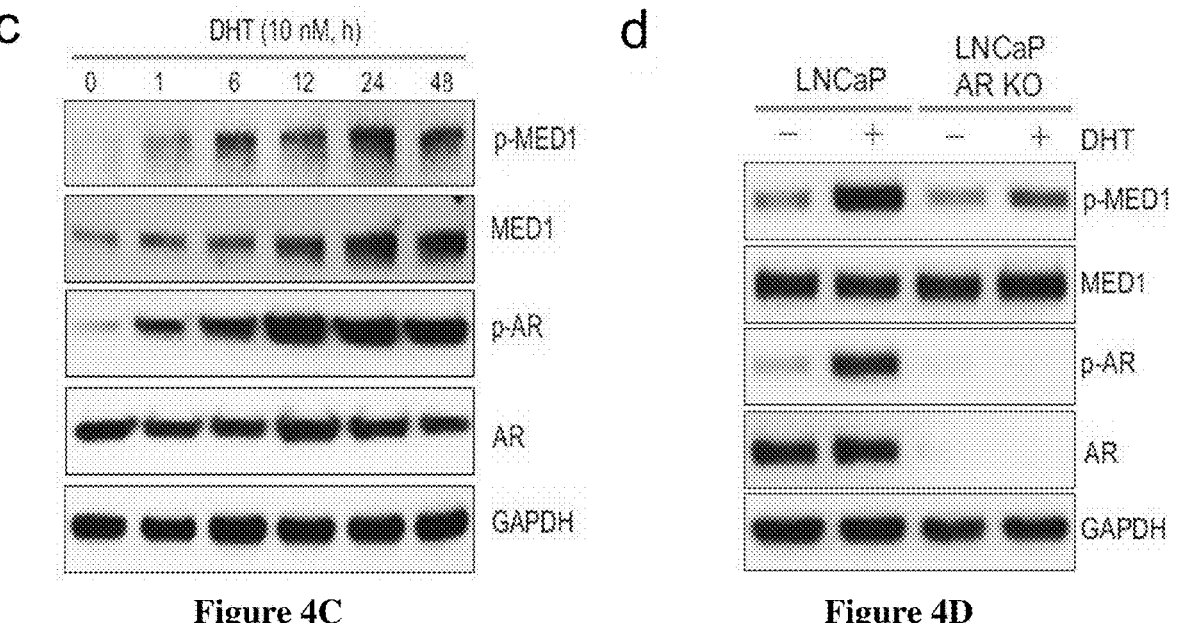
Figure 4C
Figure 4D
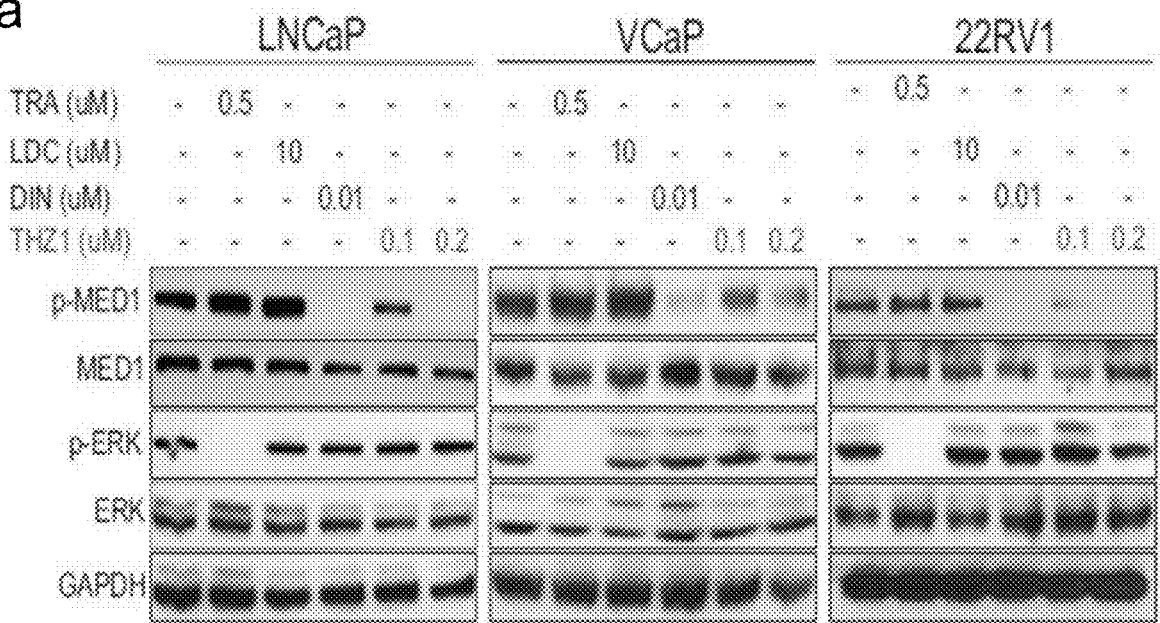
Figure 5A

Figure 5C  Figure 5D

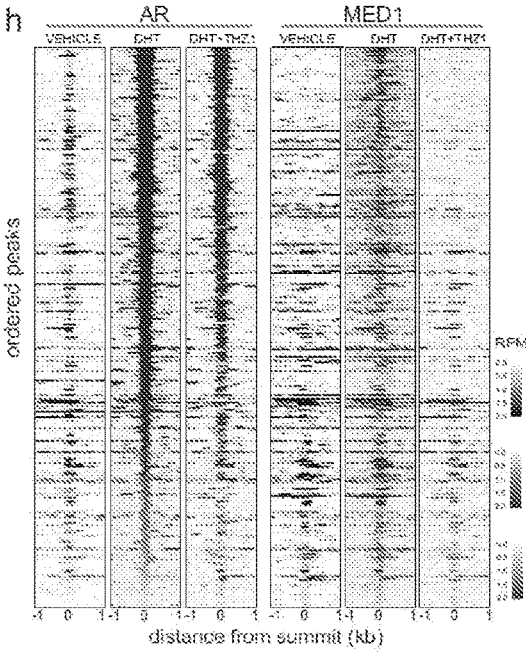
Figure 5H
Figure 5I
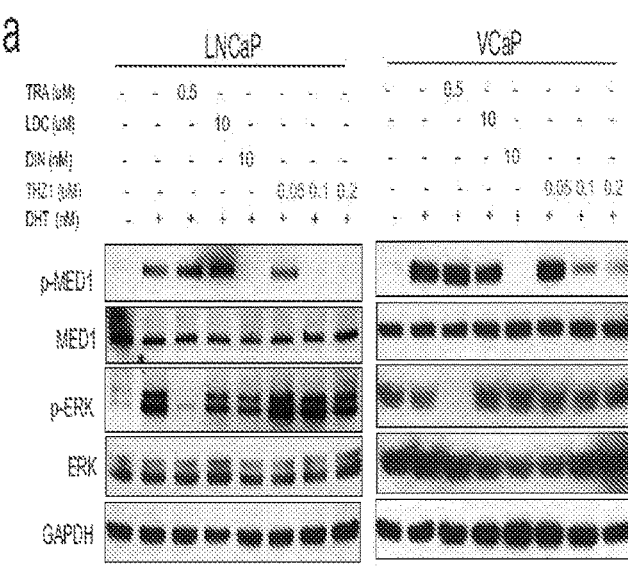
Figure 6A
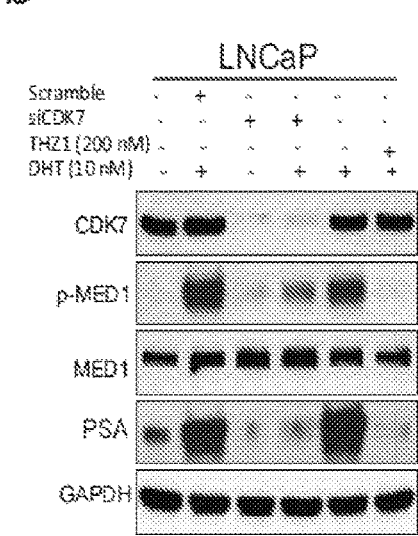
Figure 6B

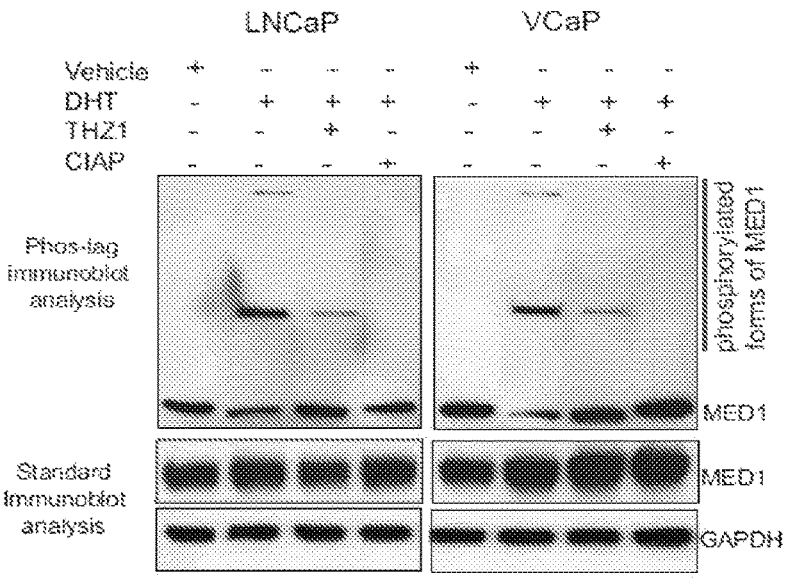
Figure 6E
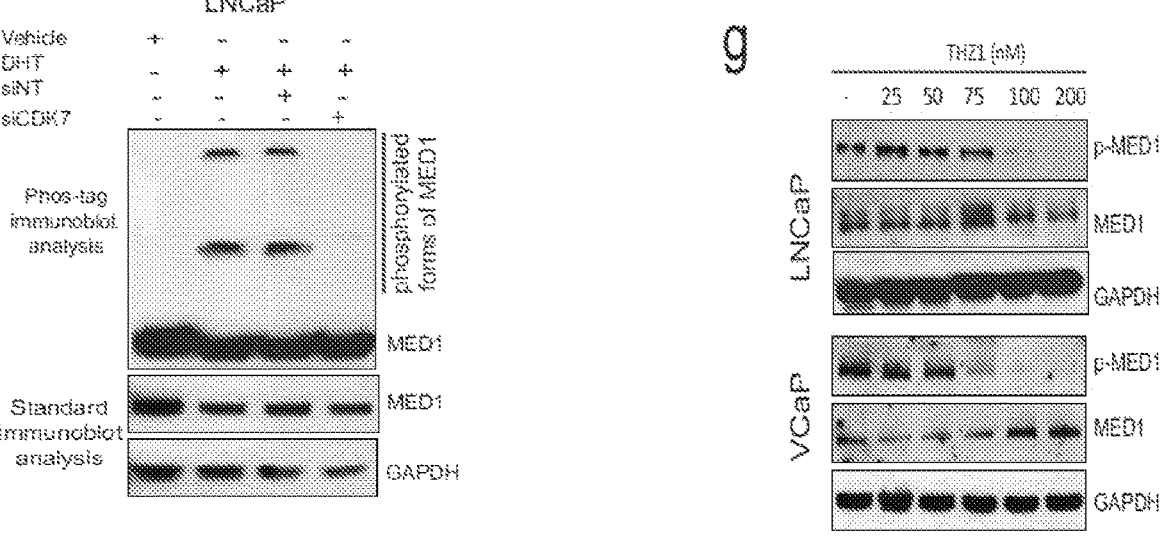
Figure 6F                    Figure 6G

Figure 7B          Figure 7C

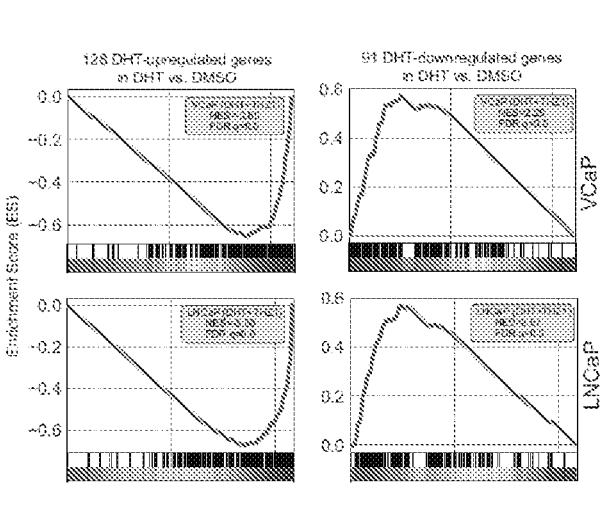
Figure 7E
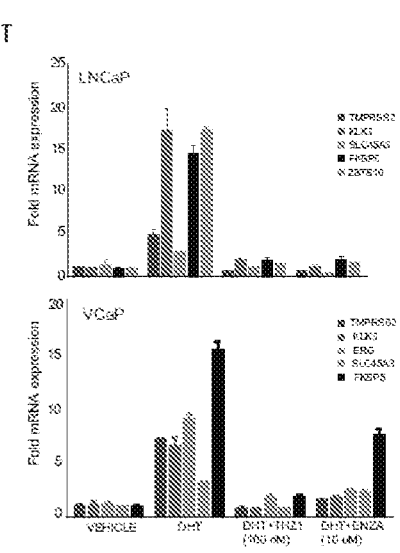
Figure 7F
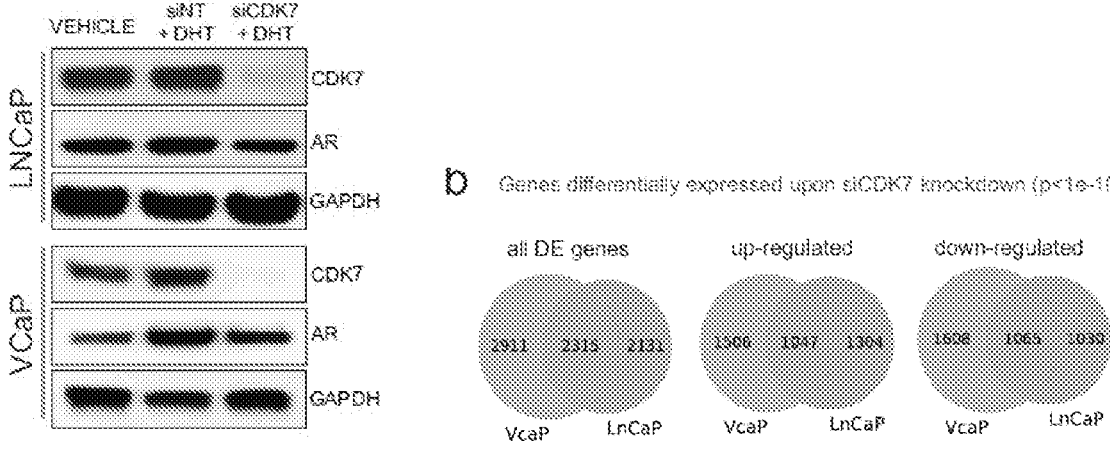
Figure 8A
Figure 8B

| Cell line | AR signaling status | THZ1 GI50 (nM) |
|---|---|---|
| LNCaP | Positive | 10 |
| LNCaP-AR | Positive | 50 |
| VCaP | Positive | 55 |
| LAPC4 | Positive | 155 |
| 22RV1 | Positive | 140 |
| DU145 | Negative | 385 |
| PC3 | Negative | 466 |
| RWPE | Negative | 610 |
Figure 9A
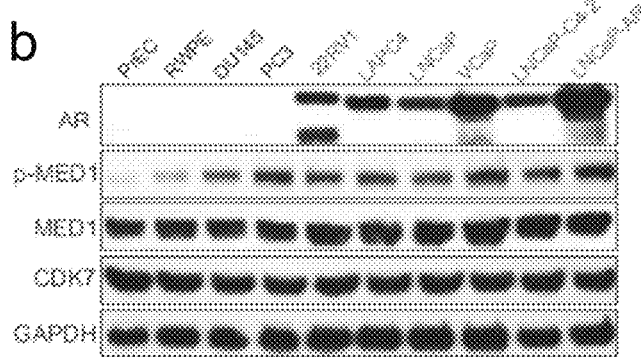
Figure 9B
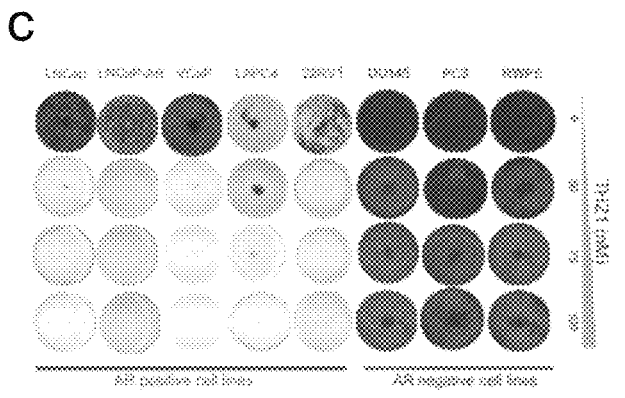
Figure 9C
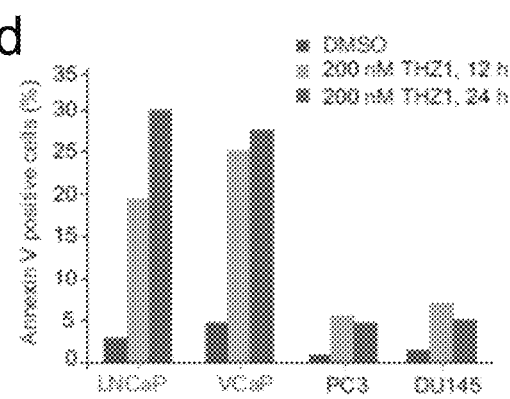
Figure 9D
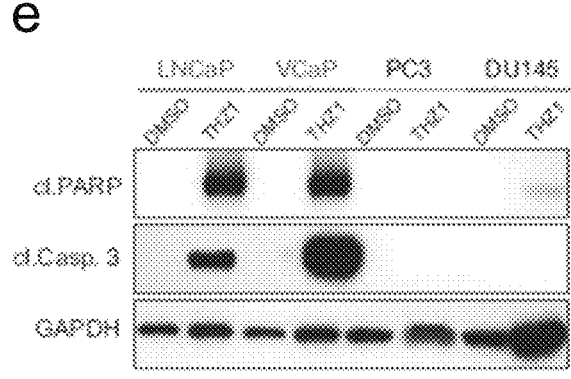
Figure 9E
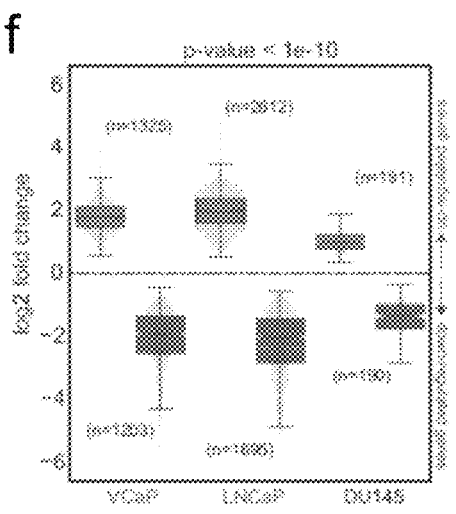
Figure 9F g i k a c a
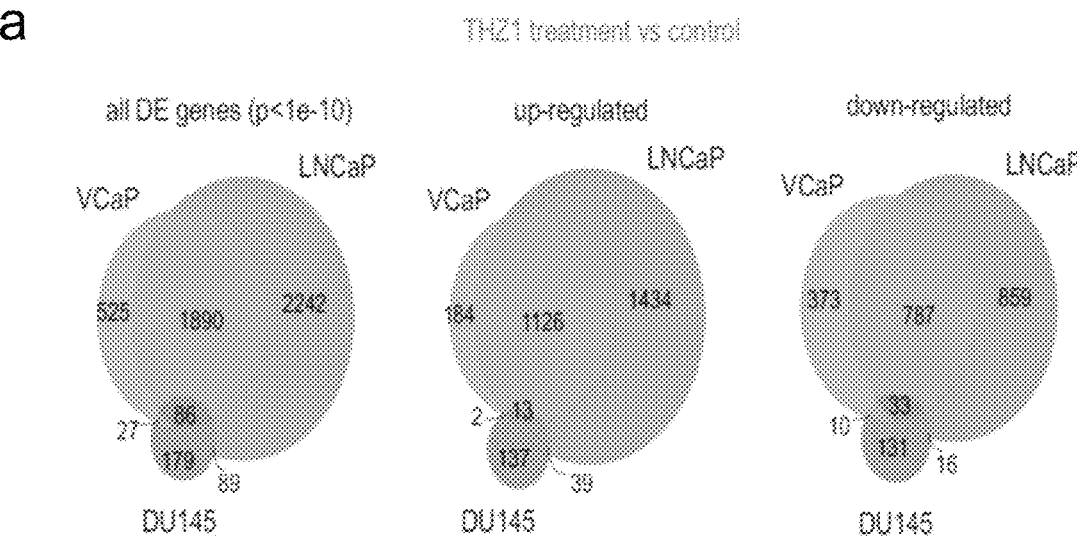
Figure 11A
b
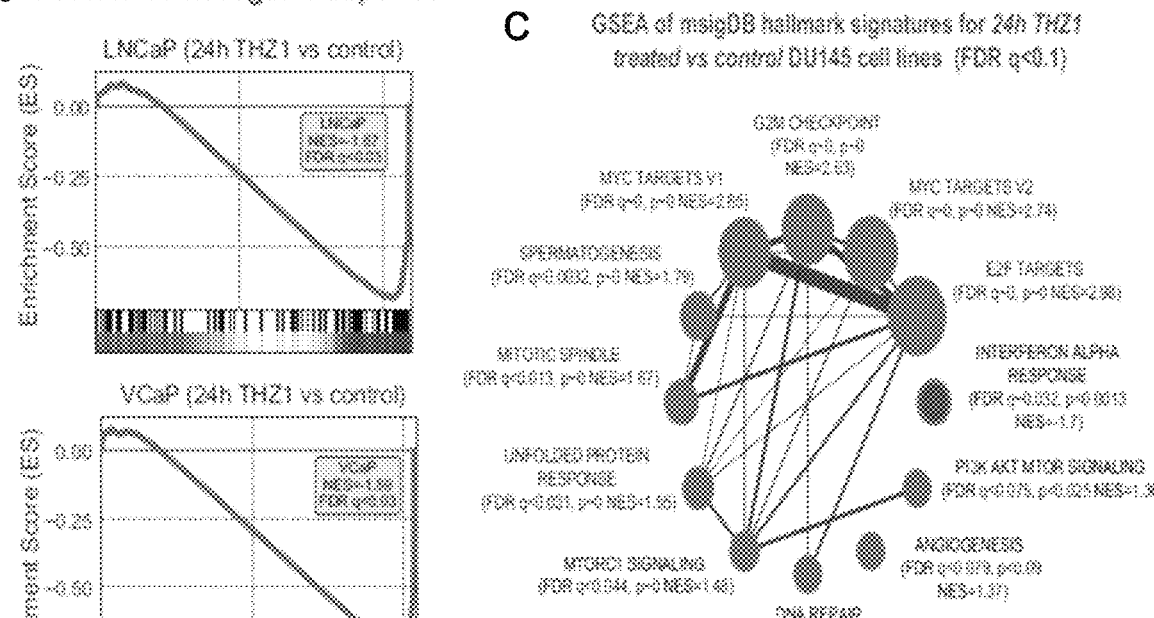
Figure 11B
Figure 11C d

GSEA with ERG signature e f b

C

| site | WT | DM | 1032A | 1457A |
|------|-----|-----|--------|--------|
| 1 | p-T1457 and p-T1032 | - | - | - |
| 2 | p-T1457 or p-T1032 | - | p-T1457 | - |
| 3 | unmodified | unmodified | unmodified | unmodified |

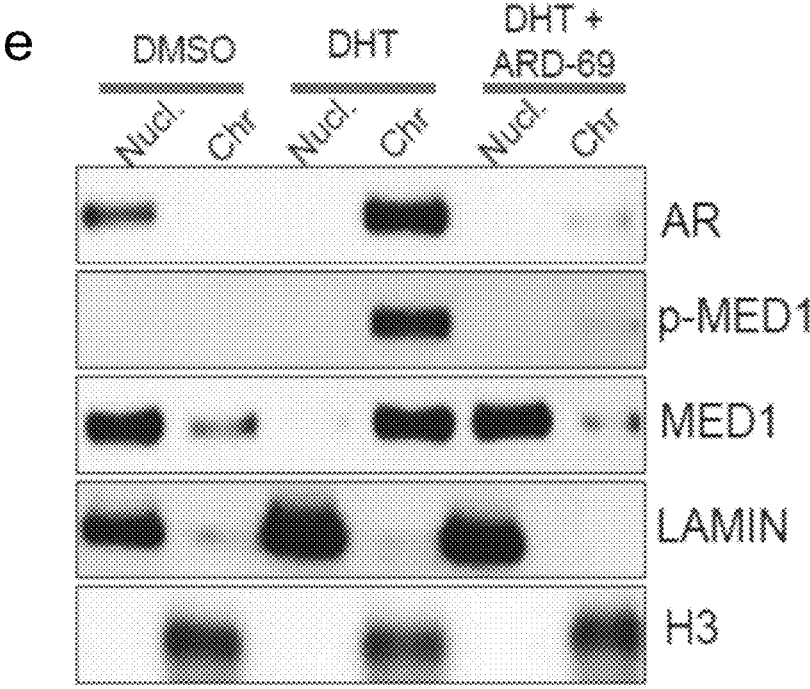
ARD-69 : AR degrader
Figure 18
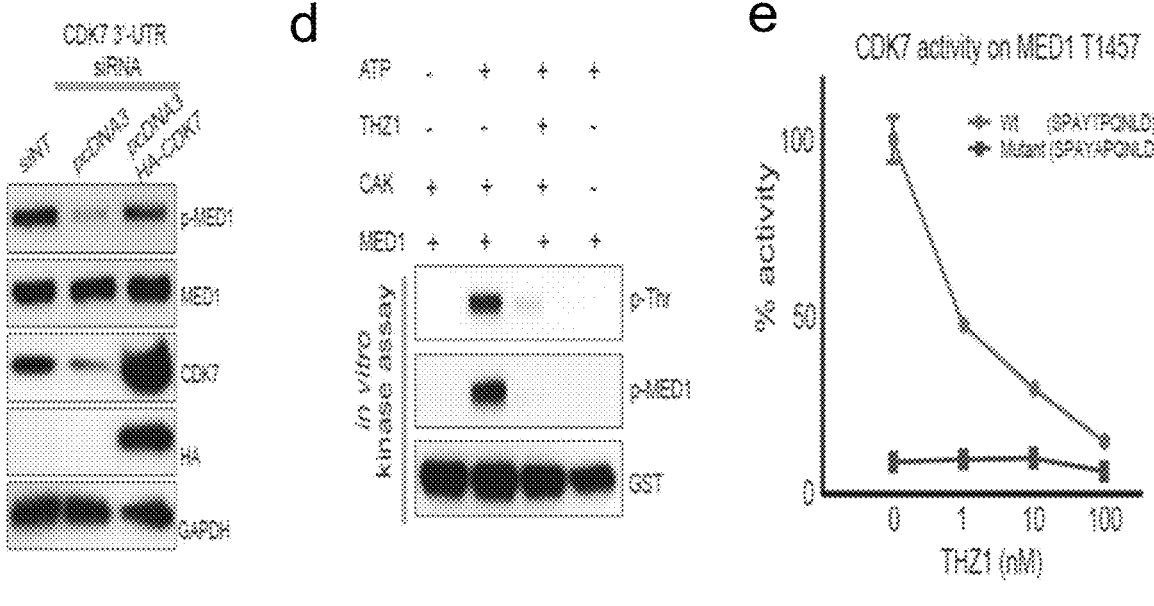
Figure 19A          Figure 19B          Figure 19C

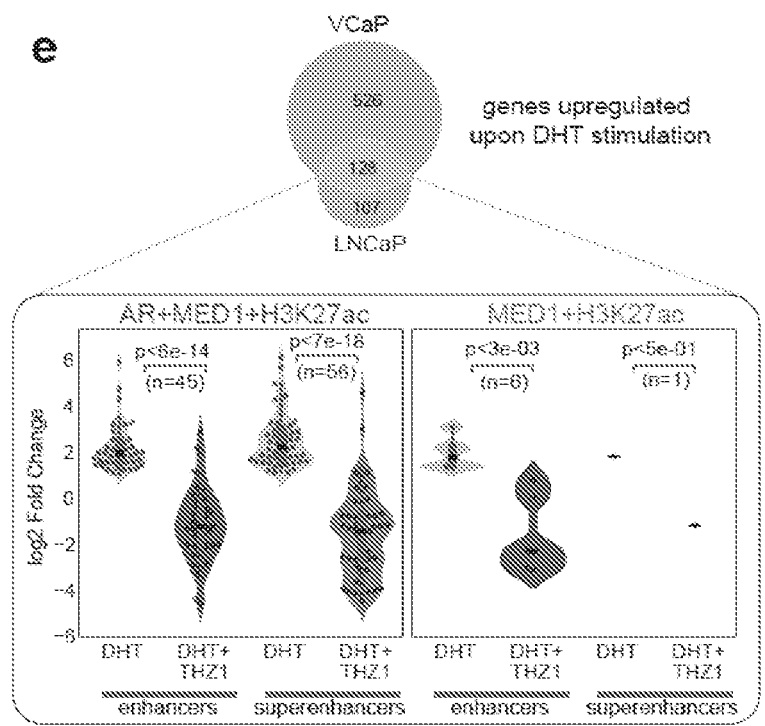

Figure 20E

| Cell line | Origin | AR signaling status | AR dysregulation | GI50 for THZ1 (nM) | CDK7 expression |
|---|---|---|---|---|---|
| LNCaP | lymph node metastatic prostate tumor | Positive | T877A mutation | 70 | + |
| LNCaP-AR | LNCaP with AR overexpression | Positive | ectopic AR overexpression | 60 | + |
| VCaP | vertebral metastasis | Positive | genomic AR amplification | 58 | + |
| LAPC4 | lymph node metastatic prostate tumor | Positive | Wildtype AR | 166 | + |
| 22RV1 | Mouse xenograft of bone metastasis | Positive | AR splice variant AR-V7 | 140 | + |
| DU145 | Brain metastasis | Negative | ~ | 385 | + |
| PC3 | vertebral metastasis | Negative | ~ | 466 | + |
| RWPE | Normal prostate | Negative | ~ | 610 | + |

Figure 21A

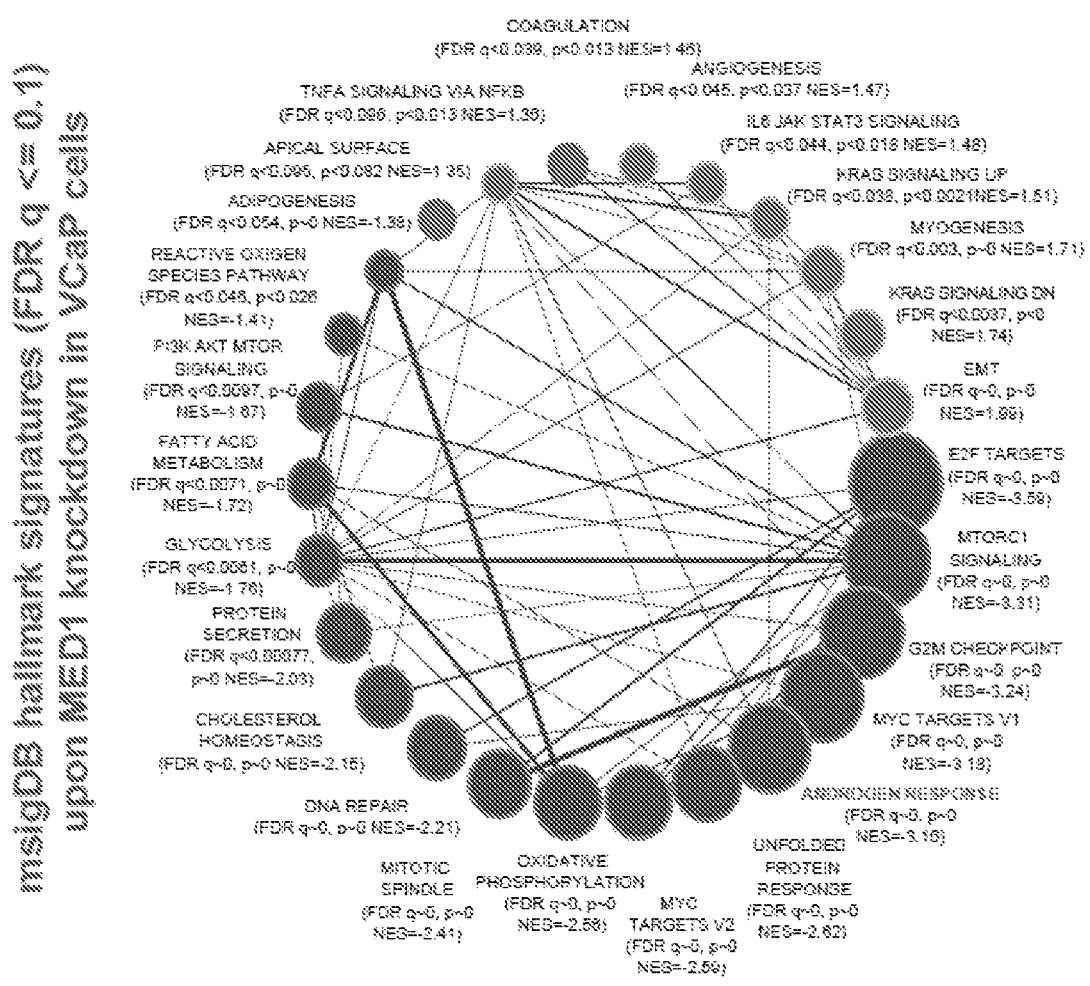
Figure 23B
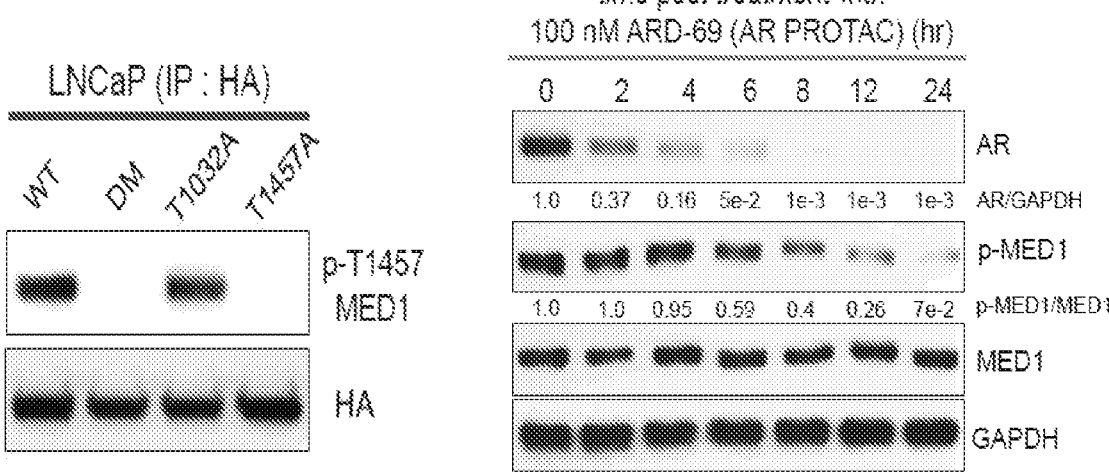
Figure 24A             Figure 24B

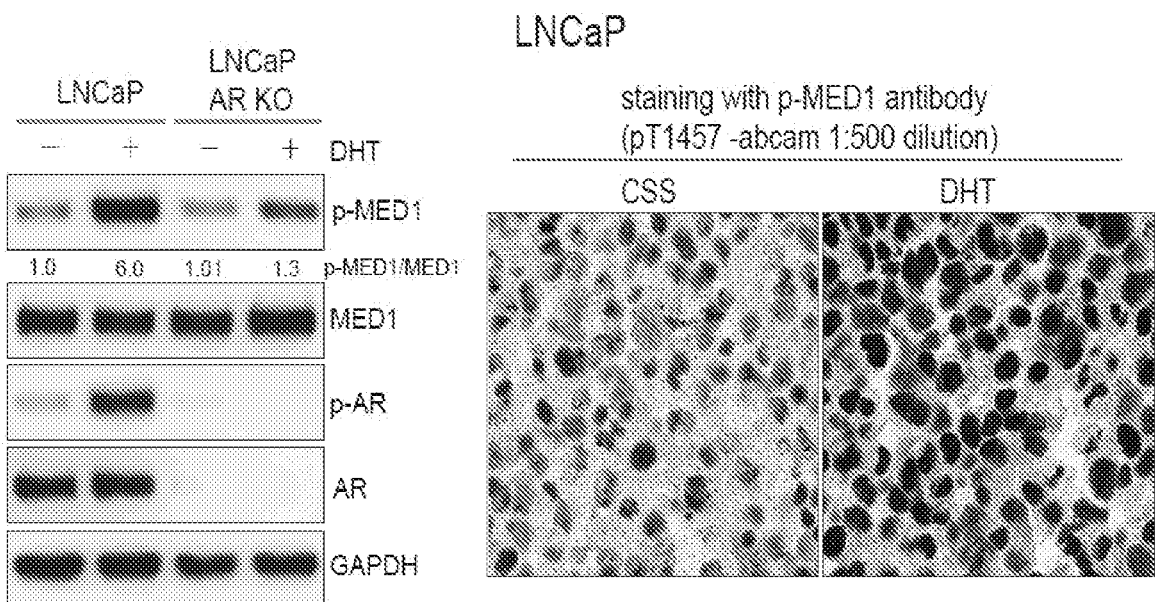
Figure 24C
Figure 24D
No antibody control for TMA
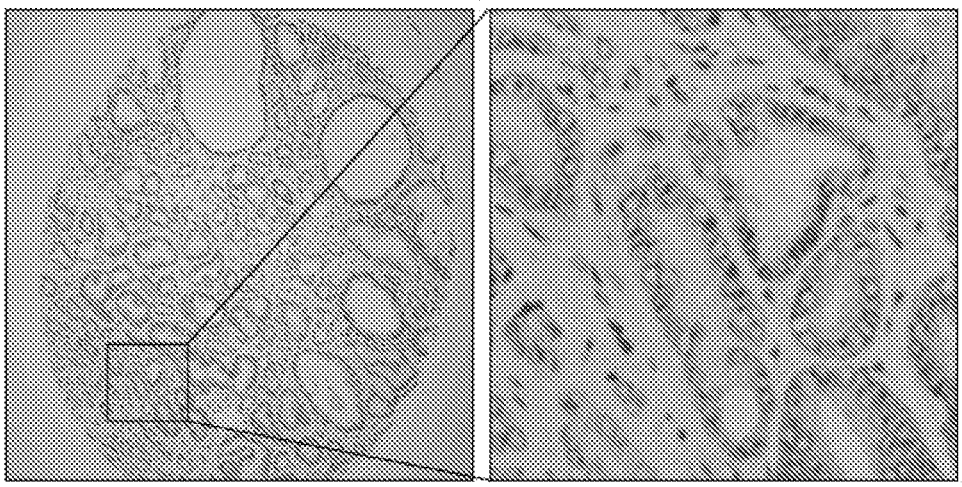
Figure 24E

Dose response:

Time course:

a

Chr.: Chromatin fraction

Nucl.: Nuclear soluble fraction b

SEQUENCE LISTING

```
<160> NUMBER OF SEQ ID NOS: 41

<210> SEQ ID NO 1
<211> LENGTH: 37
<212> TYPE: DNA
<213> ORGANISM: Artificial Sequence
<220> FEATURE:
<223> OTHER INFORMATION: MED1 (T1032A) fwd primer

<400> SEQUENCE: 1
gttcttctaa cagacctttt gccccaccta ccagtac                              37

<210> SEQ ID NO 2
<211> LENGTH: 37
<212> TYPE: DNA
<213> ORGANISM: Artificial Sequence
<220> FEATURE:
<223> OTHER INFORMATION: MED1 (T1032A) rev primer

<400> SEQUENCE: 2
gtactggtag gtggggcaaa aggtctgtta gaagaac                              37

<210> SEQ ID NO 3
<211> LENGTH: 38
<212> TYPE: DNA
<213> ORGANISM: Artificial Sequence
<220> FEATURE:
<223> OTHER INFORMATION: MED1 (T1457A) fwd primer

<400> SEQUENCE: 3
gccatagtaa gtcaccagca tatgcccccc agaatctg                             38
```

```
<210> SEQ ID NO 4
<211> LENGTH: 38
<212> TYPE: DNA
<213> ORGANISM: Artificial Sequence
<220> FEATURE:
<223> OTHER INFORMATION: MED1 (T1457A) rev primer

<400> SEQUENCE: 4
cagattctgg ggggcatatg ctggtgactt actatggc                              38

<210> SEQ ID NO 5
<211> LENGTH: 38
<212> TYPE: DNA
<213> ORGANISM: Artificial Sequence
<220> FEATURE:
<223> OTHER INFORMATION: MED1 (T1457D) fwd pimer

<400> SEQUENCE: 5
gccatagtaa gtcaccagca tatgacccccc agaatctg                             38

<210> SEQ ID NO 6
<211> LENGTH: 38
<212> TYPE: DNA
<213> ORGANISM: Artificial Sequence
<220> FEATURE:
<223> OTHER INFORMATION: MED1 (T1457D) rev primer

<400> SEQUENCE: 6
cagattctgg gggtcatatg ctggtgactt actatggc                              38

<210> SEQ ID NO 7
<211> LENGTH: 20
<212> TYPE: DNA
<213> ORGANISM: Artificial Sequence
<220> FEATURE:
<223> OTHER INFORMATION: zbtb16_qPCR_fwd primer

<400> SEQUENCE: 7
cagttttcga aggaggatgc                                                  20

<210> SEQ ID NO 8
<211> LENGTH: 20
<212> TYPE: DNA
<213> ORGANISM: Artificial Sequence
<220> FEATURE:
<223> OTHER INFORMATION: zbtb16_qPCR_rev primer

<400> SEQUENCE: 8
cccacacagc agacagaaga                                                  20

<210> SEQ ID NO 9
<211> LENGTH: 24
<212> TYPE: DNA
<213> ORGANISM: Artificial Sequence
<220> FEATURE:
<223> OTHER INFORMATION: erg_qPCR_fwd primer

<400> SEQUENCE: 9
cgcagagtta tcgtgccagc agat                                             24

<210> SEQ ID NO 10
<211> LENGTH: 24
<212> TYPE: DNA
<213> ORGANISM: Artificial Sequence
<220> FEATURE:
<223> OTHER INFORMATION: erg_qPCR_rev primer
```

-continued

```
<400> SEQUENCE: 10
ccatattctt tcaccgccca ctcc                                        24

<210> SEQ ID NO 11
<211> LENGTH: 21
<212> TYPE: DNA
<213> ORGANISM: Artificial Sequence
<220> FEATURE:
<223> OTHER INFORMATION: psa (klk3)_qPCR_fwd primer

<400> SEQUENCE: 11
acgctggaca gggggcaaaa g                                           21

<210> SEQ ID NO 12
<211> LENGTH: 21
<212> TYPE: DNA
<213> ORGANISM: Artificial Sequence
<220> FEATURE:
<223> OTHER INFORMATION: psa (klk3)_qPCR_rev primer

<400> SEQUENCE: 12
gggcagggca catggttcac t                                           21

<210> SEQ ID NO 13
<211> LENGTH: 25
<212> TYPE: DNA
<213> ORGANISM: Artificial Sequence
<220> FEATURE:
<223> OTHER INFORMATION: tmprss2_qPCR_fwd primer

<400> SEQUENCE: 13
caggagtgta cgggaatgtg atggt                                       25

<210> SEQ ID NO 14
<211> LENGTH: 24
<212> TYPE: DNA
<213> ORGANISM: Artificial Sequence
<220> FEATURE:
<223> OTHER INFORMATION: tmprss2_qPCR_rev primer

<400> SEQUENCE: 14
gattagccgt ctgccctcat ttgt                                        24

<210> SEQ ID NO 15
<211> LENGTH: 20
<212> TYPE: DNA
<213> ORGANISM: Artificial Sequence
<220> FEATURE:
<223> OTHER INFORMATION: fkbp5_qPCR_fwd primer

<400> SEQUENCE: 15
tctcatgtct ccccagttcc                                             20

<210> SEQ ID NO 16
<211> LENGTH: 20
<212> TYPE: DNA
<213> ORGANISM: Artificial Sequence
<220> FEATURE:
<223> OTHER INFORMATION: fkbp5_qPCR_rev primer

<400> SEQUENCE: 16
ttctggcttt cacgtctgtg                                             20

<210> SEQ ID NO 17
```

-continued

<211> LENGTH: 19
<212> TYPE: DNA
<213> ORGANISM: Artificial Sequence
<220> FEATURE:
<223> OTHER INFORMATION: slc45a3_qPCR_fwd primer

<400> SEQUENCE: 17
tcgtgggcga ggggctgta                                                        19

<210> SEQ ID NO 18
<211> LENGTH: 25
<212> TYPE: DNA
<213> ORGANISM: Artificial Sequence
<220> FEATURE:
<223> OTHER INFORMATION: slc45a3_qPCR_rev primer

<400> SEQUENCE: 18
catccgaacg ccttcatcat agtgt                                                 25

<210> SEQ ID NO 19
<211> LENGTH: 20
<212> TYPE: DNA
<213> ORGANISM: Artificial Sequence
<220> FEATURE:
<223> OTHER INFORMATION: ar_qPCR_fwd primer

<400> SEQUENCE: 19
cagtggatgg gctgaaaaat                                                       20

<210> SEQ ID NO 20
<211> LENGTH: 20
<212> TYPE: DNA
<213> ORGANISM: Artificial Sequence
<220> FEATURE:
<223> OTHER INFORMATION: ar_qPCR_rev primer

<400> SEQUENCE: 20
ggagcttggt gagctggtag                                                       20

<210> SEQ ID NO 21
<211> LENGTH: 20
<212> TYPE: DNA
<213> ORGANISM: Artificial Sequence
<220> FEATURE:
<223> OTHER INFORMATION: gapdh_qPCR_fwd primer

<400> SEQUENCE: 21
tgcaccacca actgcttagc                                                       20

<210> SEQ ID NO 22
<211> LENGTH: 21
<212> TYPE: DNA
<213> ORGANISM: Artificial Sequence
<220> FEATURE:
<223> OTHER INFORMATION: gapdh_qPCR_rev primer

<400> SEQUENCE: 22
ggcatggact gtggtcatga g                                                     21

<210> SEQ ID NO 23
<211> LENGTH: 21
<212> TYPE: DNA
<213> ORGANISM: Artificial Sequence
<220> FEATURE:
<223> OTHER INFORMATION: KLK3 fwd primer

<400> SEQUENCE: 23

-continued

```
acgctggaca gggggcaaaa g                                              21

<210> SEQ ID NO 24
<211> LENGTH: 21
<212> TYPE: DNA
<213> ORGANISM: Artificial Sequence
<220> FEATURE:
<223> OTHER INFORMATION: KLK3 rev primer

<400> SEQUENCE: 24
gggcagggca catggttcac t                                              21

<210> SEQ ID NO 25
<211> LENGTH: 25
<212> TYPE: DNA
<213> ORGANISM: Artificial Sequence
<220> FEATURE:
<223> OTHER INFORMATION: TMPRSS2 fwd primer

<400> SEQUENCE: 25
caggagtgta cgggaatgtg atggt                                          25

<210> SEQ ID NO 26
<211> LENGTH: 24
<212> TYPE: DNA
<213> ORGANISM: Artificial Sequence
<220> FEATURE:
<223> OTHER INFORMATION: TMPRSS2 rev primer

<400> SEQUENCE: 26
gattagccgt ctgccctcat ttgt                                           24

<210> SEQ ID NO 27
<211> LENGTH: 20
<212> TYPE: DNA
<213> ORGANISM: Artificial Sequence
<220> FEATURE:
<223> OTHER INFORMATION: FKBP5 fwd primer

<400> SEQUENCE: 27
tctcatgtct ccccagttcc                                                20

<210> SEQ ID NO 28
<211> LENGTH: 20
<212> TYPE: DNA
<213> ORGANISM: Artificial Sequence
<220> FEATURE:
<223> OTHER INFORMATION: FKBP5 rev primer

<400> SEQUENCE: 28
ttctggcttt cacgtctgtg                                                20

<210> SEQ ID NO 29
<211> LENGTH: 19
<212> TYPE: DNA
<213> ORGANISM: Artificial Sequence
<220> FEATURE:
<223> OTHER INFORMATION: SLC45A3 fwd primer

<400> SEQUENCE: 29
tcgtgggcga ggggctgta                                                 19

<210> SEQ ID NO 30
<211> LENGTH: 25
<212> TYPE: DNA
```

```
<213> ORGANISM: Artificial Sequence
<220> FEATURE:
<223> OTHER INFORMATION: SLC45A3 rev primer

<400> SEQUENCE: 30
catccgaacg ccttcatcat agtgt                                          25

<210> SEQ ID NO 31
<211> LENGTH: 20
<212> TYPE: DNA
<213> ORGANISM: Artificial Sequence
<220> FEATURE:
<223> OTHER INFORMATION: ZBTB16 fwd primer

<400> SEQUENCE: 31
cagttttcga aggaggatgc                                               20

<210> SEQ ID NO 32
<211> LENGTH: 20
<212> TYPE: DNA
<213> ORGANISM: Artificial Sequence
<220> FEATURE:
<223> OTHER INFORMATION: ZBTB16 rev primer

<400> SEQUENCE: 32
cccacacagc agacagaaga                                               20

<210> SEQ ID NO 33
<211> LENGTH: 20
<212> TYPE: DNA
<213> ORGANISM: Artificial Sequence
<220> FEATURE:
<223> OTHER INFORMATION: GAPDH fwd primer

<400> SEQUENCE: 33
tgcaccacca actgcttagc                                               20

<210> SEQ ID NO 34
<211> LENGTH: 21
<212> TYPE: DNA
<213> ORGANISM: Artificial Sequence
<220> FEATURE:
<223> OTHER INFORMATION: GAPDH rev primer

<400> SEQUENCE: 34
ggcatggact gtggtcatga g                                             21

<210> SEQ ID NO 35
<211> LENGTH: 20
<212> TYPE: DNA
<213> ORGANISM: Artificial Sequence
<220> FEATURE:
<223> OTHER INFORMATION: AR fwd primer

<400> SEQUENCE: 35
cagtggatgg gctgaaaaat                                               20

<210> SEQ ID NO 36
<211> LENGTH: 20
<212> TYPE: DNA
<213> ORGANISM: Artificial Sequence
<220> FEATURE:
<223> OTHER INFORMATION: AR rev primer

<400> SEQUENCE: 36
ggagcttggt gagctggtag                                               20
```

-continued

```
<210> SEQ ID NO 37
<211> LENGTH: 24
<212> TYPE: DNA
<213> ORGANISM: Artificial Sequence
<220> FEATURE:
<223> OTHER INFORMATION: ERG fwd primer

<400> SEQUENCE: 37
cgcagagtta tcgtgccagc agat                                        24

<210> SEQ ID NO 38
<211> LENGTH: 24
<212> TYPE: DNA
<213> ORGANISM: Artificial Sequence
<220> FEATURE:
<223> OTHER INFORMATION: ERG rev primer

<400> SEQUENCE: 38
ccatattctt tcaccgccca ctcc                                        24

<210> SEQ ID NO 39
<211> LENGTH: 4
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = Ser or Thr
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa = Lys or Arg

<400> SEQUENCE: 39

Xaa Pro Xaa Xaa
1

<210> SEQ ID NO 40
<211> LENGTH: 7
<212> TYPE: PRT
<213> ORGANISM: Homo sapiens

<400> SEQUENCE: 40

Tyr Ser Pro Thr Ser Thr Ser
1               5

<210> SEQ ID NO 41
<211> LENGTH: 7
<212> TYPE: PRT
<213> ORGANISM: Homo sapiens

<400> SEQUENCE: 41

Tyr Ser Pro Thr Ser Pro Ser
1               5
```

TREATMENT OF CANCER WITH CDK INHIBITORS

CROSS-REFERENCE TO RELATED APPLICATIONS

This application is a National Phase Application of PCT International Application No. PCT/US2020/029883, International Filing Date Apr. 24, 2020, claiming the benefit of U.S. Patent Application No. 62/838,271, filed Apr. 24, 2019, which is/are hereby incorporated by reference.

REFERENCE TO A SEQUENCE LISTING SUBMITTED ELECTRONICALLY

The contents of the text filed named "P-585580-PC-24APR20_ST25.txt", which was created on Apr. 24, 2020 and is 8,227 bytes in size, are hereby incorporated by reference in their entirety.

FIELD OF THE INVENTION

The present invention relates to methods of treating cancer by administration of a cyclin dependent kinase (CDK) inhibitor to a subject.

BACKGROUND OF THE INVENTION

Cancer remains among the leading causes of death throughout the world. Prostate cancer (PCa) is the most common non-cutaneous malignancy and the second leading cause of cancer-related mortality in men of the western world. While effective surgical, radiation, and androgen ablation therapies exist for clinically localized prostate cancer, progression to metastatic castration-resistant prostate cancer (CRPC) is essentially incurable. The Androgen receptor (AR) is a major driver alteration in CRPC, and most prostate tumors remain addicted to AR-mediated transcription. Maintenance of AR-signaling is the most frequent resistance mechanism in CRPC patients that develops after conventional hormone deprivation and newer generation antiandrogen therapies. Genetic and epigenetic events lead to AR amplification, mutation, and alternative splicing, resulting in the observed AR-driven transcriptional addiction seen in CRPC.

Despite recent advances in anti-androgen therapy, 20-40% of patients with metastatic CRPC demonstrate de novo resistance to the FDA-approved drugs abiraterone and enzalutamide, and many of the responders acquire resistance resulting in a limited survival benefit.

The evolutionarily conserved multi-subunit Mediator complex plays a central role in the regulation of gene transcription by virtue of its ability to functionally bridge gene-specific transcription factors with the RNA polymerase II-associated basal transcription machinery. MED1 (also known as TRAP220, PBP, and DRIP205) is a key component of the Mediator complex, and is responsible for targeting and anchoring the complex to both cell type-specific transcription factors and a broad range of nuclear receptors (NR), including AR. Despite its pivotal role in transcription, very little is known about the molecular determinants that regulate the formation of a functional MED1-AR complex.

Accordingly, there remains an urgent need in the art for improved therapies and molecular approaches that more effectively block the AR-transcriptional axis, thereby treating cancers and other diseases associated with this pathway, such as CRPC.

SUMMARY OF THE INVENTION

In an aspect, provided herein is a method of treating a cancer in a subject, comprising administering to a subject in need thereof an effective amount of a cyclin dependent kinase (CDK) inhibitor, thereby treating cancer in the subject.

In another aspect, provided herein is a method of treating a cancer in a subject, comprising administering to a subject in need thereof a pharmaceutical composition comprising an effective amount of a cyclin dependent kinase (CDK) inhibitor, thereby treating cancer in the subject.

In another aspect, provided herein is a method of treating a disease in a subject, said disease characterized by androgen receptor (AR) dependent neoplastic growth, comprising administering to a subject in need thereof, an agent effective to inhibit MED1-mediated, AR-dependent oncogenic transcriptional amplification, thereby treating the disease.

In an aspect, provided herein is a method of treating an androgen receptor (AR) dependent cancer in a human subject in need thereof, the method comprising:

a) testing a cancer tissue sample obtained from the human subject to determine a nuclear phosphorylated-MED1 (p-MED1) level in the cancer tissue sample;

b) comparing the determined nuclear p-MED1 level in step (a) with a predetermined nuclear p-MED1 level in a control tissue sample, wherein the control tissue sample is a non-malignant (benign) tissue sample, a localized (primary) cancer tissue sample and/or a metastatic cancer tissue sample; wherein (i) a determined nuclear p-MED1 level that is increased compared to the predetermined nuclear p-MED1 level in the localized (primary) cancer tissue sample and/or in the metastatic cancer tissue sample is indicative of a poor prognosis, and (ii) a determined nuclear p-MED1 level that is decreased compared to the predetermined nuclear p-MED1 level in the non-malignant (benign) tissue sample is indicative of a good prognosis; and (c) administering to the human subject having (i) a determined nuclear p-MED1 level indicative of a good prognosis a therapeutically effective amount of an inhibitor of a cyclin dependent kinase (CDK) inhibitor, or administering to the human subject having (ii) a determined nuclear p-MED1 level indicative of a poor prognosis a therapeutically effective amount of an inhibitor of a cyclin dependent kinase (CDK) inhibitor and of an anti-androgen therapy, wherein the administering is sequential in either order or concurrent.

In another aspect, provided herein is a method for predicting a prognosis of an androgen receptor (AR) dependent cancer and a response to cyclin dependent kinase (CDK) inhibition in a subject, the method comprising:

(a) measuring a nuclear p-MED1 level in a cancer tissue sample obtained from the human subject;

b) comparing the nuclear p-MED1 level measured in step (a) with a predetermined nuclear p-MED1 level in a control tissue sample, wherein the control tissue sample is a non-malignant (benign) tissue sample, a localized (primary) cancer tissue sample and/or a metastatic cancer tissue sample; wherein (i) a determined nuclear p-MED1 level that is increased compared to the predetermined nuclear p-MED1 level in the localized (primary) cancer tissue sample and/or in the metastatic cancer tissue sample is indicative of a poor prognosis, and (ii) a determined nuclear p-MED1 level that is decreased compared to the predetermined nuclear p-MED1 level in the non-malignant (benign)

tissue sample is indicative of a good prognosis, wherein administration of a therapeutically effective amount of a CDK inhibitor to the human subject having (ii) a determined nuclear p-MED1 level indicative of a good prognosis is predictive of a therapeutic response to the CDK inhibitor, and wherein administration of a therapeutically effective amount of a CDK inhibitor to the human subject having (i) a determined nuclear p-MED1 level indicative of a poor prognosis is not predictive of a therapeutic response to the CDK inhibitor and requires further administration of a therapeutically effective amount of an anti-androgen therapy.

In still another aspect, provided herein is a method for predicting a prognosis of an androgen receptor (AR) dependent prostate cancer in a human subject and for treating the AR dependent prostate cancer, the method comprising:

a) measuring an expression level of an AR target gene in a prostate cancer tissue sample obtained from the human subject, wherein the AR target gene comprises 2 to 128 genes selected from a gene-signature consisting of PGM3, TMCC3, APPBP2, PLPP1, TUBA3D, CAPZB, KIF22, ZCCHC6, LAT2, LRRFIP2, FKBP5, MRPS18A, SMS, NDFIP2, ABCC1, NDRG1, MTMR9, AGR2, BMPR1A, LRRC59, SNX25, TRIM3, CAMKK2, KRT18, SASH1, HMGCR, LIFR, HMGXB3, SSR3, ODC1, DHCR24, RHOU, UAP1, ELL2, PCMT1, SOCS2, CHRNA2, ORMDL2, PFKFB2, ACSL3, PMEPA1, SPDEF, SSR1, STEAP4, LDLR, GADD45G, SELENOS, FADS2, MICAL1, KCTD3, LRRC8A, HERC3, BMPR1B, SHROOM3, FGD4, IGFIR, PCTP, KLK3, MPC2, CREB3L4, MBOAT2, LRIG1, EAF2, SDK1, NSDHL, CSGAL-NACT1, VLDLR, GLUD1, ENDOD1, GLB1L2, ACAD8, THYN1, VPS27B, NCAPD3, PART1, MERTK, PRKCA, DBI, TTN, KCNMA1, CLDN8, ATAD2, PEX10, ELK4, SLC45A3, NBL1, AZGP1, CDC42EP3, FZD5, ATP1A1, SLC15A2, TMEM79, SSR2, KLF15, SEC11C, B2M, NNMT, NKX3-1, C19orf48, FASN, KRT8, EFCAB12, KLC2, DOLK, ZNF613, LDLRAD3, SSR4, MFSD5, C1orf116, TMEM50A, TMPRSS2, HIST2H2BE, ATP6V0A2, FAM174B, ANKRD37, INSIG1, C9orf152, MYBPC1, STK39, MTOR, UBE2J1, FICD, PTPRCAP, AMACR, ZNF350, OTUD7B, PRAG1, and PAGR1, b) comparing the level of RNA expression of the AR target gene in the prostate cancer tissue sample from the human subject to a control RNA expression level of the AR target gene in a prostate tissue sample obtained from a healthy human subject, wherein an at least 2-fold increase in the expression level of the 2 to 128 genes indicates a poor prognosis for the androgen receptor (AR) dependent prostate cancer in the human subject;

c) identifying the human subject as being prone to not respond to CDK inhibition as a monotherapy based on the at least 2-fold increase in the expression level of the 2 to 128 genes as compared to the control RNA expression level of the AR target gene in the prostate tissue sample obtained from the healthy human subject; and d) administering to the human subject identified in step (c) a combination therapy comprising a therapeutically effective amount of an inhibitor of a cyclin dependent kinase (CDK) inhibitor and of an anti-androgen therapy, wherein the administering is sequential, in either order, or concurrent.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 3: MED1 knockdown blocks AR-mediated transcription and growth associated pathways in PCa cells. (a) Immunoblot validation of MED1 knockdown in LNCaP and VCaP cells, grown in steroid-depleted media for 72 h followed by vehicle or 10 nM DHT stimulation for 12 h, showing that the total AR levels remain unchanged upon MED1 knockdown. GAPDH was used as the loading control. (b) Relative expression levels of bona fide AR-target genes, with respect to GAPDH, as determined by qRT-PCR using total RNA extracted from cells as in (a). Data show mean±S.E. (n=3) from one of the two independent experiments. (c) Venn diagram showing the degree of overlap between genes differentially expressed (with p<1e-10) as determined by RNA-seq upon MED1 knockdown in VCaP and LNCaP cells. The left, middle and right panels correspond to all differentially-expressed, up-regulated, and down-regulated genes, respectively. (d) Heatmap representation of FPKM values for genes commonly up- and down-regulated upon MED1 knockdown; the colors represent the FPKM z-score and only genes with FPKM>0.5 in all samples were considered. (e) GSEA network plot of the various msigDB hallmark signatures displaying positive (red) and negative (blue) enrichment, with a significance of FUR q<=0.1, in siMED1 knockdown LNCaP and VCaP cells. Here, the yellow and green outlines represent signatures enriched positively and negatively, respectively, in both cell lines. MED1 knockdown leads to negative enrichment of the hallmark androgen response genes (indicated in bold) in VCaP and LNCaP cells.

FIG. 4: AR activation leads to phosphorylation of Thr1457 on MED1. (a) LNCaP Cells were transfected with HA-tagged wild-type (WT), double mutant (DM), T1032A or T1457A mutant MED1 plasmids for 72 h. The proteins were extracted and used for Phos-tag SDS-PAGE and standard immunoblotting with HA antibody. The table below indicates the identity of bands present on the phos-tag blot. Bands marked 1, 2 and 3 correspond to phosphorylation of both T1032 and T1457, either T1032 or T1457, and neither T1032 nor T1457, respectively. DM and 1457A completely abolish signal at 1 and 2, while 1032A abolishes the signal only at 1, establishing T1457 phosphorylation as a prerequisite for T1032 phosphorylation of MED1. (b) Validation of p-T1457 MED1 specific antibody. Immunoprecipitation of HA-tagged WT, single and double mutant MED1 followed by immunoblotting with the p-T1457 specific antibody was carried out in LNCaP cells, with HA as the IP control. In agreement with our findings in panel (a), p-1457 MED1 signal was completely lost in both DM and 1457A mutants but remained intact in 1032A mutant which clearly establishes the high specificity of p-T1457 MED1 antibody for p-MED1. (c) Immunoblot analysis showing the time dependent increase in p-MED1 (p-T1457 MED1) levels by DHT stimulation. (d) DHT induces MED1 phosphorylation in AR proficient but not in AR-deficient PCa cells. Isogenic LNCaP and LNCaP AR knockout (LNCaP AR KO) cells were grown in steroid deprived media for 3 days followed by stimulation with 10 nM DHT for 12 h. The total proteins extracted was used for immunoblotting analysis with p-MED1, MED1, p-AR (we used ps81-AR antibody to target an active chromatin-bound form of AR) and AR antibodies, with GAPDH as loading control.

Figure 1A:
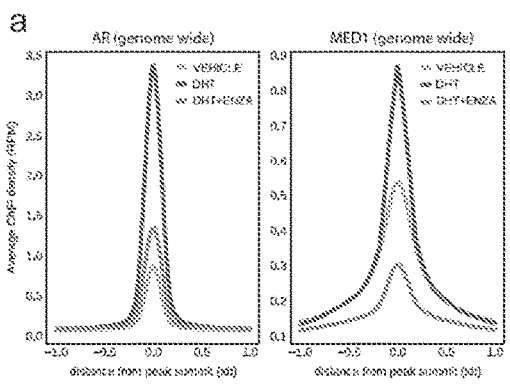
FIG. 1: MED1 undergoes phosphorylation upon androgen stimulation and is recruited to AR bound super-enhancers. (a) AR activation increases MED1 recruitment to the chromatin. Genome-wide averaged AR and MED1 ChIP-seq enrichment in VCaP cells grown in steroid-deprived serum containing media for 3 days, followed by 12 h stimulation with 10 nM DHT or DHT plus 5 μM enzalutamide. (b) Rank ordered H3K27ac ChIP-seq signal showing the presence of enhancers and super-enhancer (SE) regions in VCaP cells. (c) Preferential binding of MED1 to the AR bound SE. Pie chart displaying the overlap of H3K27ac enhancers and SE with AR and/or MED1 peaks. (d) Anti-androgen reverses MED1 binding to SE. Normalized enrichment of AR and MED1 in the enhancers and SE in the presence of DHT and/or ENZA in VCaP cells. (e) Genome browser view of AR, MED1, BRD4, and H3K27ac ChIP-Seq data at the FKBP5 locus. The SE region is depicted with a black bar on the bottom right. (f) Increased AR recruitment to the SE in the PCa tumors compared to normal tissues. Box plot showing AR enrichment signal in the enhancer and SE regions in 7 normal and 13 tumor samples. (g) MED1 knockdown blocks AR-mediated transcription. RNA-seq followed by Gene-Set Enrichment Analysis (GSEA) showing negative enrichment of the Hallmark AR gene signature in the MED1 knockdown cells. (h) MED1 phosphorylation upon activation of AR signaling. Cells were stimulated with DHT, and nuclear fractions were treated with or without calf intestine alkaline phosphatase (CIAP) before Phos-tag SDS-PAGE and immunoblotting for MED1. Control immunoblots were done on normal gels with the indicated antibodies. (i) Top, Illustration of the FLAG/HA-tagged wild-type (WT) MED1 and threonine-phosphorylation site T1032A/T1457A double-mutant (DM) MED1. Bottom, Immunoprecipitation of HA-tagged WT MED1, single and double mutant MED1 in LNCaP cells. Whole cell lysates were immunoprecipitated with anti-HA antibody followed by immunoblot analyses using anti-phospho-threonine and anti-AR antibody. (j) Immunoblot analyses showing time dependent increase in p-MED1 (p-T1457 MED1) levels by DHT stimulation. (k) Top, Schematic depicting phosphorylation dependent MED1-AR interaction. Bottom, The LNCaP cells were starved and stimulated with DHT, the nuclear proteins obtained were employed for reciprocal co-immunoprecipitation followed by immunoblotting with the indicated antibodies. (l, m) Tissue microarray analysis of p-MED1 in Benign, PCA (primary), and MET (metastatic) prostate tissues and quantification of their product scores.

Colony formation assays in the enzalutamide resistant PCa cell lines under enzalutamide alone or in combination with 50 nM THZ1 treatment for 14 days followed by staining.

FIG. 10: MED1 phenocopies MED1 and CDK7 knockdown in AR-positive PCa cells. (a) Increased p-MED1 levels in AR-positive PCa cells. Box plot showing normalized p-MED1 intensity quantified from immunoblot shown in FIG. 9*b* for a panel of AR-positive and AR-negative PCa cell lines. (b) Hypersensitivity to THZ1 in AR-positive PCa cells (associated with FIG. 9*c*). PCa cells were cultured in the presence of vehicle or varying concentrations of THZ1 for 12-14 days followed by crystal violet staining, de-staining with glacial acetic acid and absorbance reading @ 590 nm—shown are mean±S.E from 3 independent measurements. (c) THZ1 treatment leads to down-regulation of AR target genes, including ERG, MYC, and PSA, but does not alters the levels of AR and CDK7. Immunoblotting in two AR-positive and two AR-negative cells, with the marked antibodies, 24 h post treatment with DMSO or THZ1. (d) MED1 or CDK7 knockdown in AR-positive PCa cells leads to decreased MED1 phosphorylation and increased apoptosis. Immunoblot analysis for the indicated target proteins in LNCaP, VCaP, PC3 and DU145 cells transfected with siRNA against MED1 or CDK7 or siNT (non-targeting) for 48 h. MED1 and CDK7 knockdown lead to a significant reduction in the levels of AR targets (PSA and ERG) and MYC, and increased expression levels of cleaved PARP (apoptotic marker) with a concomitant reduction in p-MED1 levels (upon CDK7 knockdown) in AR-positive LNCaP and VCaP cells. Though AR-negative DU145 and PC3 cells displayed reduced p-MED1 upon MED1 or CDK7 knockdown, neither an increase in cleaved PARP levels nor a reduction in MYC levels was observed, as seen for AR-positive cells. GAPDH was used as a loading control. (e) Cell proliferation assay after knockdown of indicated genes. 20,000 cells were seeded in 24-well plates (n=3) 48 h post-transfection with indicated siRNAs and counted on days 0, 2, 4, and 6 by countless II FL Cell. Normalized cell numbers are displayed as mean±S.E and THZ1 treatment was used as positive control. (f) Left: Representative images from colony formation assay showing the pronounced effect of MED1 and CDK7 knockdown in AR-positive cells over AR-negative cell lines. The indicated cell lines were transfected with siNT, siMED1 or siCDK7 and cultured for 14 days followed by crystal violet staining, Right: Normalized absorbance of the crystal violet staining shown as mean±S.E. computed for n=6. Significance level was computed using a two-tailed Student's t-test; here *, , *, and **** denote significance levels with p<0.01, p<0.001, 0.0001, and p<0.00001, respectively.

FIG. 11: THZ1 treatment preferentially affects transcription in AR-positive PCa cells. (a) Venn diagram of genes differentially-expressed, up-regulated and down-regulated in VCaP, LNCaP, and DU145 cells grown in standard growth condition and treated with 100 nM THZ1 for 24 h. THZ1 treatment triggers massive gene regulation in VCaP and LNCaP cells, of which 1074 and 810 were commonly up- and down-regulated, respectively, between the two cell lines, while its effect on DU145 cell line was minimal, with only a total of 238 differentially expressed genes. (b) GSEA plot showing the negative enrichment of the msigDB Hallmark Androgen response signature in THZ1 treated LNCaP (top) and VCaP cells (bottom). (c) GSEA network plot of the various msigDB hallmark signatures[3] displaying positive (red) and negative (blue) enrichment, with a significance of FUR q<=0.1, in THZ1 treated DU145 cells. THZ1 treatment in DU145 lead to positive enrichment of several pathways that were negatively enriched upon THZ1 treatment of VCaP and LNCaP cells (see FIG. 9*h*). (d) THZ1 treatment in VCaP cells displayed negative enrichment of the ERG target gene signature. The 194-signature gene-set in the left panel was generated through differential expression analysis of previously published RNA-seq data for shERG knockdown (GEO accession number GSE110657). In our analysis, we only retained genes that showed at least 2-fold down-regulation with a significance of p<=1e-80. Similarly, the 539 gene signature of the right panel was generated from microarray data for siERG knockdown in VCaP cells by Wang et. al. (GEO accession number GSE58975). (e, f) THZ1 affects ERG levels in VCaP cells in a dose and time-dependent manner Immunoblot showing ERG levels in VCaP cells at 12 h post treatment with varying concentrations of THZ1 (top), and at varying time points post treatment with 200 nM THZ1 (bottom). PSA was used as a positive control for AR axis blockade by THZ1 and GAPDH as the loading control.

FIG. 12: Increased stability of MED1 in Enzalutamide refractory prostate cancer cells, and identification of PP2A as a phosphatase involved in MED1 dephosphorylation. (a) Time-course immunoblot analysis of p-MED1, MED1, AR, and MYC in parental and enzalutamide resistant LNCaP derivative treated with 20 µM cycloheximide (translation inhibitor). MED1 displayed a higher stability in the enzalutamide resistant cells (LNCaP ENZA. Res.) as a result of the increased phosphorylated state compared to parental control (see FIG. 9*i*). Increase in AR stability in LNCaP ENZA. Res. cells could be an indirect consequence of its binding to the phosphorylated form of MED1. MYC—a rapidly translated protein was used as a control for cycloheximide treatment. GAPDH served as a loading control. (b) Shown are the normalized band intensities of MED1 (left), AR (center), and MYC (right) for the above blots, determined using ImageJ; respective GAPDH intensity was used as the normalization factor. (c) Tissue microarray analysis of p-MED1, AR, and PP2A-A in enzalutamide refractory prostate tumor samples obtained from the bone (left) and brain (right) in 2 patients. (d) Knockdown of PPP2CA—a catalytic unit of PP2A lead to increase in p-MED1 expression in PCa cells. Immunoblot analysis of PP2A-A (PPP2CA), p-MED1 and MED1 in 2 AR-positive PCa cell lines upon transfection with siNT or siRNA targeting PPP2CA for 72 h. The ratio of p-MED1 to MED1, determined from ImageJ analysis, is indicated. GAPDH was used as a loading control. (e) Quantification of data in FIG. 9*k*. Long term colony formation assays were performed by seeding 25,000-50,000 enzalutamide resistant cells/well in six-well plates and treated with either 20 µM enzalutamide alone or in combination with 50 nM THZ1. After 12 days, VCaP sub-line cells were counted while LAPC4 and LNCaP sub-line cells were fixed with methanol, stained with crystal violet and photographed. For calorimetric assays, the stained wells were treated with 500 µL 10% acetic acid and the absorbance was measured at 590 nm using a spectrophotometer. Absorbance data, normalized with respective enzalutamide levels, displayed the pronounced anti-proliferative effect of THZ1 in enzalutamide resistant cells. Significance levels were computed using a two-tailed independent sample Student's t-test.

FIGS. 13A-13E. THZ1 blocks CRPC growth in vivo. (13A) Schematic illustrating the VCaP CRPC mouse xenograft experimental design. (13B) Castrated mice bearing VCaP CRPC xenograft received vehicle-D5W (n=8) or 10 mg/kg THZ1 (n=8) twice daily for 4 weeks. The percent change in volume for each tumor after 28 days of treatment is shown as a waterfall plot (y axis). (13C) Representative images of H&E, p-MED1, PSA, Cl.Caspase3, and KI-67 immunohistochemistry staining of THZ1 or vehicle treated VCaP CRPC xenograft tumors. (13D) Plasma PSA levels in vehicle and THZ1 treated mice. p-values were computed using two-tailed student's t-test. (13E) Proposed model of the mechanism of action of CDK7 inhibition in AR-addicted CRPC.

Figure 13A:
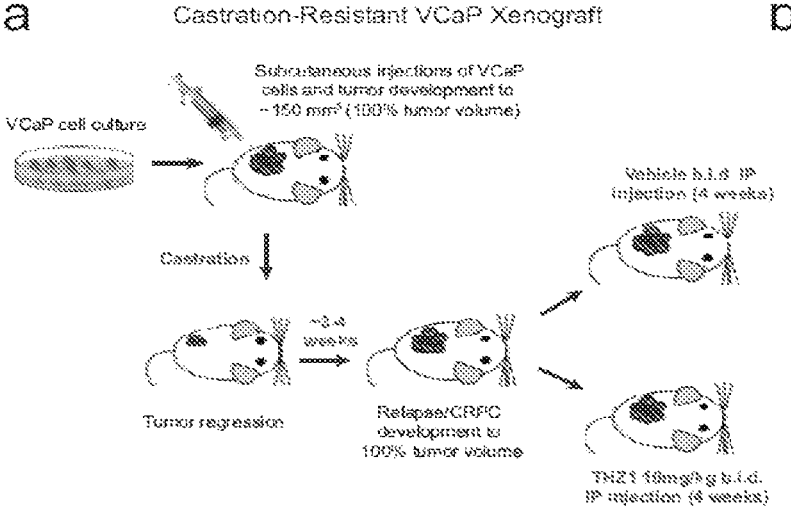
Figure 13B:
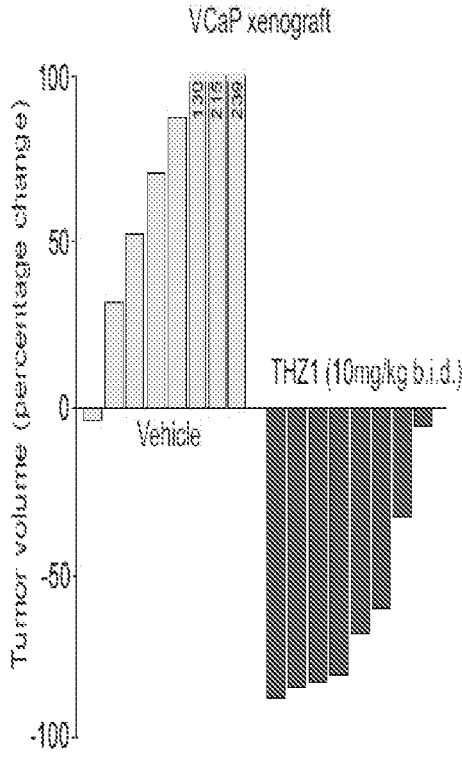
Figure 13C:
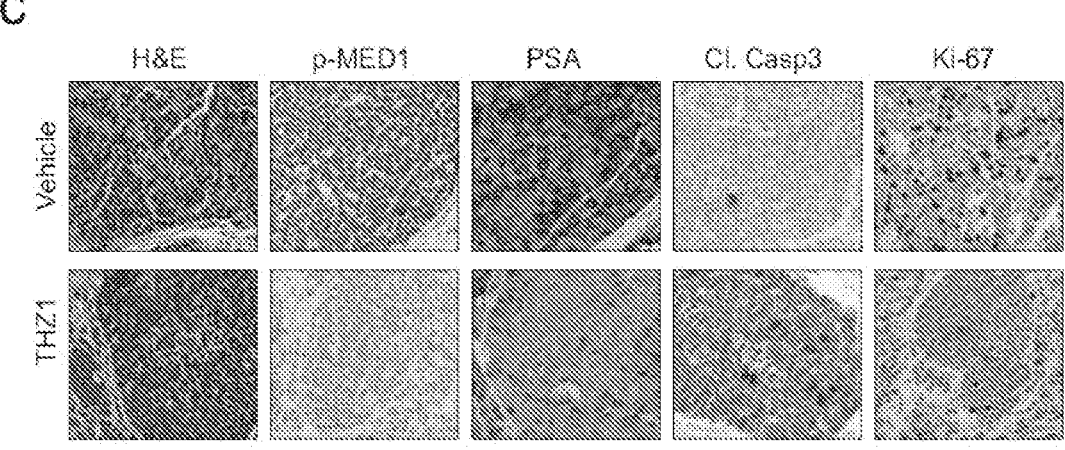
Figures 13D, 13E, 14A, 14B:
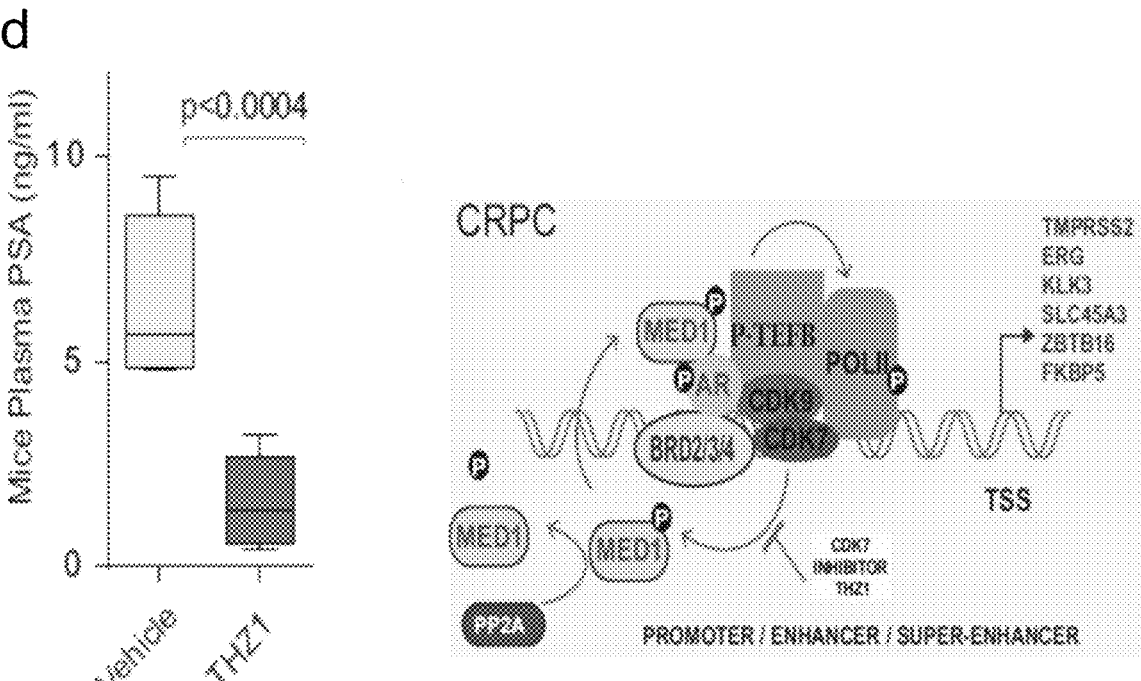
Figure 14C:
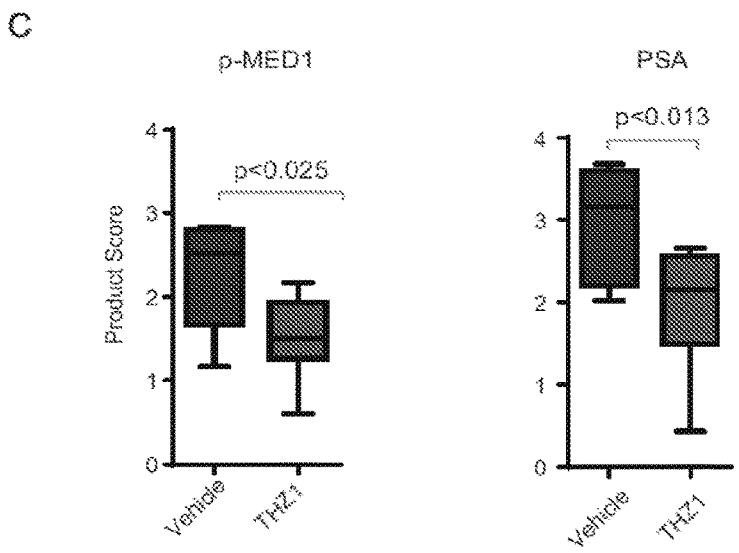

FIGS. 14A-14C: In vivo effects of THZ1 in CRPC VCaP xenograft models. (FIG. 14A) Castrated mice bearing sub-cutaneous VCaP xenograft tumors were randomized and received vehicle-D5W (n=8) or 10 mg/kg THZ1 (n=8) twice daily for 4 weeks. Mean tumor volume±S.E. is shown (for data shown in FIG. 13b). Here, * denotes significance levels less than 0.01. Caliper measurements were taken weekly (FIG. 14B) THZ1 treatment does not affect the animal weight. Mice treated with vehicle or 10 mg/kg THZ1 were weighed at the time of caliper measurements. Mean animal weight±S.D. is shown. (FIG. 14C) Quantifications of p-MED1 and PSA staining in xenograft tumors from vehicle or THZ1 treated animals (for data shown in FIG. 13C). Statistical significance was determined by two-tailed Student's t-test.

Figure 15:
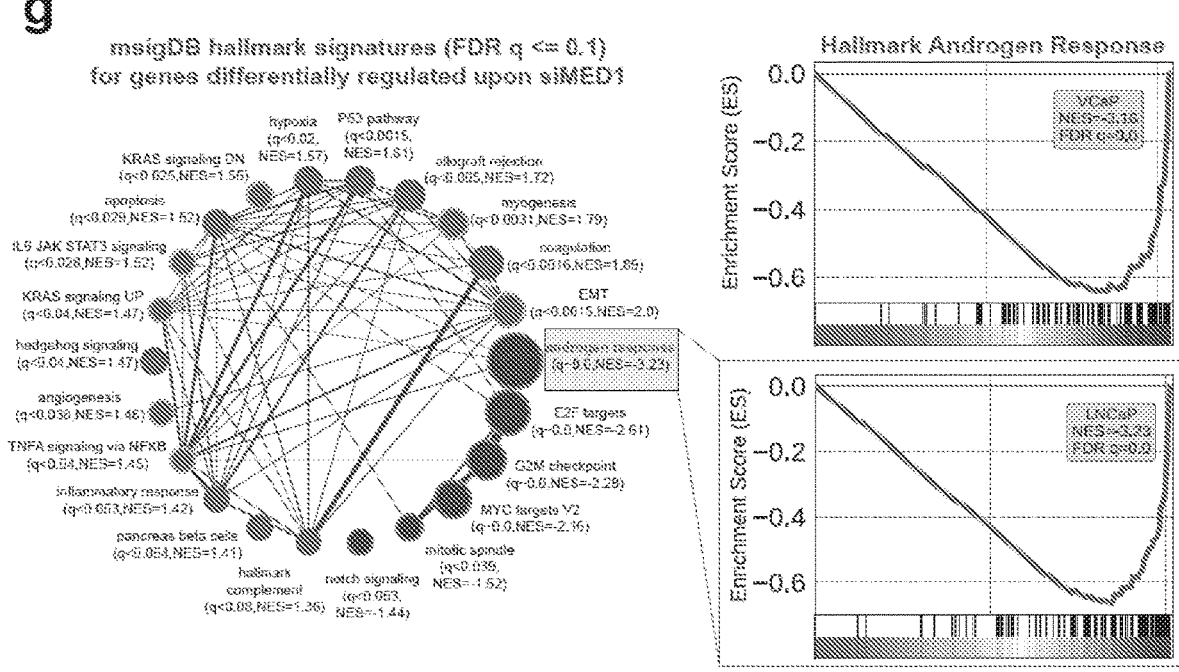

FIG. 15: MED1 knockdown blocks AR-mediated transcription. RNA-seq followed by Gene-Set Enrichment Analysis (GSEA) showing the various hallmark signatures up- (red) and down-regulated (blue) upon MED1 knockdown. The inset shows the negative enrichment of the Hallmark androgen response signature in MED1 knockdown VCaP and LNCaP cells.

Figure 16:
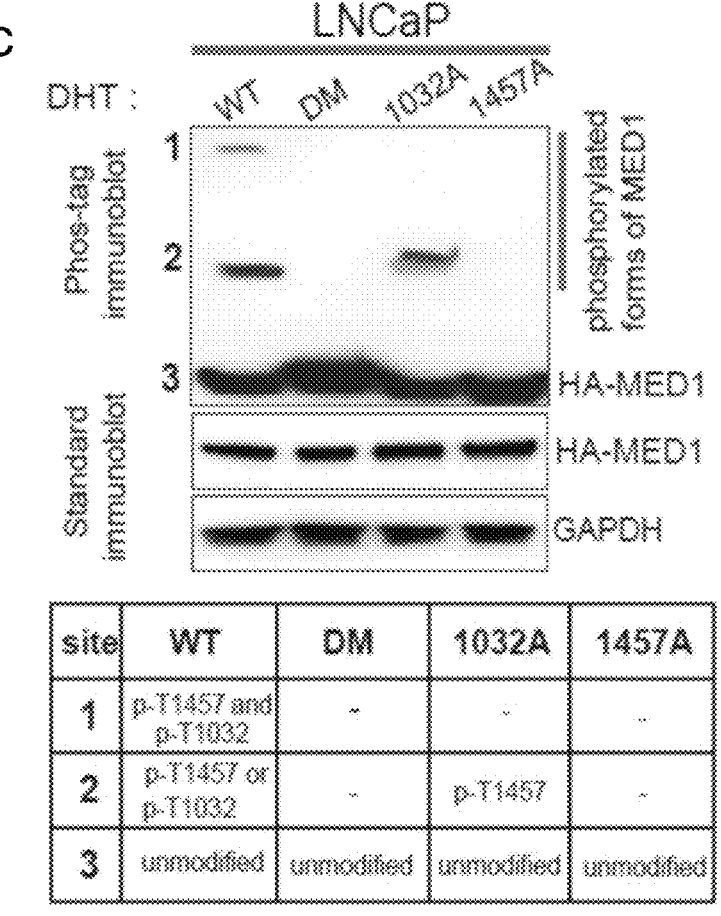

FIG. 16: MED1 undergoes phosphorylation upon androgen stimulation and is recruited to AR bound enhancers and super-enhancers. LNCaP Cells grown in CSS containing media were transfected with HA-tagged wild-type (WT), double mutant (DM), T1032A or T1457A mutant MED1 plasmids for 48 h followed by stimulation with DHT for 12 h. The nuclear proteins were extracted and used for Phos-tag SDS-PAGE and standard immunoblotting with HA antibody. The table below indicates the identity of bands present on the phos-tag blot.

Figure 17:
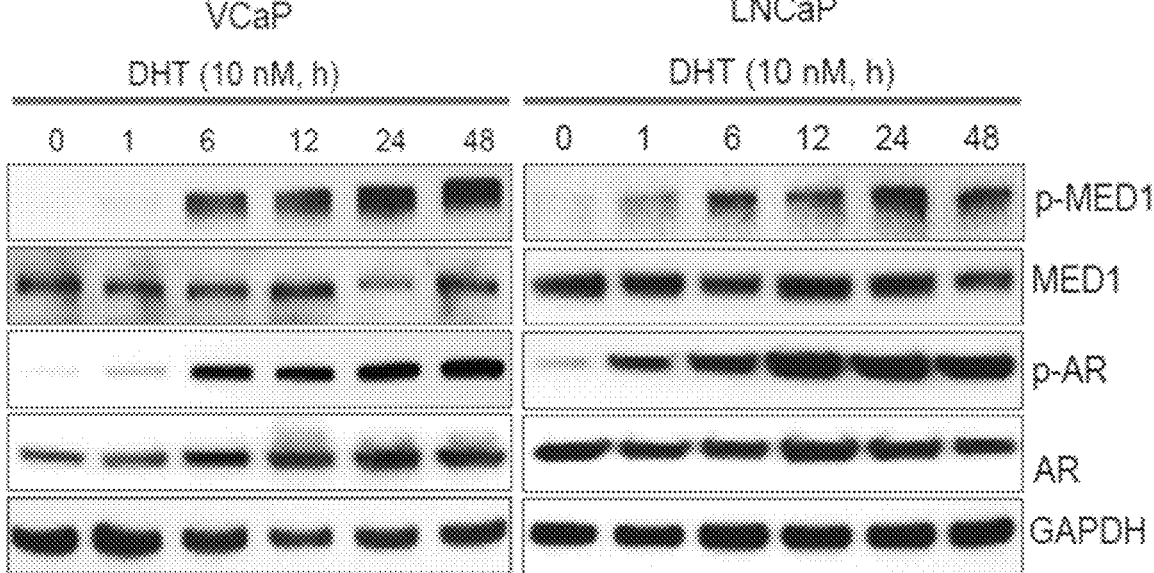

FIG. 17: Immunoblot analyses showing time dependent increase in p-MED1 (p-T1457 MED1) levels by DHT stimulation in VCaP and LNCaP cells.

FIG. 18: Chromatin and soluble nuclear fractions extracted from LNCaP cells grown in CSS containing media for 48 h and subsequent stimulation with DHT alone for 12 h or DHT for 6 h followed by 6 h treatment with ARD-69 (100 nM) were used to probe the indicated proteins. LAMIN and total H3 served as controls for nuclear and chromatin fractions respectively.

FIGS. 19A-19E: CDK7 phosphorylation of MED1 at T1457 is essential for AR-MED1 interactions. (FIG. 19A) CDK7 overexpression rescue CDK7 knockdown effect on MED1 phosphorylation. Total proteins extracted from LNCaP cells transfected with 3'-UTR targeting siRNA against CDK7 along with vector control or HA-CDK7 plasmid for 72 h was subjected to immunoblotting for the indicated target. (FIG. 19B) CDK7 phosphorylate MED1 in vitro. Kinase reaction mixtures containing CAK complex and GST-tagged MED1 protein (aa1391-1490) was prepared as indicated. After 60 min incubation at 30° C., the reaction mixtures were subjected to immunoblot analysis with the indicated antibody. (FIG. 19C) Luminescence based kinase assay showing CDK7 activity on WT vs T1457A mutant peptide and its response to varying concentration of THZ1. (FIG. 19D) Left, T1457D phosphomimic interacts with AR even in the presence of THZ1. Nuclear extracts from LNCaP cells engineered to express HA-tagged MED1 WT or T1457D phosphomimic and treated with 100 nM THZ1 for 12 h were subjected to immunoprecipitation with HA antibody followed by immunoblotting for AR. HA served as input control. Right, schematic depicting the phosphorylation-dependent interaction of MED1 and AR, and the effect of THZ1. (FIG. 19E) T1457D expressing cells demonstrate resistance to THZ1. LNCaP cells were co-transfected with control or siRNA targeting MED1 3'-UTR along with WT, T1457A or T1457D constructs. 48 h post-transfection, equal number of cells were plated and treated with DMSO or 100 nM THZ1 and counted on indicated days (n=3). Also see FIG. 21D.

Figure 20A:
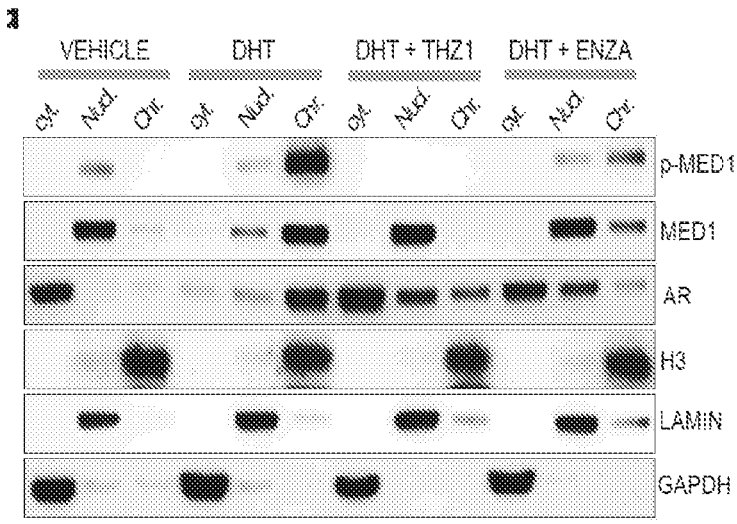
Figure 20B:
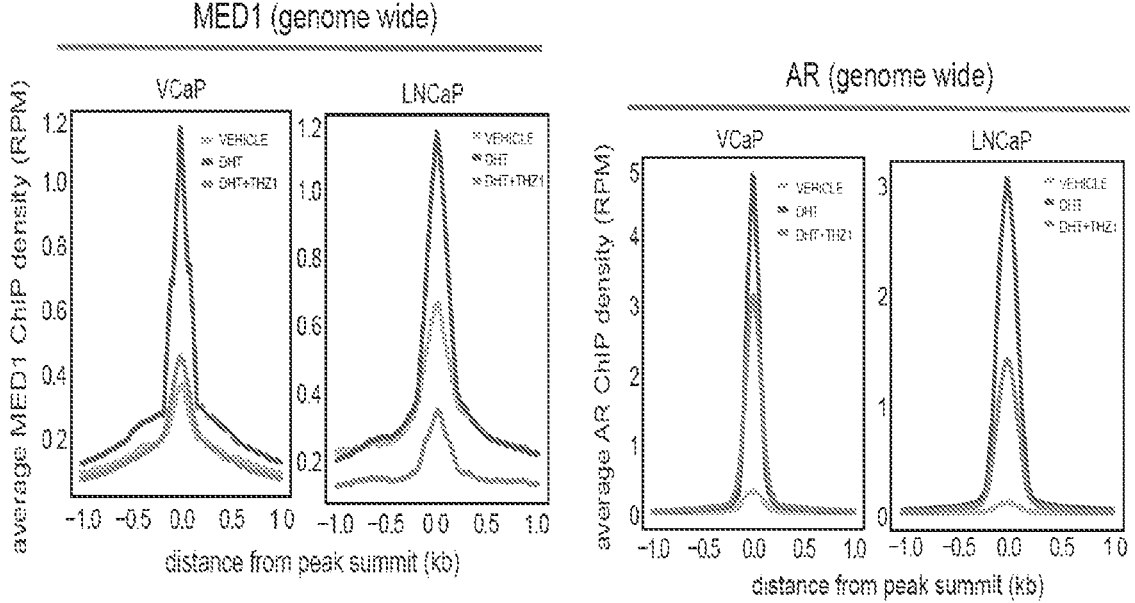
Figure 20C:
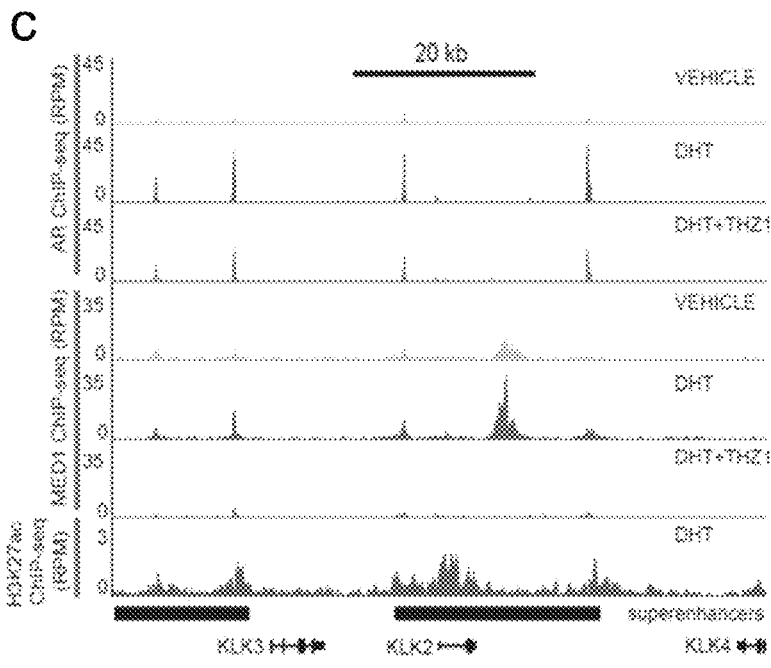

FIGS. 20A-20E: CDK7 inhibition by THZ1 disrupts co-recruitment of MED1 and AR to the chromatin. (FIG. 20A) Immunoblot analysis demonstrating the loss of chromatin bound MED1 (p-MED1) upon THZ1 treatment. Chromatin, nuclear and cytoplasmic fractions from LNCaP cells grown in CSS containing media for 3-days following stimulation with DHT in the absence/presence of 100 nM THZ1 for 6 h were used to probe the indicated proteins. Enzalutamide at 5 μM was used as a direct anti-AR. (FIG. 20B) Genome-wide averaged MED1 and AR ChIP-seq enrichment in VCaP and LNCaP cells grown as in (FIG. 20A). (FIG. 20C) Genome browser tracks of AR, MED1, and H3K27ac binding at the KLK2, KLK3 and KLK4 locus in the indicated condition for VCaP. The super-enhancers (SEs) associated with this region are displayed as black bars at the bottom. (FIG. 20D) MED1 is recruited in a ligand-dependent manner to AR+MED1+H3K27ac regions. Box plots showing MED1 densities (RPM) at AR co-bound and the AR-devoid enhancers and SEs in vehicle, DHT and DHT+ THZ1 treated samples. (FIG. 20E) Integrative analysis of RNA-seq and ChIP-seq shows majority of AR target genes associate with AR+MED1 occupied enhancers and SE. (Top) Venn diagram showing 128 genes commonly upregulated upon DHT treatment in VCaP and LNCaP cells. (Bottom) Each of the 128 genes were associated with enhancers and SE regions described in (FIG. 20D) and the change in their expression under different treatment condition is shown as a violin plot. The significance values shown in panels (FIG. 20D) and (FIG. 20E) were computed using a two-tailed Student's t-test.

Figure 21B:
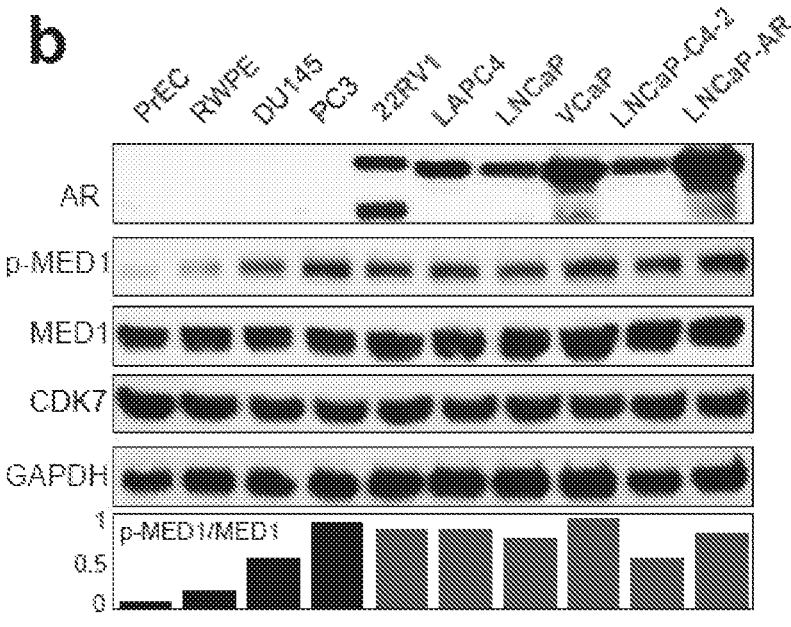
Figure 21C:
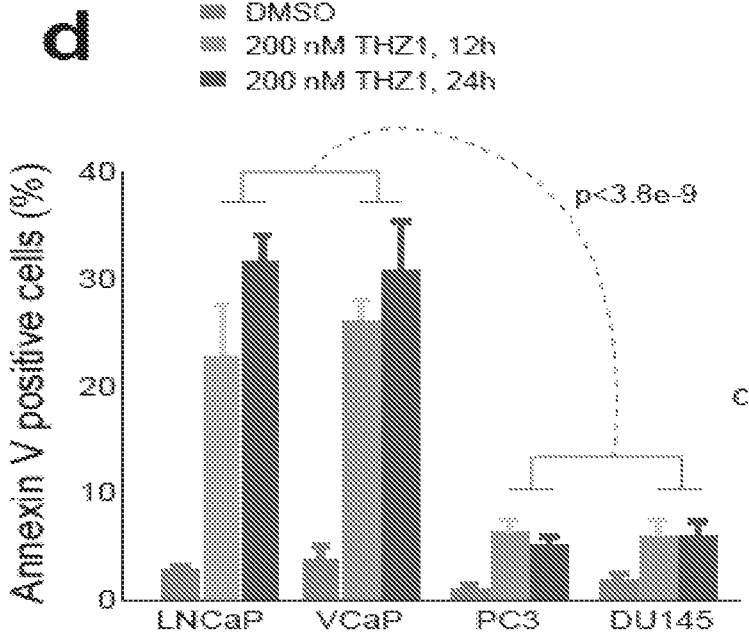

FIGS. 21A-21C: Prostate cancer cells with active AR-signaling are sensitive to CDK7 inhibition. (FIG. 21A) GI50 for THZ1 in a panel of eight PCa cell lines is shown alongside their site of origin, AR status, AR dysregulation, and CDK7 expression. (FIG. 21B) Immunoblot analysis of AR, p-MED1, MED1, CDK7 in six AR positive and four AR negative PCa cell lines, GAPDH was used as the loading control. (FIG. 21C) Annexin V-FITC staining showing percentage of apoptotic cells upon THZ1 treatment. Statistical significance was determined by two-tailed Student's t-test.

Figure 22A:
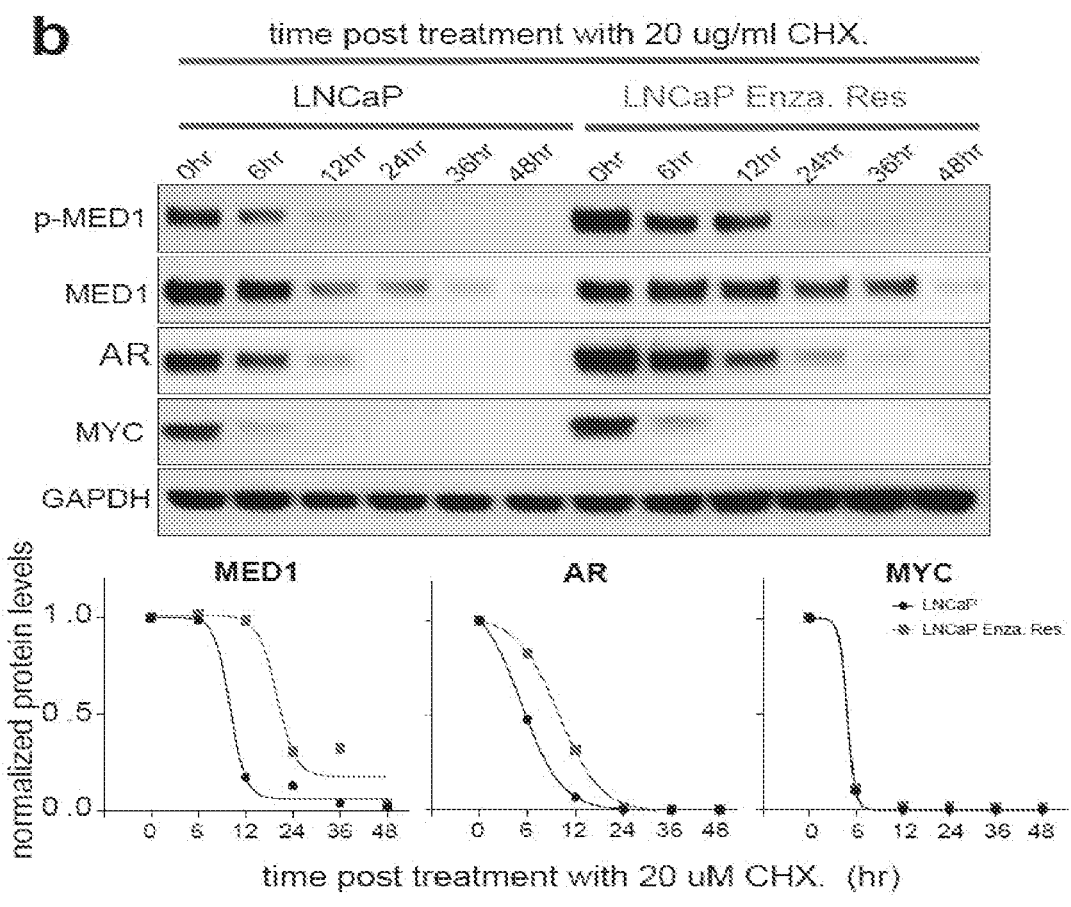
Figure 22B:
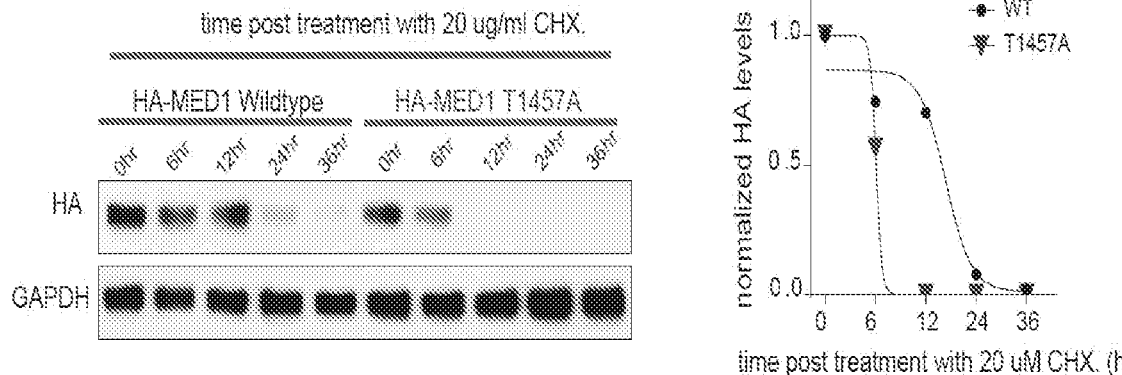
Figure 22C:
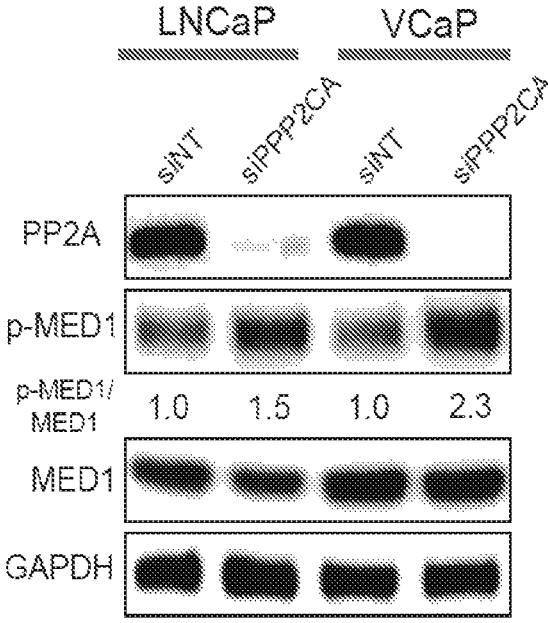

FIGS. 22A-22C: Increased p-MED1 with a concomitant reduction in PP2A and sensitivity to THZ1 in enzalutamide resistant PCa cells. (FIG. 22A) MED1 demonstrates increased stability in enzalutamide resistant cells. Top panel, immunoblot analysis of p-MED1, MED1, AR, and MYC in parental and enzalutamide resistant LNCaP derivative treated with 20 ug/ml cycloheximide as indicated. MYC—a rapidly translated and highly labile protein was used as a control for cycloheximide treatment. GAPDH served as a loading control. Bottom panel, graph showing normalized band intensities determined using ImageJ (FIG. 22B) T1457A mutation decreases MED1 stability. Left, Protein extracts from LNCaP cells transfected with HA-tagged WT or phospho-dead T1457A mutant and treated with cycloheximide for varying time-points were subjected to immunoblotting with HA antibody. Right, graph showing GAPDH normalized band intensities. (FIG. 22C)) Knockdown of PPP2CA—a catalytic unit of PP2A led to increase in p-MED1 expression in PCa cells Immunoblot analysis of PP2A (PPP2CA), p-MED1 and MED1 in LNCaP and VCaP cells 72 h post-transfection with siNT or siRNA targeting PPP2CA. The ratio of p-MED1 to MED1 is indicated. GAPDH was used as a loading control.

Figure 23A:
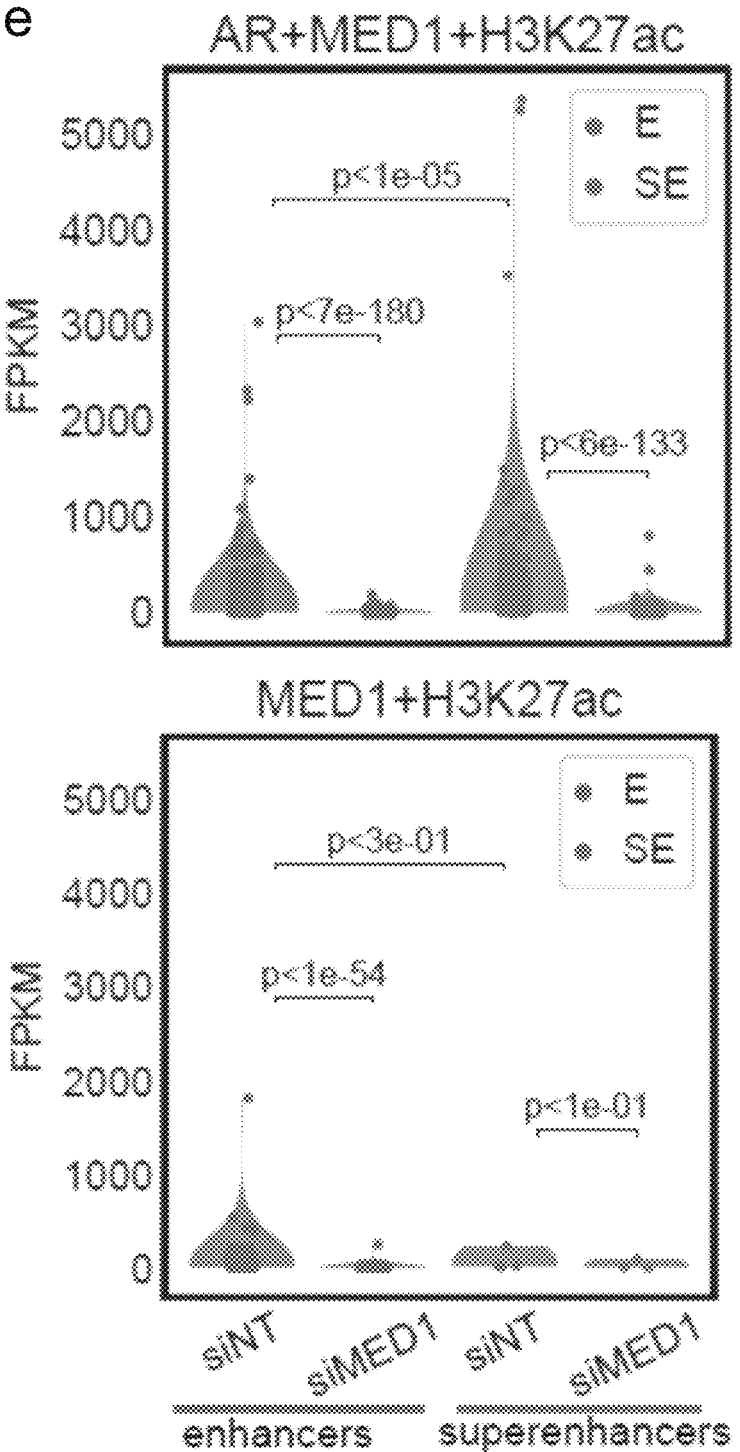

FIGS. 23A-23B: MED1 knockdown blocks AR-mediated transcription and growth associated pathways in PCa cells. (FIG. 23A) RNA-seq FPKM values for genes associated with enhancers and superenhancers, upon siMED1 knockdown in VCaP cells. Top and bottom panels correspond to enhancers and superenhancers occupied by AR+MED1 and MEDI alone, respectively. (FIG. 23B) GSEA network plot of the various msigDB hallmark signatures (3) displaying positive (red) and negative (blue) enrichment, with a significance of FDR q<=0.1, in siMED1 knockdown VCaP cells. Here, the yellow and green outlines represent signatures enriched positively and negatively, respectively, in both cell lines. MED1 knockdown leads to negative enrichment of the hallmark androgen response genes (indicated in bold) in VCaP and LNCaP cells.

FIGS. 24A-24E: AR activation leads to phosphorylation of Thr1457 on MED1. (FIG. 24A) LNCaP Cells were transfected with HA-tagged wild-type (WT), T1032A and T1457A double mutant (DM), and T1032A or T1457A single mutant MED1 plasmids for 72 h. The proteins were extracted and used for immunoblotting with HA antibody. Validation of p-T1457 MED1 specific antibody Immunoprecipitation of HA-tagged WT, single and double mutant MED1 followed by immunoblotting with the p-T1457 specific antibody was carried out in LNCaP cells, with HA as the IP control. p-1457 MED1 signal was completely lost in both DM and 1457A mutants but remained intact in 1032A mutant which clearly establishes the high specificity of p-T1457 MED1 antibody for p-MED1. (FIG. 24B) Immunoblot showing the effect of AR degradation on p-MED1 levels. LNCaP cells were treated with 100 nM of AR degrader PROTAC ARD-69 for the indicated time points followed by immunoblotting analysis for AR, MED1, and p-MED1 using GAPDH as the loading control. The normalized band intensities for AR and p-MED1 is shown. (FIG. 24C) MED1 phosphorylation is strongly dependent on endogenous levels of AR. Blots show the ligand-dependent increase of p-MED1 levels in AR expressing LNCaP cells and the lack of such response in AR knockout LNCaP cells (LNCaP AR KO). Quantified levels of p-MED 1 are shown. (FIG. 24D) Immunohistochemistry validation for pT1457 specific antibody. Immunohistochemistry analysis using the p-T1457 MED1 antibody in LNCaP cells grown in CSS media for 3 days followed by vehicle or DHT stimulation for 12 h. The cells were harvested and resuspended in 10% formaldehyde for 10 min, the pellets were then obtained through centrifugation, fixed in 10% formaldehyde overnight at 4° C. followed by processing for immunohistochemistry. (FIG. 24E) No antibody control for the tissue microarray shown in FIG. 1I.

FIGS. 25A-25D: CDK7 phosphorylates MEDI. at T1457. (FIG. 25A) LNCaP cells were either transfected with siNT/siCDK7 (siRNA1 and siRNA2 (individual siRNA's), pool (smart pool of 4 siRNA's)) or treated with 100 nM of THZ1/THZ1-R for 12 h followed by immunoblot analysis with the mentioned antibodies. Treatment with THZ1-R, a non-cysteine reactive analog of THZ1, does not affect MEDI phosphorylation. (FIG. 25B) ERK and AKT knockdown in mitogen stimulated condition led to only a partial reduction in p-MED1 levels, compared to CDK7 knockdown. LNCaP cells were transfected with siNT or siAKT/siERK/siCDK7 and serum starved for 72 h followed by stimulation with 100 ng/ml EGF for 30 min. Immunoblotting analysis was used to probe the indicated proteins. Normalized ratio of p-MED1/MED1 is shown alongside, and GAPDH was used as the loading control. (FIG. 25C-FIG. 25D) THZ1 blocks MEDI phosphorylation in a dose and time-dependent manner. The indicated cell lines were grown in standard growth conditions. For dose-dependent studies cells were treated with the indicated doses of THZ1 for 12 h followed by immunoblotting with the indicated antibodies. For time-course studies, the cells were treated with 200 nM THZ1 at the indicated time points followed by immunoblotting for the indicated targets.

FIGS. 26A-26D: MED1-T1457D phosphomimic over-expressing cells resist THZ1 treatment: (FIG. 26A) LNCaP cells transfected with HA-tagged MED1-wildtype/T1457A/T1457D constructs were starved in CSS media for 2-days following stimulation with 10 nM DHT for 12 h in the presence of DMSO or 200 nM THZ1. Nuclear and chromatin fractions were isolated from the treated cells and employed for immunoblotting to probe for the indicated proteins. LAMIN and H3 served as control for soluble nuclear and chromatin fractions, respectively. (FIG. 26B) T1457D phosphomimic restored AR target gene expression even in the presence of THZ1 treatment. LNCaP cells were co-transfected with siMED1 (on target 3'UTR) and/or MED1-wildtype, T1457A-dead mutant or T1457D phosphomimic as indicated. After transfection the cells were starved for 2-days in CSS media followed by DHT stimulation and 200 nM THZ 1 treatment for 12 h. Total RNA extracted was used for qRT-PCR analysis. Fold change in the expression of AR-target genes is shown (n=3, mean±SD). The immunoblots below is a validation endogenous MED1 knockdown and ectopic-expression of HA-MED1 and its mutants. PSA served as a positive control for DHT stimulation. (FIG. 26C) Immunoblot validation for the MED1 rescue proliferation assay shown in FIG. 19E. The same set of conditions used in (FIG. 26B) were followed but in regular medium conditions. (FIG. 26D) T1457A over-expression negatively affects the proliferation of LNCaP cells. LNCaP cells were transfected with HA-tagged wildtype-, T1457A- or T1457D-MED1 constructs. The cell number was counted using a Beckman Coulter cell counter every two days until day 6. The immunoblot shown below confirms the over-expression of the various HA-tagged MED 1 constructs.

FIGS. 27A-27E: CDK7 inhibition blocks MEM chromatin recruitment and AR mediated transcription. (FIG. 27A) AR and MED1 are co-recruited to the chromatin upon DHT-stimulation in VCaP cells. Venn diagram shows the overlap between AR and MED1 enrichment peaks in DHT-stimulatd VCaP cells. Heatmap shows the AR and MED 1 ChIP-seq density at the AR and MED1 overlapping regions in vehicle, DHT, and DHT+THZ1 treatment conditions. (FIG. 27B) Distribution of AR density in the enhancers and superenhancer regions associated with AR+MEDI+H3K27ac regions (top) and AR+H3K27ac regions (bottom) in vehicle, DHT, and DHT+THZI treated VCaP cells. (FIG. 27C) Left: Superenhancer plot showing the 752 superenhancers and 33952 enhancers in H3K27ac ChIP-Seq in LNCaP cells, Middle: Pie chart showing the overlap of AR and MED1 enrichment peaks with the H3K27ac enhancers and superenhancers, and Right: MED1 and AR tag density in the 223 AR+MEDI+H3K27ac enhancers and 117 AR+MED1+H3K27ac superenhancers regions, showing increased AR and MED1 binding upon DHT treatment and their reversal upon treatment with 200 nM THZ1 for 6 h. (FIG. 27D) Heatmap shows AR and MED1 ChIP-seq density at 410 overlapping AR and MED1 peaks in DHT-stimulated LNCaP cells. (FIG. 27E) Genome browser tracks of the KLK locus in LNCaP cells in the indicated conditions.

Figure 28A:
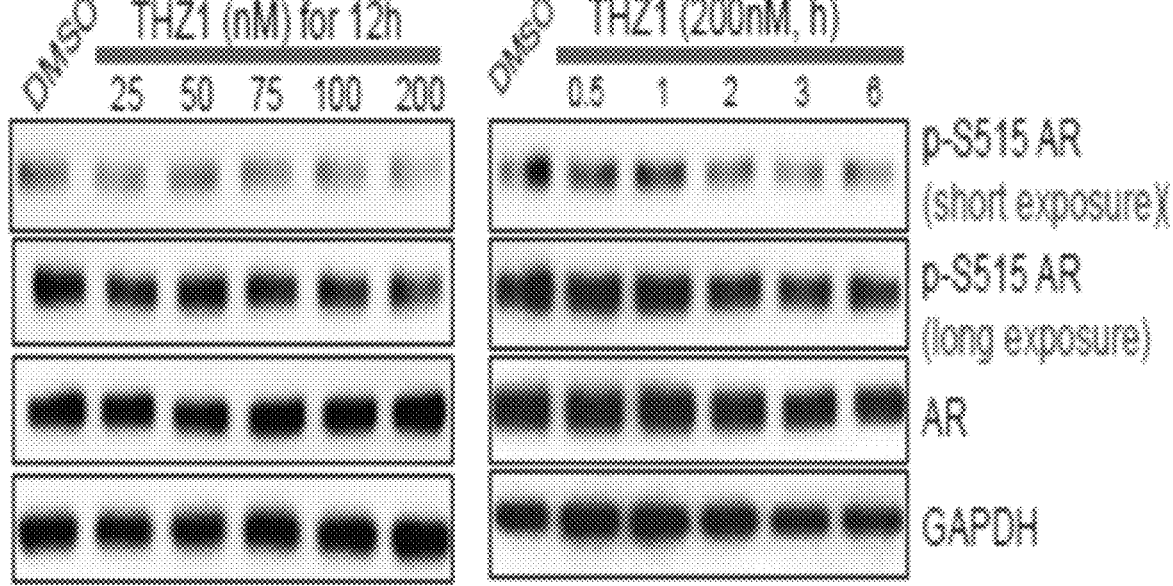
Figure 28B:
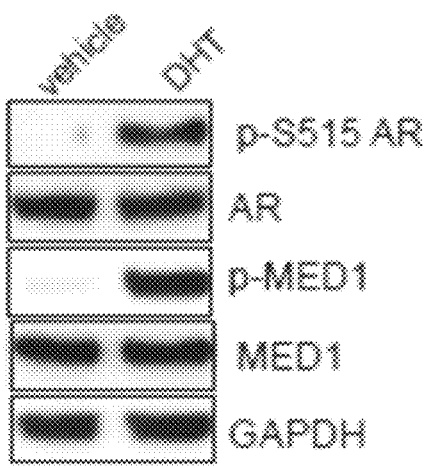

FIGS. 28A-28B: THZ1 treatment preferentially affects transcription in AR-positive PCa cells. (FIG. 28A) THZ1 treatment does not affect AR (Ser-515) phosphorylation. LNCaP cells were grown in normal media and treated with THZ1 (200 nM THZ1 for time-dependent studies, and at the indicated concentrations for 12 h for dose-dependent studies) were used for immunoblotting with the AR pS515 specific antibody. Total AR and GAPDH served as controls. (FIG. 28B) Increase in p-S515 levels upon DHT stimulation was used to validate p-S515 antibody. LNCaP cells grown in CSS media for 3 days were stimulated with 10 nM DHT for 24 h. Total lysate used for immunoblot analysis with AR p-S515 antibody. Increase in p-MED 1 upon DHT stimulation served as positive control. GAPDH served as loading control.

Figure 29A:
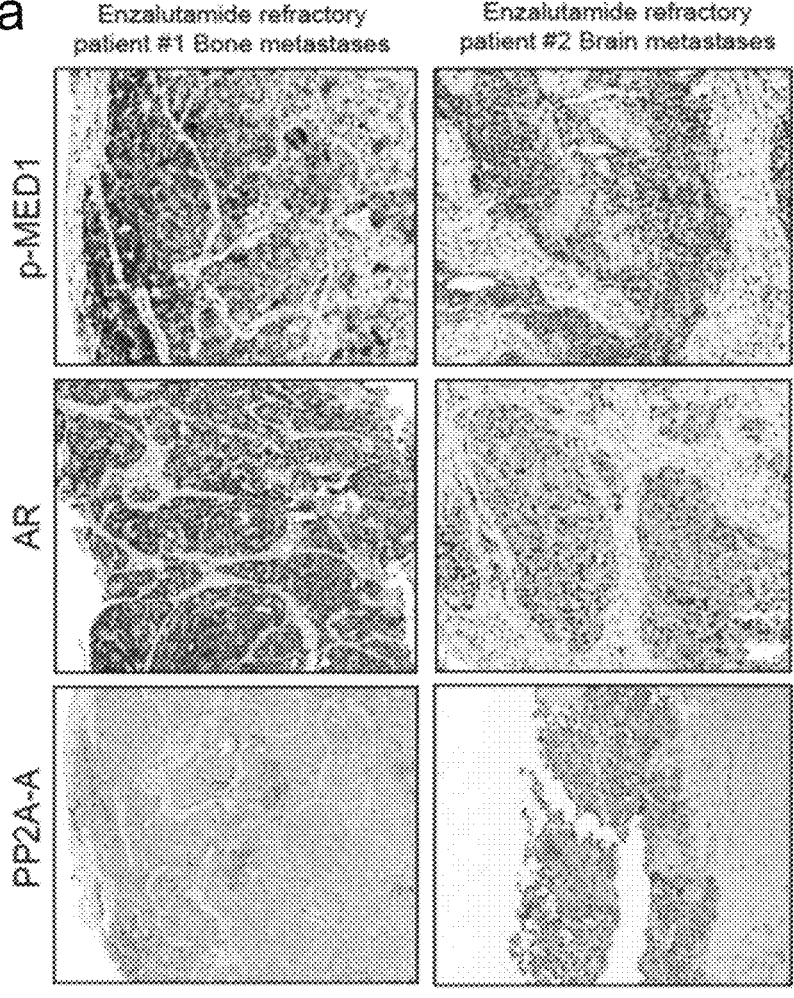
Figure 29B:
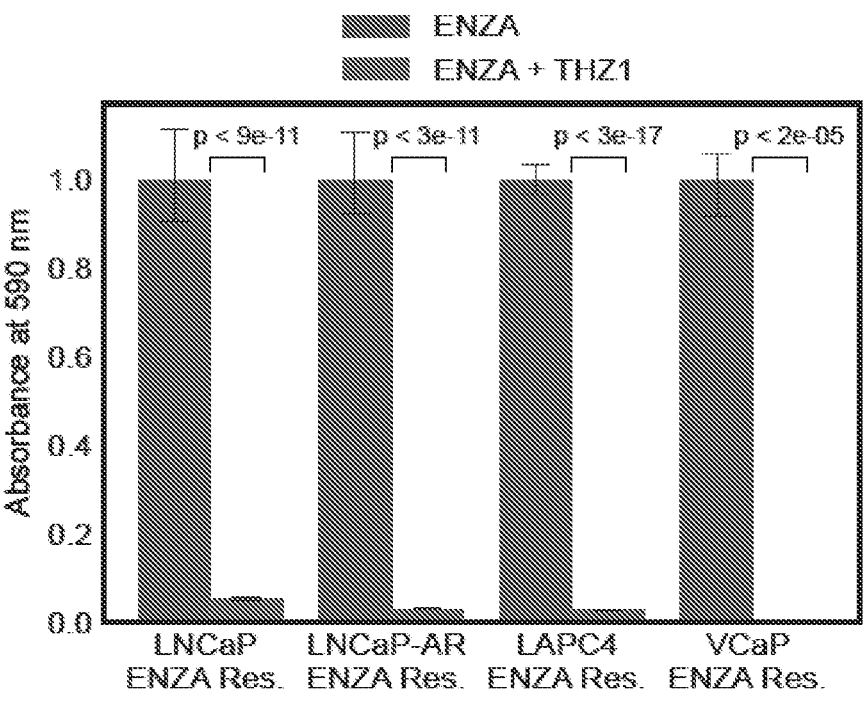
Figure 30A:
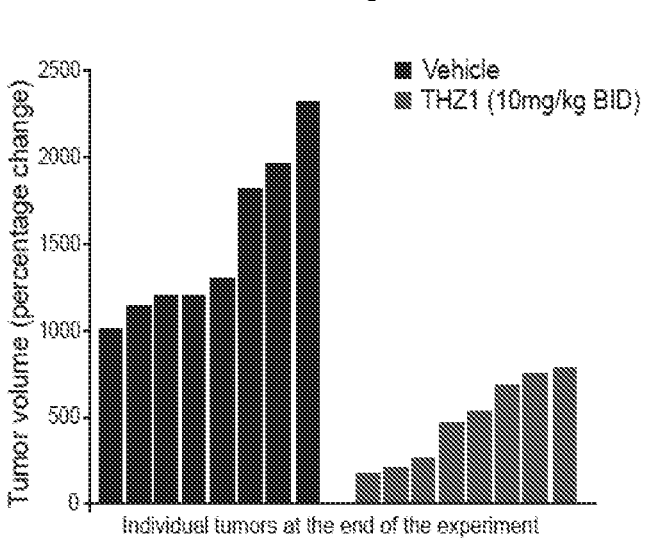
Figure 30B:
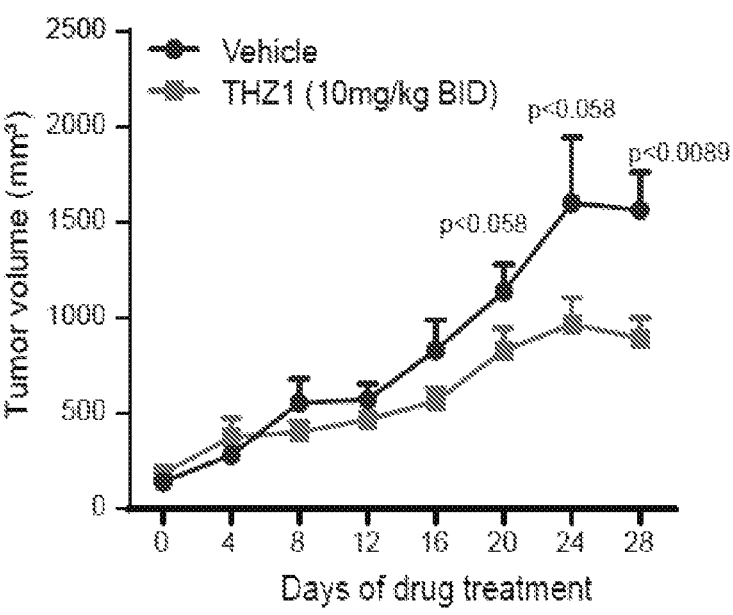
Figure 30C:
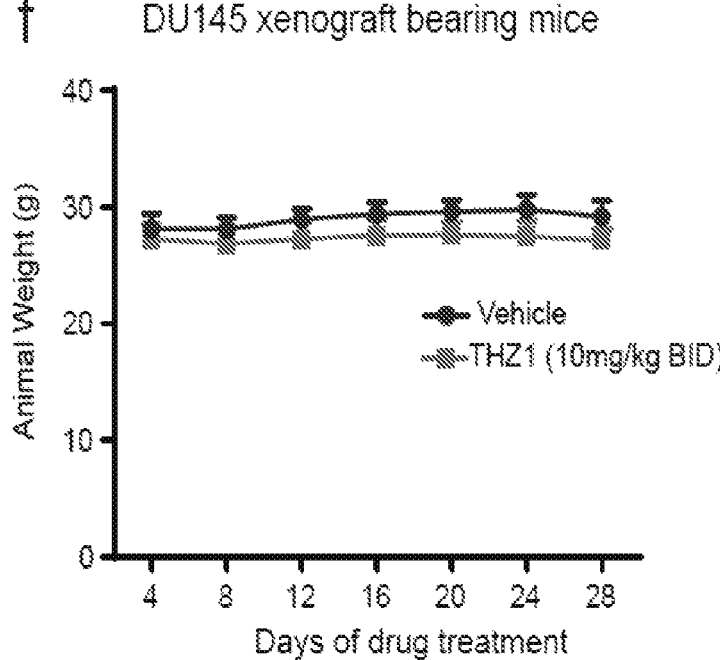
Figure 30D:
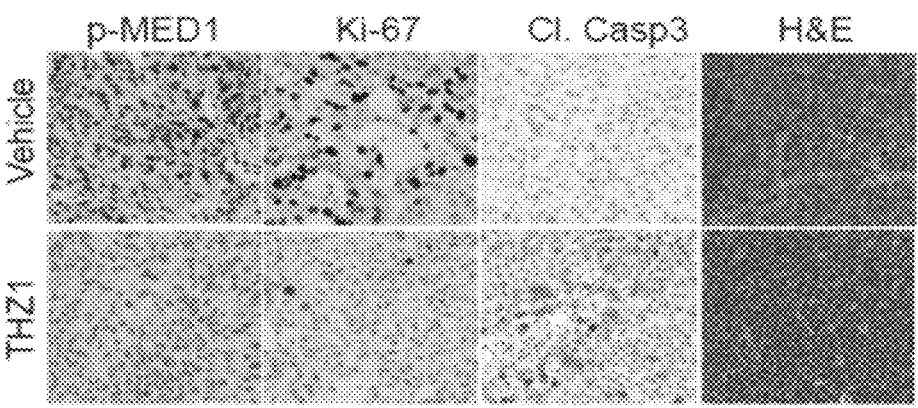

FIGS. 29A-29B: Anti-proliferative effect of THZ1 in enzalutamide resistant cells. (FIG. 29A) Tissue microarray analysis of p-MED1, AR, and PP2A-A in enzalutamide refractory prostate tumor samples obtained from the bone (left) and brain (right) in 2 patients. (FIG. 29B) Quantification of data in FIG. 9K. Long term colony formation assays were performed by seeding 25,000-50,000 enzalutamide resistant cells/well in six-well plates and treated with either 20 AM enzalutamide alone or in combination with 50 nM THZ1. After 12 days, VCaP sub-line cells were counted while LAPC4 and LNCaP sub-line cells were fixed with methanol, stained with crystal violet and photographed. For calorimetric assays, the stained wells were treated with 500 10% acetic acid and the absorbance was measured at 590 nm using a spectrophotometer. Absorbance data, normalized with respective enzalutamide levels, displayed the pronounced anti-proliferative effect of THZ1 in enzalutamide resistant cells. Significance levels were computed using a two-tailed independent sample Student's t-test.

FIGS. 30A-30D: In vivo effects of THZ1 in CRPC VCaP and DU145 xenograft models. (FIG. 30A) Castrated mice bearing DU145 CRPC xenograft received vehicle-D5W (n=8) or 10 mg/kg THZ1 (n=8) twice daily for 4 weeks. The percent change in volume for each tumor after 28 days of treatment, shown as a waterfall plot (y axis), depicts reduction in the tumor volume upon THZ1 treatment. (FIG. 30B) Mean tumor volume±S.E. for the DU145 xenograft. (FIG. 30C) Mean weight±S.E. of mice bearing DU145 xenograft. (FIG. 30D) Representative images of p-MED 1, H&E, C1.Caspase-3, and KI-67 immunohistochemistry staining of THZ1 or vehicle treated DU145 xenograft tumors.

Figure 31A:
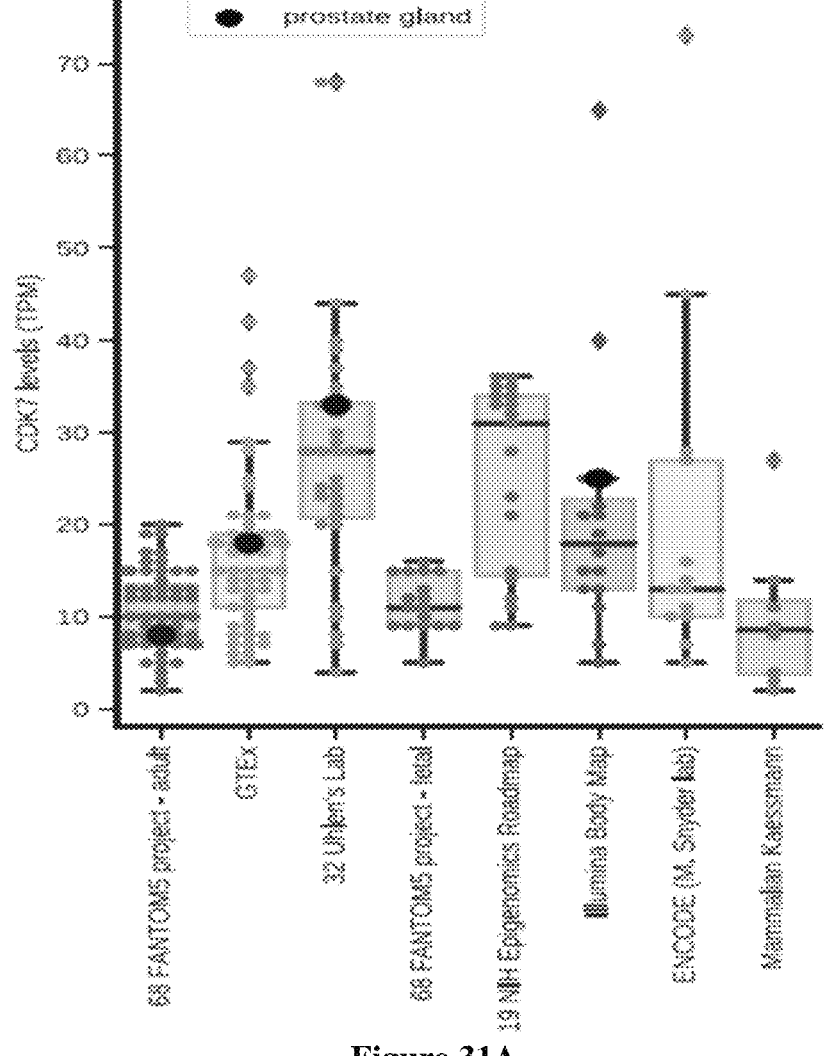
Figure 31B:
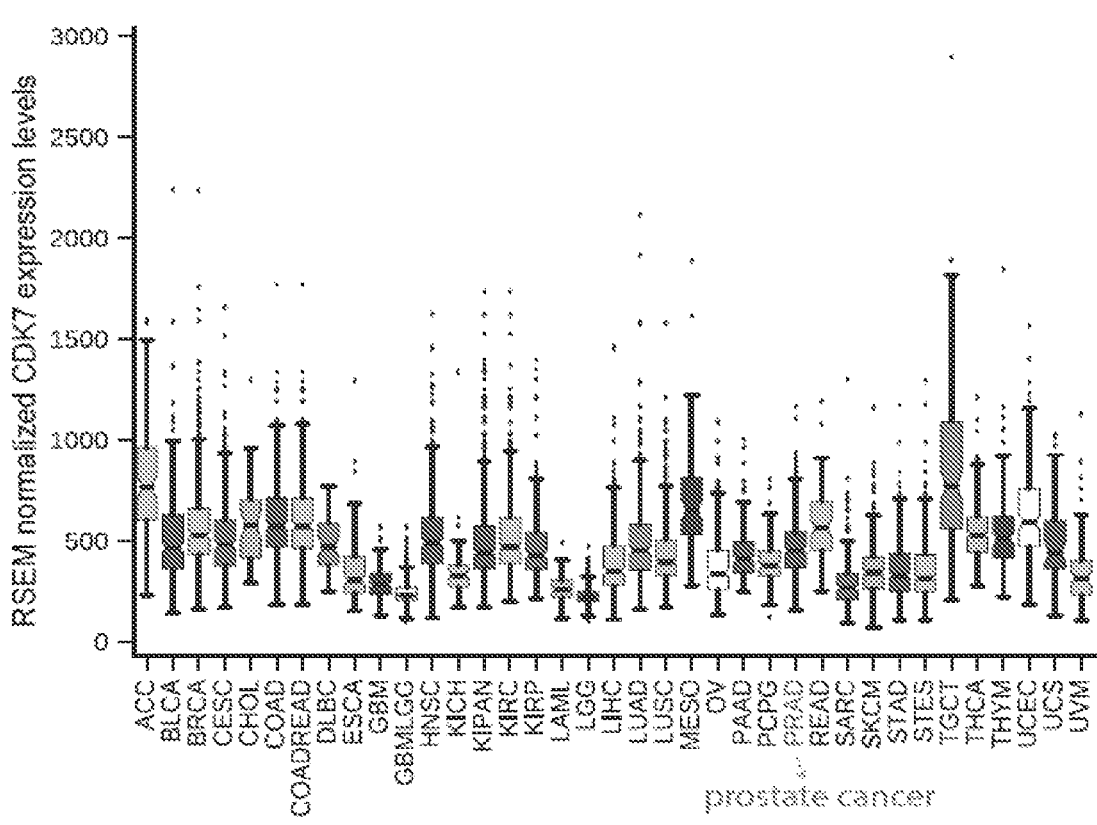
Figure 31C:
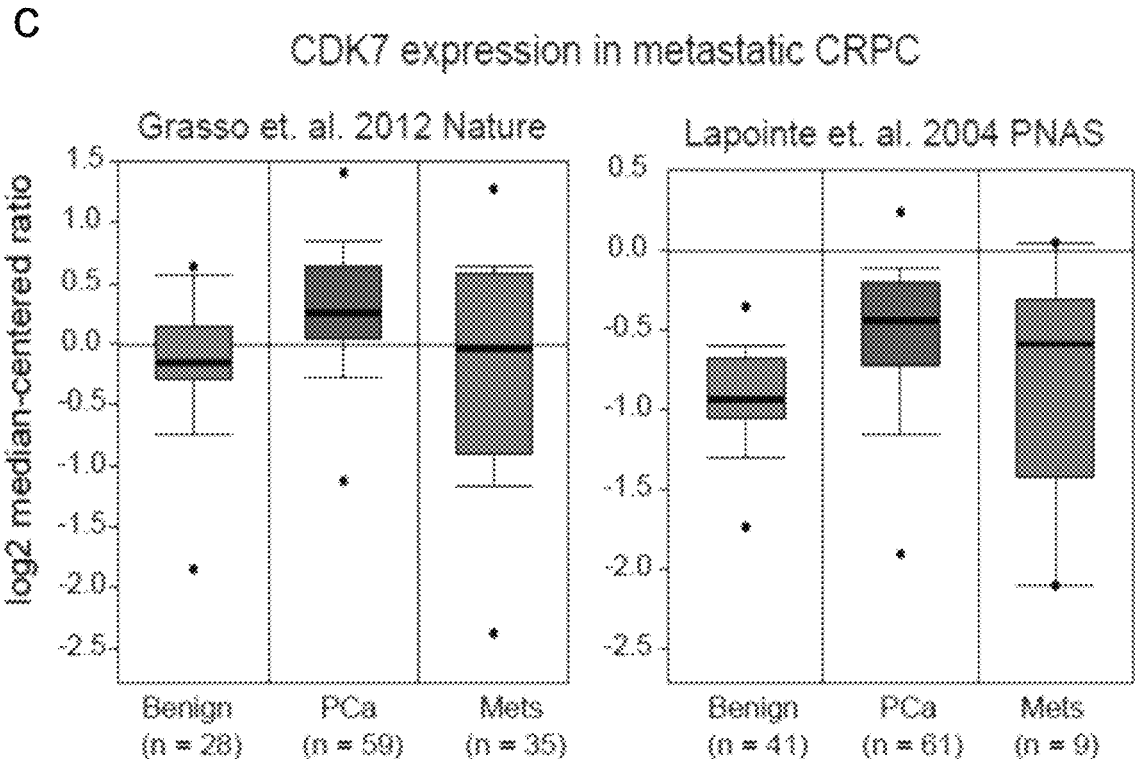

FIGS. 31A-31C: Ubiquitously expressed CDK7 is not significantly altered in mCRPC. We analyzed the expression of CDK7 reported in various bioinformatics databases to determine if CDK7 expression is altered upon disease progression. Our analysis showed no significant differential regulation of CDK7 across disease conditions. (FIG. 31A) CDK7 expression in various human organs were obtained from expression atlas (www.ebi.ac.uk/gxa/home) (www.ebi-.ac.uk/gxa/genes/ensg00000134058?bs=%7B %22 homo%20sapiens%22%3A% 5B %22ORGANISMPART%22%5D%7D&ds=%7B %22kingdom%22%3A%5B %22 animals% 22%5D%7D#baseline) and its distribution in the organs (shown as scatter points) in various studies are shown as box plots. CDK7 expression in the prostate gland is shown as black filled circle. (FIG. 31B) RSEM normalized TCGA expression data for 37 primary tumors were obtained from GDAC (https://gdac.broadinstitute.org/) and CDK7 expression across the tumors are shown as box plots. (FIG. 31C) Comparison of the log 2 normalized expression of CDK7 in benign, primary, mCRPC tumors reported in Grasso et. al. (10) and Lapointe et. al. (11). Plots were generated using Oncomine (oncomine.org).

DETAILED DESCRIPTION OF THE INVENTION

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure, the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from one particular and/or to the other particular value.

Similarly, when values are expressed as approximations, by use of the antecedent "about," it is understood that the particular value forms another embodiment. All ranges are inclusive and combinable. In the context of the present disclosure, by "about" a certain amount it is meant that the amount is within ±20% of the stated amount, or preferably within ±10% of the stated amount, or more preferably within ±5% of the stated amount.

As used herein, the terms "treat," "treatment," or "therapy" (as well as different forms thereof) refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Those in need of treatment include those already with the disease or condition as well as those prone to having the disease or condition or those in which the disease or condition is to be prevented.

As used herein, the terms "component," "composition," "formulation,", "composition of compounds," "compound,"

"drug," "agent", "pharmacologically active agent," "active agent," "therapeutic," "therapy," "treatment," or "medicament," are used interchangeably herein, as context dictates, to refer to a compound or compounds or composition of matter which, when administered to a subject (human or animal) induces a desired pharmacological and/or physiologic effect by local and/or systemic action. A personalized composition or method refers to a product or use of the product in a regimen tailored or individualized to meet specific needs identified or contemplated in the subject.

The terms "subject," "individual," and "patient" are used interchangeably herein, and refer to an animal, for example a human, to whom treatment with a composition or formulation in accordance with the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys. The compositions described herein can be used to treat any suitable mammal, including primates, such as monkeys and humans, horses, cows, cats, dogs, rabbits, and rodents such as rats and mice. In one embodiment, the mammal to be treated is human. The human can be any human of any age. In an embodiment, the human is an adult. In another embodiment, the human is a child. The human can be male, female, pregnant, middle-aged, adolescent, or elderly. According to any of the methods of the present invention and in one embodiment, the subject is human. In another embodiment, the subject is a non-human primate. In another embodiment, the subject is murine, which in one embodiment is a mouse, and, in another embodiment is a rat. In another embodiment, the subject is canine, feline, bovine, equine, laprine or porcine. In another embodiment, the subject is mammalian.

Conditions and disorders in a subject for which a particular drug, compound, composition, formulation (or combination thereof) is said herein to be "indicated" are not restricted to conditions and disorders for which that drug or compound or composition or formulation has been expressly approved by a regulatory authority, but also include other conditions and disorders known or reasonably believed by a physician or other health or nutritional practitioner to be amenable to treatment with that drug or compound or composition or formulation or combination thereof.

As used herein, reducing or decreasing the size of a tumor can include reducing size as measured by volume, weight, cell number, decrease in number of living cells, increase in necrosis, or any other method for measuring size, or slowing or halting of, or reduction in growth. In an embodiment, volume of tumor size is calculated as length×width×width× 0.52. In an embodiment, tumor size is decreased by between about 1% and about 100%. In an embodiment, tumor size is decreased by between about 25% and about 50%. In an embodiment, tumor size is decreased by about 50%, about 55%, about 60%, about 70%, about 75%, about 80%, about 85%, about 90%, about 95%, about 99% or about 100%. In an embodiment, tumor size is decreased by 50%, 55%, 60%, 70%, 75%, 80%, 85%, 90%, 95%, 99%, or 100%.

Compositions and methods described herein thus contemplate treating tumors, including reducing their size. "Tumor" has the meaning ordinarily understood in the art, and includes an abnormal mass of tissue, typically resulting when cells divide more than they should or do not die when they should. "Tumors" as referred to herein may be benign (not cancerous), or malignant (cancerous) and may occur any place in the body.

In an embodiment, provided herein is a method of treating a cancer in a subject, comprising administering to a subject in need thereof an effective amount of a cyclin dependent kinase (CDK) inhibitor, thereby treating cancer in the subject. In an embodiment of a method described herein, the cancer is prostate cancer. In another embodiment, the prostate cancer is castration resistant prostate cancer (CRPC). In another embodiment, the cancer is refractory metastatic breast cancer. In another embodiment, the cancer is Ewing's sarcoma. In another embodiment, the cancer is glioblastoma. In another embodiment, the cancer is a hepatocellular carcinoma.

In an embodiment of a method described herein, the CDK is CDK7. In another embodiment, the CDK is CDK12. In another embodiment, the CDK is CDK13.

In an embodiment, the CDK inhibitor is THZ1. In another embodiment, the CDK inhibitor is SY1365. In an embodiment, the CDK inhibitor is SY-5609, a highly selective and potent cyclin-dependent kinase 7 (CDK7) inhibitor. In another embodiment, the CDK inhibitor is CT7001. In an embodiment, the CDK inhibitor is seliciclib, a combination of sapacitabine a and seliciclib, TG-02, small molecule drug ID 347143, small molecule drug ID 317335, small molecule drug ID 262544, small molecule drug ID 336946, PHA-793887, SY-351, roniciclib, SNS-032, and CDK9 inhibitor), BS-181L, and BS-194. Any other CDK inhibitor suitable for use to achieve the desired result can be employed in embodiments of the invention as described herein.

In an embodiment of a method described herein, the subject is resistant to anti-androgen therapy. In another embodiment, the anti-androgen therapy comprises enzalutamide. In another embodiment, the anti-androgen therapy comprises abiraterone.

In an embodiment of a method described herein, the effective amount of CDK inhibitor comprises about 10 mg/kg. Any suitable effective dose or administration regiment within the skill of the ordinary artisan can be employed to achieve the desired results.

In an embodiment, the treatment comprises and/or results in a reduction in tumor volume, a loss of PSA expression, increased necrosis, reduced proliferative activity, increased apoptosis, a reduction in p-MED1 levels in a tumor, reduced plasma PSA expression in the subject, or any combination thereof. Any other method or measure within the skill of the ordinary artisan for evaluating the effectiveness of a cancer treatment can be employed.

In an embodiment, provided herein is a method of treating a cancer in a subject, comprising administering to a subject in need thereof a pharmaceutical composition comprising an effective amount of a cyclin dependent kinase (CDK) inhibitor, thereby treating cancer in the subject. In an embodiment, the method further comprises a pharmaceutically acceptable carrier. In another embodiment, the composition is formulated for oral administration. In another embodiment, the composition is formulated for intravenous injection. Any other suitable route of administration within the skill of the ordinary artisan can be employed in the methods described herein.

In an embodiment, provided herein is a method of treating a disease in a subject, said disease characterized by androgen receptor (AR) dependent neoplastic growth, comprising administering to a subject in need thereof, an agent effective to inhibit MED1-mediated, AR-dependent oncogenic transcriptional amplification, thereby treating the disease. In an embodiment, the disease is a cancer. In an embodiment, the cancer is prostate cancer. In an embodiment, the prostate cancer is castration resistant prostate cancer (CRPC). In an embodiment, the cancer is refractory metastatic breast cancer. In another embodiment, the cancer is Ewing's sarcoma. In another embodiment, the cancer is glioblastoma. In another embodiment, the cancer is a hepatocellular carcinoma. In embodiments described herein, the disease can be any other disease, including a cancer characterized or affected by or related to the pathways described herein and above.

In an embodiment, the agent is a CDK inhibitor. In an embodiment, the CDK is CDK7. In an embodiment, the CDK is CDK12 or CDK13. In an embodiment, the CDK inhibitor is THZ1. In another embodiment, the CDK inhibitor is SY1365. In an embodiment, the CDK inhibitor is SY-5609, a highly selective and potent cyclin-dependent kinase 7 (CDK7) inhibitor. In another embodiment, the CDK inhibitor is CT7001. In an embodiment, the CDK inhibitor is seliciclib, a combination of sapacitabine a and seliciclib, TG-02, small molecule drug ID 347143, small molecule drug ID 317335, small molecule drug ID 262544, small molecule drug ID 336946, PHA-793887, SY-351, roniciclib, SNS-032, and CDK9 inhibitor), BS-181L, and BS-194. Any other CDK inhibitor suitable for use to achieve the desired result can be employed in embodiments of the invention as described herein.

In an embodiment, the subject is resistant to anti-androgen therapy. In another embodiment, the anti-androgen therapy comprises enzalutamide. In another embodiment, the anti-androgen therapy comprises abiraterone.

In an embodiment of a method described herein, the effective amount of the agent is about 10 mg/kg. Any suitable effective dose or administration regiment within the skill of the ordinary artisan can be employed to achieve the desired results.

In an embodiment, the treatment comprises and/or results in a reduction in tumor volume, a loss of PSA expression, increased necrosis, reduced proliferative activity, increased apoptosis, a reduction in p-MED1 levels in a tumor, reduced plasma PSA expression in the subject, or any combination thereof. Any other method or measure within the skill of the ordinary artisan for evaluating the effectiveness of treatment can be employed. In an embodiment, provided herein is a method for determining the prognosis of a patient suffering from a cancer, the method comprising determining a nuclear p-MED1 level in a sample from the patient, and comparing the level with a reference value, wherein an increased level of p-MED1 compared to the reference value is indicative of a poor prognosis or wherein a decreased level of p-MED1 compared to the reference value is indicative of a good prognosis. In an embodiment, the cancer is a prostate cancer. In an embodiment, the sample comprises prostate tissue.

In an aspect, provided herein is a method of treating an androgen receptor (AR) dependent cancer in a human subject in need thereof, the method comprising:

a) testing a cancer tissue sample obtained from the human subject to determine a nuclear phosphorylated-MED1 (p-MED1) level in the cancer tissue sample;

b) comparing the determined nuclear p-MED1 level in step (a) with a predetermined nuclear p-MED1 level in a control tissue sample, wherein the control tissue sample is a non-malignant (benign) tissue sample, a localized (primary) cancer tissue sample and/or a metastatic cancer tissue sample; wherein (i) a determined nuclear p-MED1 level that is increased compared to the predetermined nuclear p-MED1 level in the localized (primary) cancer tissue sample and/or in the metastatic cancer tissue sample is indicative of a poor prognosis, and (ii) a determined nuclear p-MED1 level that is decreased compared to the predetermined nuclear p-MED1 level in the non-malignant (benign) tissue sample is indicative of a good prognosis; and (c) administering to the human subject having (i) a determined nuclear p-MED1 level indicative of a good prognosis a therapeutically effective amount of an inhibitor of a cyclin dependent kinase (CDK) inhibitor, or administering to the human subject having (ii) a determined nuclear p-MED1 level indicative of a poor prognosis a therapeutically effective amount of an inhibitor of a cyclin dependent kinase (CDK) inhibitor and of an anti-androgen therapy, wherein the administering is sequential in either order or concurrent.

In an embodiment, the AR dependent cancer is prostate cancer. In one embodiment, the prostate cancer is castration resistant prostate cancer (CRPC). In another embodiment, the AR dependent cancer is refractory metastatic breast cancer, Ewing's sarcoma, glioblastoma, or hepatocellular carcinoma. In some embodiments, the CDK inhibitor is CDK7. In an embodiment, the CDK inhibitor is CDK12 or CDK13. In particular embodiments, the CDK inhibitor is THZ1. In some embodiments, the CDK inhibitor is SY1365. In another embodiment, the CDK inhibitor is SY-5609, a highly selective and potent cyclin-dependent kinase 7 (CDK7) inhibitor. In another embodiment, the CDK inhibitor is CT7001. In an embodiment, the CDK inhibitor is seliciclib, a combination of sapacitabine a and seliciclib, TG-02, small molecule drug ID 347143, small molecule drug ID 317335, small molecule drug ID 262544, small molecule drug ID 336946, PHA-793887, SY-351, roniciclib, SNS-032, and CDK9 inhibitor), BS-181L, and BS-194.

In one embodiment, the human subject is resistant to anti-androgen therapy. In an embodiment, the anti-androgen therapy comprises enzalutamide. In another embodiment, the anti-androgen therapy comprises abiraterone.

In an embodiment, the therapeutically effective amount of CDK inhibitor comprises about 10 mg/kg. In another embodiment, the treatment comprises a reduction in tumor volume, a loss of PSA expression, increased necrosis, reduced proliferative activity, increased apoptosis, a reduction in p-MED1 levels in a tumor, reduced plasma PSA expression in the subject, or a combination thereof.

In another aspect, provided herein is a method for predicting a prognosis of an androgen receptor (AR) dependent cancer and a response to cyclin dependent kinase (CDK) inhibition in a subject, the method comprising:

(a) measuring a nuclear p-MED1 level in a cancer tissue sample obtained from the human subject;

b) comparing the nuclear p-MED1 level measured in step (a) with a predetermined nuclear p-MED1 level in a control tissue sample, wherein the control tissue sample is a non-malignant (benign) tissue sample, a localized (primary) cancer tissue sample and/or a metastatic cancer tissue sample; wherein (i) a determined nuclear p-MED1 level that is increased compared to the predetermined nuclear p-MED1 level in the localized (primary) cancer tissue sample and/or in the metastatic cancer tissue sample is indicative of a poor prognosis, and (ii) a determined nuclear p-MED1 level that is decreased compared to the predetermined nuclear p-MED1 level in the non-malignant (benign) tissue sample is indicative of a good prognosis, wherein administration of a therapeutically effective amount of a CDK inhibitor to the human subject having (ii) a determined nuclear p-MED1 level indicative of a good prognosis is predictive of a therapeutic response to the CDK inhibitor, and wherein administration of a therapeutically effective amount of a CDK inhibitor to the human subject having (i) a determined nuclear p-MED1 level indicative of a poor prognosis is not predictive of a therapeutic response to the CDK inhibitor and requires further administration of a therapeutically effective amount of an anti-androgen therapy.

In an embodiment, the an anti-androgen therapy is administered in sequence with the CDK inhibitor, in either order, or concurrently therewith. In a particular embodiment, the AR dependent cancer is prostate cancer. In some embodiments, the prostate cancer is castration resistant prostate cancer (CRPC). In another embodiment, the AR dependent cancer is refractory metastatic breast cancer, Ewing's sarcoma, glioblastoma, or hepatocellular carcinoma. In an embodiment, the CDK inhibitor is CDK7. In another embodiment, the CDK inhibitor is CDK12 or CDK13. In a particular embodiment, the CDK inhibitor is THZ1. In another embodiment, the CDK inhibitor is SY-5609, a highly selective and potent cyclin-dependent kinase 7 (CDK7) inhibitor. In some embodiments, the CDK inhibitor is SY1365. In another embodiment, the CDK inhibitor is CT7001. In an embodiment, the CDK inhibitor is seliciclib, a combination of sapacitabine a and seliciclib, TG-02, small molecule drug ID 347143, small molecule drug ID 317335, small molecule drug ID 262544, small molecule drug ID 336946, PHA-793887, SY-351, roniciclib, SNS-032, and CDK9 inhibitor), BS-181L, and BS-194. In an embodiment, the human subject is resistant to anti-androgen therapy. In another embodiment, the anti-androgen therapy comprises enzalutamide. In an embodiment, the anti-androgen therapy comprises abiraterone. In some embodiments, the therapeutically effective amount of CDK inhibitor comprises about 10 mg/kg. In an embodiment, the treatment comprises a reduction in tumor volume, a loss of PSA expression, increased necrosis, reduced proliferative activity, increased apoptosis, a reduction in p-MED1 levels in a tumor, reduced plasma PSA expression in the subject, or a combination thereof.

In still another aspect, provided herein is a method for predicting a prognosis of an androgen receptor (AR) dependent prostate cancer in a human subject and for treating the AR dependent prostate cancer, the method comprising:

a) measuring an expression level of an AR target gene in a prostate cancer tissue sample obtained from the human subject, wherein the AR target gene comprises 2 to 128 genes selected from a gene-signature consisting of PGM3, TMCC3, APPBP2, PLPP1, TUBA3D, CAPZB, KIF22, ZCCHC6, LAT2, LRRFIP2, FKBP5, MRPS18A, SMS, NDFIP2, ABCC1, NDRG1, MTMR9, AGR2, BMPR1A, LRRC59, SNX25, TRIM3, CAMKK2, KRT18, SASH1, HMGCR, LIFR, HMGXB3, SSR3, ODC1, DHCR24, RHOU, UAP1, ELL2, PCMT1, SOCS2, CHRNA2, ORMDL2, PFKFB2, ACSL3, PMEPA1, SPDEF, SSR1, STEAP4, LDLR, GADD45G, SELENOS, FADS2, MICAL1, KCTD3, LRRC8A, HERC3, BMPR1B, SHROOM3, FGD4, IGF1R, PCTP, KLK3, MPC2, CREB3L4, MBOAT2, LRIG1, EAF2, SDK1, NSDHL, CSGAL-NACT1, VLDLR, GLUD1, ENDOD1, GLB1L2, ACAD8, THYN1, VPS27B, NCAPD3, PART1, MERTK, PRKCA, DBI, TTN, KCNMA1, CLDN8, ATAD2, PEX10, ELK4, SLC45A3, NBL1, AZGP1, CDC42EP3, FZD5, ATP1A1, SLC15A2, TMEM79, SSR2, KLF15, SEC11C, B2M, NNMT, NKX3-1, C19orf48, FASN, KRT8, EFCAB12, KLC2, DOLK, ZNF613, LDLRAD3, SSR4, MFSD5, C1orf116, TMEM50A, TMPRSS2, HIST2H2BE, ATP6V0A2, FAM174B, ANKRD37, INSIG1, C9orf152, MYBPC1, STK39, MTOR, UBE2J1, FICD, PTPRCAP, AMACR, ZNF350, OTUD7B, PRAG1, and PAGR1, b) comparing the level of RNA expression of the AR target gene in the prostate cancer tissue sample from the human subject to a control RNA expression level of the AR target gene in a prostate tissue sample obtained from a healthy human subject, wherein an at least 2-fold increase in the expression level of the 2 to 128 genes indicates a poor prognosis for the androgen receptor (AR) dependent prostate cancer in the human subject;

c) identifying the human subject as being prone to not respond to CDK inhibition as a monotherapy based on the at least 2-fold increase in the expression level of the 2 to 128 genes as compared to the control RNA expression level of the AR target gene in the prostate tissue sample obtained from the healthy human subject; and d) administering to the human subject identified in step (c) a combination therapy comprising a therapeutically effective amount of an inhibitor of a cyclin dependent kinase (CDK) inhibitor and of an anti-androgen therapy, wherein the administering is sequential, in either order, or concurrent.

In an embodiment, the anti-androgen therapy is administered in sequence with the CDK inhibitor, in either order, or concurrently therewith. In a specific embodiment, the AR dependent cancer is prostate cancer. In another embodiment, the prostate cancer is castration resistant prostate cancer (CRPC). In a further embodiment, the AR dependent cancer is refractory metastatic breast cancer, Ewing's sarcoma, glioblastoma, or hepatocellular carcinoma. In one embodiment, the CDK inhibitor is CDK7. In another embodiment, the CDK inhibitor is CDK12 or CDK13. In a particular embodiment, the CDK inhibitor is THZ1. In another embodiment, the CDK inhibitor is SY-5609, a highly selective and potent cyclin-dependent kinase 7 (CDK7) inhibitor. In some embodiments, the CDK inhibitor is SY1365. In another embodiment, the CDK inhibitor is CT7001. In an embodiment, the CDK inhibitor is seliciclib, a combination of sapacitabine a and seliciclib, TG-02, small molecule drug ID 347143, small molecule drug ID 317335, small molecule drug ID 262544, small molecule drug ID 336946, PHA-793887, SY-351, roniciclib, SNS-032, and CDK9 inhibitor), BS-181L, and BS-194. In another embodiment, the human subject is resistant to anti-androgen therapy. In an embodiment, the anti-androgen therapy comprises enzalutamide. In another embodiment, the anti-androgen therapy comprises abiraterone. In an embodiment, the therapeutically effective amount of CDK inhibitor comprises about 10 mg/kg. In some embodiments, the treatment comprises a reduction in tumor volume, a loss of PSA expression, increased necrosis, reduced proliferative activity, increased apoptosis, a reduction in p-MED1 levels in a tumor, reduced plasma PSA expression in the subject, or a combination thereof.

CDK Inhibitors

In embodiments, the compositions, formulations, and methods described herein employ cyclin dependent kinase (CDK) inhibitors. Cyclin-dependent kinases (CDKs) are protein kinases characterized by the need for a separate subunit—a cyclin—that provides domains essential for enzymatic activity. CDKs play important roles in the control of cell division and modulate transcription in response to several extra- and intracellular cues. CDKs are traditionally separated into cell-cycle or transcriptional CDKs, although these activities are frequently combined in many family members.

Transcriptional CDKs include, e.g., CDK7, CDK8, CDK9, CDK12, and CDK13. Various inhibitors of the activity of these and other CDKs are known and readily available to one of ordinary skill in the art. Such CDK inhibitors are within the scope of the present invention and include, without limitation, THZ1 (a CDK7 inhibitor), SY1365 (a CDK7 inhibitor), CT7001 (a CDK7 inhibitor), seliciclib (a CDK-2,7,9 inhibitor), a combination of sapacitabine a (pyrimidine analogue prodrug with antineoplastic activity) and seliciclib, TG-02 (a CDKs 1, CDK2, CDK7 and CDK9 inhibitor), small molecule drug ID 347143 (a CDK7 inhibitor), small molecule drug ID 317335 (a CDK7 inhibitor), small molecule drug ID 262544 (a CDK7 inhibitor), small molecule drug ID 336946 (a CDK7 inhibitor), PHA-793887 (a pan CDK inhibitor), SY-351 (a CDK7 inhibitor), roniciclib (a pan CDK inhibitor that also is called BAY-1000394), SNS-032 (a selective CDK2, CDK7, and CDK9 inhibitor), BS-181L (a selective CDK7 inhibitor), and BS-194 (a CDK2, CDK1, CDK5, CDK7, and CDK9 inhibitor) and or any other CDK inhibitor suitable to achieve the desired result.

THZ1 is a selective and potent covalent CDK7 inhibitor with an $IC_{50}$ of 3.2 nM. At higher concentrations, it also targets, inter alia, CDK12 and CDK13 kinase activity. THZ1 is a phenylaminopyrimidine bearing cysteine-reactive acrylamide moiety and the THZ1 targeting site on CDK7/12/13 lies outside the kinase domain. Its molecular formula is $C_{31}H_{28}ClN_7O_2$ and can be depicted as:

As shown and described herein in accordance with embodiments of the invention, CDK7 directed MED1 phosphorylation at T1457 is a key regulator of AR function, and inhibition of the CDK7-MED1 axis results in significant tumor growth inhibition in AR-positive prostate cancer cells in both cell culture and in vivo models.

As described and shown herein, including in the Examples provided, MED1 undergoes CDK7 dependent phosphorylation and physically engages AR at super-enhancer sites, and is an essential determinant for AR-mediated gene transcription. Additionally, the CDK7 specific inhibitor THZ1 blunts AR-dependent neoplastic growth by blocking AR/MED1 co-recruitment at a genome-wide level, as well as results in reversion of the hyper-phosphorylated MED1 associated enzalutamide resistant phenotype. As shown herein, in vivo, THZ1 induces tumor regression of AR amplified castration-resistant human prostate cancer in xenograft mouse models. Together, CDK7 inhibition selectively targets MED1-mediated, AR-dependent oncogenic transcriptional amplification, thus representing a new approach for the treatment of certain cancers, including advanced prostate cancer, as described herein in accordance with embodiments of the present invention.

Pharmaceutical Compositions

Described herein are pharmaceutical compositions comprising compounds of the invention and one or more pharmaceutically acceptable carriers and methods of administering them. "Pharmaceutically acceptable carriers" include any excipient which is nontoxic to the cell or mammal being exposed thereto at the dosages and concentrations employed. The pharmaceutical composition may include one or more therapeutic agents.

Thus, as used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Examples of such carriers or diluents include, but are not limited to, water, saline, finger's solutions, dextrose solution, and 5% human serum albumin Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Moreover, "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable" also includes those carriers approved by a regulatory agency of the Federal or a state government or listed in the U.S. Pharmacopeia or other generally recognized pharmacopeia for use in animals and, more particularly, in humans.

In an embodiment, pharmaceutical compositions containing the therapeutic agent or agents described herein, can be, in one embodiment, administered to a subject by any method known to a person skilled in the art, such as, without limitation, orally, parenterally, transnasally, transmucosally, subcutaneously, transdermally, intramuscularly, intravenously, intraarterially, intra-dermally, intra-peritoneally, intra-ventricularly, intra-cranially, intra-vaginally, or intra-tumorally.

Carriers may be any of those conventionally used, as described above, and are limited only by chemical-physical considerations, such as solubility and lack of reactivity with the compound of the invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, traga-canth, gelatin, calcium silicate, microcrystalline cellulose, polyvinylpyrrolidone, cellulose, water and methylcellulose. The formulations can additionally include lubricating agents such as talc, magnesium stearate, and mineral oil; wetting agents, surfactants, emulsifying and suspending agents; pre-serving agents such as methyl- and propylhydroxybenzo-ates; sweetening agents; flavoring agents, colorants, buffer-ing agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chlo-ride. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. In one embodiment, water, preferably bacteriostatic water, is the carrier when the pharmaceutical composition is admin-istered intravenously or intratumorally. Saline solutions and aqueous dextrose and glycerol solutions can also be employed as liquid carriers, particularly for injectable solu-tions.

Pharmaceutical compositions suitable for injectable use, including intratumoral injection, may include sterile aque-ous solutions (where water soluble) or dispersions and sterile powders for the extemporaneous preparation of sterile injectable solutions or dispersion. For intravenous adminis-tration, suitable carriers include, without limitation, physi-ological saline, bacteriostatic water, Cremophor EL™ (BASF, Parsippany, N.J.) or phosphate buffered saline (PBS). The composition should be sterile and should be fluid to the extent that easy syringeability exists. It should be stable under the conditions of manufacture and storage and be preserved against the contaminating action of microor-ganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be main-tained, for example, by the use of a coating such as lecithin, by the maintenance of the required particle size in the case of dispersion and by the use of surfactants. Prevention of action of microorganisms can be achieved by various anti-bacterial and antifungal agents, for example, parabens, chlo-robutanol, phenol, ascorbic acid, thimerosal, and the like. In many cases, it will be preferable to include isotonic agents, for example, sugars, polyalcohols such as manitol, sorbitol or sodium chloride in the composition. Prolonged absorption of the injectable compositions can be brought about by including in the composition an agent which delays absorp-tion, for example, aluminum monostearate and gelatin.

Sterile injectable solutions can be prepared by incorpo-rating the active compound in the required amount in an appropriate solvent with one or a combination of ingredients enumerated above, as appropriate, followed by filtered ster-ilization. Generally, dispersions are prepared by incorporat-ing the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Within the present invention, the disclosed compounds may be prepared in the form of pharmaceutically acceptable salts. "Pharmaceutically acceptable salts" refer to deriva-tives of the disclosed compounds wherein the parent com-pound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The phar-maceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxyma-leic, phenylacetic, glutamic, benzoic, salicylic, sulfanilic, 2-acetoxybenzoic, fumaric, toluenesulfonic, methanesulfo-nic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine Common salt-forming cations include, without limitation, ammonium, calcium, iron, mag-nesium, potassium, pyridinium, quaternary ammonium, sodium, and copper. Common salt-forming anions include, without limitation, acetate, carbonate, chloride, citrate, cya-nide, fluoride, nitrate, nitrite, oxide, phosphate, and sulfate.

Compounds described herein also can be prepared in alternate forms. For example, many amino-containing com-pounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present inven-tion may exist as zwitterions. All forms of the compounds, including free acid, free base and zwitterions, are contem-plated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwit-terions.

The compositions and formulations as described herein may be administered alone or with other biologically-active agents Administration can be systemic or local, e.g. through portal vein delivery to the liver. In addition, it may be advantageous to administer the composition into the central nervous system by any suitable route, including intraven-tricular and intrathecal injection. Intraventricular injection may be facilitated by an intraventricular catheter attached to a reservoir (e.g., an Ommaya reservoir). Pulmonary admin-istration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant.

Another formulation suitable for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration, e.g. as an ointment, a gel a drop or a cream. For topical administration to body surfaces using, for example, creams, gels, drops, ointments and the like, the compounds of the present invention can be prepared and applied in a physiologically acceptable diluent with or without a pharmaceutical carrier. The present invention may be used topically or transdermally to treat cancer, for example, melanoma. Adjuvants for topical or gel base forms may include, for example, sodium carboxymethylcellulose, polyacrylates, polyoxyethylene-polyoxypropylene-block polymers, polyethylene glycol and wood wax alcohols. In one embodiment, the composition for topical administration comprises 5% by weight of the active compound. In another embodiment, the composition for topical administration comprises 10% by weight of the active compound.

In one embodiment, the compositions are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

It may be desirable to administer a pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material. According to some embodiments, administration can be by direct injection e.g., via a syringe, at the site of a tumor or neoplastic or pre-neoplastic tissue.

A compound of the present invention can be delivered in an immediate release or in a controlled release system. In one embodiment, an infusion pump may be used to administer a compound of the invention, such as one that is used for delivering chemotherapy to specific organs or tumors (see Buchwald et al., 1980, Surgery 88: 507; Saudek et al., 1989, N. Engl. J. Med. 321: 574). In another embodiment, a compound of the invention is administered in combination with a biodegradable, biocompatible polymeric implant, which releases the compound over a controlled period of time at a selected site. Examples of polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). In yet another embodiment, a controlled release system can be placed in proximity of the therapeutic target, thus requiring only a fraction of the systemic dose.

Furthermore, at times, the pharmaceutical compositions formulated for parenteral administration may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. The above formulations may also be used for direct intra-tumoral injection. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. Moreover, to minimize or eliminate pain or discomfort resulting from injection or other administration, a pain reducing agent, as described herein, also may be administered either within the formulation, or separate from it.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

Effective Doses

Effective doses of the compositions of the present invention, for treatment of conditions or diseases vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy. The pharmaceutical compositions of the invention thus may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

Furthermore, a skilled artisan would appreciate that the term "therapeutically effective amount" may encompass total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of a compound of the invention that will be effective in the treatment of a particular disorder or condition, including cancer, also will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. In one embodiment, the dosage will be within the range of about 0.01-about 1000 mg/kg of body weight. In another embodiment, the dosage will be within the range of about 0.1 mg/kg to about 100 mg/kg. In another embodiment, the dosage will be within the range of about 1 mg/kg to about 10 mg/kg. In an embodiment, the dosage is about 10 mg/kg. In another embodiment, the dosage is 10 mg/kg.

The compound or composition of the invention may be administered only once, or it may be administered multiple times. For multiple dosages, the composition may be, for example, administered three times a day, twice a day, once a day, once every two days, twice a week, weekly, once every two weeks, or monthly.

In an embodiment, the dosage is administered twice daily. In an embodiment, the dosage is administered for four weeks. In an embodiment, the dosage is 10 mg/kg and is administered twice daily for four weeks. The dosage may be administered for 1 week, ten days, two weeks, three weeks, four weeks, six weeks, eight weeks or more, as needed to achieve the desired therapeutic effect. Moreover, effective doses may be extrapolated from dose-response curves derived from in vitro or animal model test bioassays or systems.

As used herein, the term "administering" refers to bringing in contact with a compound of the present invention Administration can be accomplished to cells or tissue cultures, or to living organisms, for example humans. In one embodiment, the present invention encompasses administering the compounds and compositions of the present invention to a human subject.

In one embodiment, methods of the present invention comprise the step of contacting one or more cells of said subject with a compound or a composition as described herein. In one embodiment, contacting one or more cells of a subject with a compound described herein comprises the step of administering a composition comprising said compound to said subject.

In some embodiments, a timepoint comprises a point in time. In another embodiment, a timepoint comprises a time period shorter than 1 minute. In another embodiment, a timepoint comprises a time period shorter than 5 minutes. In another embodiment, a timepoint comprises a time period shorter than 30 minutes. A skilled artisan would appreciate that the terms "timepoint", "time point" and "time period" may be used interchangeably having all the same qualities and meanings.

In an embodiment, any of the therapeutic or prophylactic drugs or compounds described herein may be administered simultaneously. In another embodiment, they may be administered at different timepoint than one another. In one embodiment, they may be administered within a few minutes of one another. In another embodiment, they may be administered within a few hours of one another. In another embodiment, they may be administered within 1 hour of one another. In another embodiment, they may be administered within 2 hours of one another. In another embodiment, they may be administered within 5 hours of one another. In another embodiment, they may be administered within 12 of one another. In another embodiment, they may be administered within 24 hours of one another.

In one embodiment, any of the therapeutic or prophylactic drugs or compounds described herein may be administered at the same site of administration. In another embodiment, they may be administered at different sites of administration.

It is to be noted that dosage values and amounts and ratios of individual components of the compositions described herein also may vary with the type and severity of the condition to be alleviated and other factors. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions described and contemplated herein can be included in a container, pack, or dispenser together with instructions for administration.

Tumors, Cancer, and other Disorders

In embodiments, where the terms "reducing a size of a tumor", "treating or inhibiting a malignant cell proliferative disease or disorder", "treating or inhibiting a non-solid cancer", "treating or inhibiting a tumor" are used herein in the description and in the claims, such terms are intended to encompass tumor formation, primary tumors, tumor progression or tumor metastasis. Furthermore, the compounds, compositions, and methods described herein contemplate treatment of tumors and tumor cells located in any tissue in which such tumors can occur in a subject.

In one embodiment, the methods of the present invention comprise inhibiting proliferation of cancer or tumor cells. In one embodiment, the term "inhibiting proliferation" in relation to cancer cells, in the context of the present invention refers to a decrease in at least one of the following: number of cells (due to cell death which may be necrotic, apoptotic or any other type of cell death or combinations thereof) as compared to control; decrease in growth rates of cells, i.e. the total number of cells may increase but at a lower level or at a lower rate than the increase in control; decrease in the invasiveness of cells (as determined for example by soft agar assay) as compared to control even if their total number has not changed; progression from a less differentiated cell type to a more differentiated cell type; a deceleration in the neoplastic transformation; or alternatively the slowing of the progression of the cancer cells from one stage to the next.

The term "treatment of cancer" or "treatment of a tumor" or "reducing size of a tumor" in the context of the present invention also includes at least one of the following: a decrease in the rate of growth of the cancer or tumor (i.e. the cancer or tumor still grows but at a slower rate); cessation of growth of the cancerous growth, i.e., stasis of the tumor growth, and, in one embodiment, the tumor diminishes or is reduced in size. The term also includes reduction in the number of metastasis, reduction in the number of new metastasis formed, slowing of the progression of cancer from one stage to the other and a decrease in the angiogenesis induced by the cancer. In one embodiment, the tumor is totally eliminated. Additionally, included in this term is lengthening of the survival period of the subject undergoing treatment, lengthening the time of diseases progression, tumor regression, and the like. This term also encompasses prevention for prophylactic situations or for those individuals who are susceptible to contracting a tumor. In embodiments, the administration of the compounds of the present invention will reduce the likelihood of the individual contracting the disease. In one embodiment, the individual to whom the compound is administered does not contract the disease.

Thus, in one embodiment, treating may include directly affecting or curing, suppressing, inhibiting, preventing, reducing an incidence, reducing the severity of, delaying the onset of, reducing symptoms associated with the disease, disorder or condition, or a combination thereof. Thus, in one embodiment, "treating" refers, inter alia, to delaying progression, expediting remission, inducing remission, augmenting remission, speeding recovery, increasing efficacy of or decreasing resistance to alternative therapeutics, or a combination thereof. In another embodiment, treating refers to reducing the pathogenesis of, ameliorating the symptoms of, ameliorating the secondary symptoms of, or prolonging the latency to a relapse of a cancer in a subject. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, a subject as described herein has a pre-cancerous condition. In another embodiment, a subject as described herein has a benign hyperproliferative disorder. In another embodiment, a subject has cancer.

In one embodiment, the term "pre-cancer" or "pre-malignant" as used herein interchangeably refers to diseases, syndromes or other conditions associated with an increased risk of cancer. Pre-cancer conditions in the context of the present invention include, but are not limited to: breast calcifications, vaginal intra-epithelial neoplasia, Barrett's esophagus, atrophic gastritis, dyskeratosis congenital, sideropenic dysphagia, lichen planus, oral sibmucous fibrosis, actinic keratosis, solar elastosis, cervical desplasia, leukoplakia and erythroplakia, or other tumor as described herein.

In one embodiment, the term "benign hyperproliferative disorder" as used herein refers to a condition in which there is an abnormal growth and differentiation of cells and an increase in the amount of organic tissue that results from cell proliferation. The benign hyperproliferative disorder may be attributed to lack of response or inappropriate response to regulating factors, or alternatively to dysfunctional regulating factors. Non-limiting example of benign hyperproliferative disorder are psoriasis and benign prostatic hyperplasia (BPH).

In another embodiment, the subject has a lymphoma. In one embodiment, lymphomas develop in the glands or nodes of the lymphatic system, a network of vessels, nodes, and organs (in one embodiment, the spleen, tonsils, and thymus) that purify bodily fluids and produce lymphocytes, which, in one embodiment, comprise infection-fighting white blood cells. In one embodiment, lymphomas are "solid cancers." In another embodiment, a lymphoma may occur in a specific organ such as the stomach, breast or brain. In one embodiment such a lymphoma is an extranodal lymphoma.

In one embodiment, a subject as described herein comprises a Mixed Type cancer. In one embodiment, a mixed type cancer comprises several types of cells. In one embodiment, the type components may be within one category or from different categories. In one embodiment a Mixed Type cancer comprises adenosquamous carcinoma, mixed mesodermal tumor, carcinosarcoma, teratocarcinoma, or a combination thereof.

As used herein, the term "cancer" includes the above categories of carcinoma, sarcoma, myeloma, leukemia, lymphoma and mixed type tumors. In particular, the term cancer includes: lymphoproliferative disorders, breast cancer, ovarian cancer, prostate cancer, cervical cancer, endometrial cancer, lung cancer, bone cancer, liver cancer, stomach cancer, bladder cancer, colon cancer, colorectal cancer, pancreatic cancer, cancer of the thyroid, head and neck cancer, cancer of the central nervous system, brain cancer, cancer of the peripheral nervous system, skin cancer, kidney cancer, as well as metastases of all the above. More particularly, as used herein the term may refer to: hepatocellular carcinoma, hematoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

In another embodiment, the cancer is an adenocarcinoma of the stomach or gastroesophageal junction, Dermatofibrosarcoma protuberans, Endocrine/neuroendocrine tumors, Gastrointestinal stromal tumor, Giant cell tumor of the bone, Kaposi sarcoma, Myelodysplastic/myeloproliferative disorders, Ovarian epithelial/fallopian tube/primary peritoneal cancers, Soft tissue sarcoma, Systemic mastocytosis, Germ cell tumor, or a combination thereof.

In one embodiment, the subject having cancer or a tumor has been treated with surgery, chemotherapy, radiation therapy, a targeted therapy, including therapies that are intended to boost immune system responses against cancer, or a combination thereof.

In one embodiment, the tumor is a solid tumor. In one embodiment, the solid tumor is a colon carcinoma, prostate cancer, breast cancer, lung cancer, skin cancer, liver cancer, bone cancer, ovary cancer, pancreas cancer, brain cancer, head and neck cancer or other solid tumor.

In one embodiment, the cancer or non-cancerous tumor is in the breast, prostate, lung, colon, stomach, pancreas, ovary, or brain. In another embodiment, the tumor is in a tissue that comprises gastrointestinal (GI) tract tissue. In another aspect, the GI tract tissue comprises tissue of the anus, rectum, colon, esophagus, stomach, mouth, pharynx, small intestine, liver, pancreas, or biliary tract. In another embodiment, the cancer is a hematopoietic cancer, a neuroblastoma, or a malignant glioma.

Combined Treatments

In another embodiment, any of the methods of the present invention may further comprise the step of contacting one or more cells of said subject with an anti-cancer treatment, or otherwise include a combination treatment or therapy. In one embodiment, the anti-cancer treatment is radiotherapy.

In another embodiment, the anti-cancer treatment is an anti-cancer drug. In one embodiment, the anti-cancer drug is a chemotherapeutic.

In one embodiment, the chemotherapeutic comprises 5-fluorouracil, Bleomycin, capecitabine, cisplatin, Cyclophosphamide, dacarbazine, Doxorubicin, Epirubicin, etoposide, folinic acid, Methotrexate, Mustine, oxaliplatin, prednisolone, procarbazine, vinblastine, vincristine, or a combination thereof.

In another embodiment, the present invention provides a method of treating, inhibiting, or suppressing a cancer or tumor in a subject comprising contacting one or more cells of said subject with a tumor reducing composition as described herein and a targeted therapy.

Targeted Therapies

In one embodiment, the present invention provides methods of treating cancer comprising administering a composition as described herein in combination with one or more targeted therapies.

In one embodiment, an immunotherapeutic compound is targeted to particular molecules expressed abnormally by cancer cells. In one embodiment, the targeted therapy comprises a hormone therapy, signal transduction inhibitor, gene expression modulator, apoptosis inducer, angiogenesis inhibitor, immunotherapy, or toxin delivery molecules.

In one embodiment, the targeted therapy utilizes small molecules. In another embodiment, the targeted therapy utilizes antibodies, which, in one embodiment, are monoclonal antibodies.

In one embodiment, the immunotherapeutic compound comprises abiraterone acetate (ZYTIGA®), ado-trastuzumab emtansine (KADCYLA®), afatinib dimaleate (GILOTRIF®), alectinib (ALECENSA®), alemtuzumab (CAMPATH®), Alitretinoin (PANRETIN®), anastrozole (ARIMIDEX®), Atezolizumab (TECENTRIQ™), axitinib (INLYTA®), belinostat (BELEODAQ®), Bevacizumab (AVASTIN®), bexarotene (TARGRETIN®), blinatumomab (BLINCYTO®), bortezomib (VELCADE®), bosutinib (BOSULIF®), brentuximab vedotin (ADCETRIS®), Cabazitaxel (JEVTANA®), cabozantinib (CABOMETYX™), Cabozantinib (COMETRIQ®), carfilzomib (KYPROLIS®), ceritinib (LDK378/Zykadia™), Cetuximab (ERBITUX®), cobimetinib (COTELLIC™), crizotinib (XALKORI®), dabrafenib (TAFINLAR®), daratumumab (DARZA-LEX™), dasatinib (SPRYCEL®), denileukin diftitox (ONTAK®), Denosumab (XGEVA®), Dinutuximab (UNITUXIN™), elotuzumab (EMPLICITI™), enzalutamide (XTANDI®), Erlotinib (TARCEVA®), everolimus (AFINITOR®), exemestane (AROMASIN®), fulvestrant (FASLODEX®), gefitinib (IRESSA®), Ibritumomab tiuxetan (ZEVALIN®), ibrutinib (IMBRUVICA®), idelalisib (ZYDELIG®), Imatinib mesylate (GLEEVEC®), Ipilimumab (YERVOY®), ixazomib citrate (NINLARO®), Lanreotide acetate (SOMATULINE® Depot), lapatinib (TYKERB®), lenvatinib mesylate (LENVIMA®), letrozole (FEMARA®), necitumumab (PORTRAZZA™), nilotinib (TASIGNA®), nivolumab (OPDIVO®), obinutuzumab (GAZYVA®), ofatumumab (ARZERRA®), olaparib (LYNPARZA™), olaratumab (LARTRUVO™), osimertinib (TAGRISSO™), palbociclib (IBRANCE®), panitumumab (VECTIBIX®), panobinostat (FARYDAK®), pazopanib (VOTRIENT®), pembrolizumab (KEYTRUDA®), pertuzumab (PERJETA®), pralatrexate (FOLOTYN®), radium 223 dichloride (XOFIGO®), ramucirumab (CYRAMZA®), regorafenib (STIVARGA®), rituximab (RITUXAN®), romidepsin (ISTODAX®), ruxolitinib phosphate (JAKAFI®), siltuximab (SYLVANT®), sonidegib (ODOMZO®), sorafenib (NEXAVAR®), sunitinib (SUTENT®), tamoxifen (NOLVADEX), temsirolimus (TORISEL®), toremifene (FARESTON®), trametinib (ME- KINIST®), Trastuzumab (HERCEPTIN®), Tretinoin (VESANOID®), vandetanib (CAPRELSA®), vemurafenib (ZELBORAF®), venetoclax (VENCLEXTA™), Vismodegib (ERIVEDGE®), vorinostat (ZOLINZA®), ziv-aflibercept (ZALTRAP®), or a combination thereof.

In another embodiment, methods of the present invention further comprise the step of contacting one or more cells of the subject with an immunotherapeutic compound.

Immunotherapeutic Compounds

In an embodiment, an immunotherapy as described herein is a monoclonal antibody that recognizes specific molecules on the surface of cancer cells. In one embodiment, binding of the monoclonal antibody to the target molecule results in the immune destruction of cells that express that target molecule. In another embodiment, the antibody binds to certain immune cells to enhance their actions on cancer cells.

In one embodiment, the immunotherapeutic compound comprises imatinib or trastuzumab. In one embodiment, the immunotherapeutic compound comprises a checkpoint inhibitor. In one embodiment, the checkpoint inhibitor comprises a Programmed cell Death protein 1 (PD1) inhibitor or a Programmed cell Death Ligand 1 (PD-L1) inhibitor. In one embodiment, the PD-1 or PD-L1 inhibitor is an antibody. In one embodiment, the antibody comprises Nivolumab, Pembrolizumab, Pidilizumab, Avelumab, BMS 936559, or MPDL328OA. In one embodiment, the immunotherapeutic compound comprises chimeric antigen receptor T cells (CAR T-cells).

Each of the above additives, excipients, formulations and methods of administration represents a separate embodiment of the present invention.

All patents, patent applications, and scientific publications cited herein are hereby incorporated by reference in their entireties.

The following examples are presented in order to more fully illustrate the preferred embodiments of the invention. It should in no way be construed, however, as limiting the broad scope of the invention.

EXAMPLES

Potent inhibition of AR signalling can be critical to treat castration-resistant prostate cancer. The Examples provided herein reflect experimentation that uncovers a driver role for CDK7 in regulating AR-mediated transcription through phosphorylation of MED1, thus revealing a therapeutically targetable vulnerability in AR-addicted CRPC.

In the Examples described herein, it was shown, inter alia, that ligand-dependent AR transcriptional signaling is activated through a "phosphoswitch" catalyzed by cyclin-dependent-kinase 7 (CDK7). Specifically, CDK7 phosphorylates the transcriptional co-activator MED1 at threonine 1457 to promote formation of the AR-transcriptional complex. Finally, CDK7 inhibition with the recently developed covalent inhibitor THZ1 attenuates AR-signaling and exquisitely eliminates AR-addicted PCa cells.

Methods

Cell Culture and Drug Reagents

Prostate parental cell lines used in this study were obtained from ATCC, LNCaP-AR cells were a gift from Dr. Charles Sawyers (Memorial Sloan-Kettering Cancer Center, New York, NY), and LNCaP AR-KO cells were a gift from Dr. Dean Tang (Roswell Park Cancer Institute, Buffalo, NY). LNCaP, LNCaP-AR, 22RV1, LAPC4, DU145, PC3, and LNCaP AR-KO prostate cancer cell lines were grown in RPMI 1640 (Gibco, 11875093), and VCaP prostate cancer cell line was grown in DMEM with Glutamax (Gibco, 21013024). The medium was supplemented with 10% Fetal Bovine Serum (FBS) (HYC, SH30910.03) and 1% Penicillin Streptomycin Solution (Invitrogen, 15140122), hereto referred to as "complete media." The immortalized benign prostate cell line RWPE-1 was grown in keratinocyte media with supplements (Thermo Fisher Scientific, 17005042). LNCaP-AR and VCaP enzalutamide-resistant cell lines were derived from enzalutamide-resistant PCa tumor xenograft as described previously. LNCaP and LAPC4 enzalutamide-resistant cell lines were generated by culturing the cells in presence of 20 μM enzalutamide for 3-4 months in vitro. Polyclonal pools of enzalutamide-resistant cells were cultured and maintained in media containing enzalutamide throughout. All experiments for enzalutamide resistant pools were done in presence of enzalutamide throughout the remainder of all experiments with these cells. The cell lines were tested negative for mycoplasma contamination and maintained in a humidified incubator at 37° C. and 5% CO2.

For AR signaling stimulation experiments, cells were plated in complete media at required confluency. After 24 h cells were washed with DPBS and cultured in RPMI/DMEM without Phenol Red (Invitrogen, 11835030) and 10% charcoal-dextran stripped FBS (Gemini BioProducts, 100-119) for 72 h. Cells were then stimulated with 10 nM DHT for the specific time points.

Drugs:

CDK7 inhibitor-THZ1 (MedChem Express, HY-80013A/CS-3168), JQ1 (Cayman Chemical Company, 11187), LDC000067 (Selleckchem, S7461), R1881C-III (Sigma, R0908), Trametinib (Selleckchem, S2673), Enzalutamide (Selleckchem, 51250) and Dinaciclib (Selleckchem, S2768), were dissolved and aliquoted in DMSO (Sigma-Aldrich, D2650). 5α-Dihydrotestosterone (Cerilliant, D073) was dissolved and aliquoted in methanol Cell Viability, Colony Formation and Proliferation Assays Cell viability assays were performed by seeding the cells in 96-well plates at 2500-10000 cells/well (optimum density for growth) in a total volume of 100 μL complete media. Serially diluted compounds/drugs in 100 μL media were added to the cells 24 h post seeding. Following 96 h incubation, cell viability was assessed by Cell-Titer GLO (Promega, PR G7571). The measurements were normalized and regression curves were fitted to calculate $GI_{50}$ using GraphPad Prism software.

For the long-term colony formation assay, 10,000-50,000 cells/well in six-well plates (n=3) were seeded and treated with the required drugs/compounds or vehicle for 14 days. Media was refreshed every 4-5 days. Colonies were fixed and stained using 0.5% (w/v) crystal violet (Sigma, C0775) in 20% (v/v) methanol for 30 min, washed with distilled deionized water, and air-dried. To quantify staining, we washed the stained wells with 500 μL 10% acetic acid and using colorimetric assays determined the absorbance at 590 nm using a spectrophotometer (Synergy HT, BioTek Instruments, Vermont-USA).

For the cell proliferation assay, the cells previously transfected with siRNA and/or wt-MEDI/T1032A-MED1/T1457A-MED1/T1457D-MED1, and DM-MED1 (containing both T1032A and T1457A mutations) or respective controls. 24 h post transfection the cells were trypsinized and then were seeded at a density of 20,000-50,000 cells/well in 12-well plates (n=3). 24 h after seeding the cells were either treated with THZ1 or DMSO. The cells were harvested, and live cell numbers were counted in the indicated conditions at the set time points by Countess II FL (Invitrogen, AMQAF1000).

Annexin V-FITC Analysis

Apoptosis induction was quantified using the Annexin-V and FITC Apoptosis Kit, as per manufacturer's instructions. Briefly LNCaP, VCaP, DU145 and PC3 cells were plated at a density of $5\times10^5$ cells per well in a 6-well culture plate. After subsequent treatments, the cells were harvested following incubation with a staining solution containing 10 μL propidium iodide and 5 μL Annexin for 10 min and analyzed by flow cytometry (BD FACS Aria II, BD Biosciences, San Jose).

Western Blot and Co-Immunoprecipitations Analysis

Cell lysates were prepared with RIPA buffer (Boston Bioproducts, BP-115DG)-10 mM Tris-HCl pH 7.5, 1 mM EDTA, 400 mM NaCl, 0.5% NP-40 and 1 mM DTT, supplemented with protease inhibitor cocktail (Pierce, A32965) and phosphatase inhibitor (Thermo, 1861280). For immunoblotting 200 μg total protein extract was boiled in sample buffer and 15-25 μg aliquots were separated by SDS-PAGE and transferred onto Polyvinylidene Difluoride membrane (GE Healthcare, IPVH00010). The membrane was incubated for one hour in blocking buffer [Tris-buffered saline, 0.1% Tween (TBS-T), 5% nonfat dry milk followed by overnight incubation on a rocker at 4° C. with the primary antibody. Following a wash with TBS-T, the blot was incubated with horseradish peroxidase-conjugated secondary antibody for 2 hrs on a rocker at room temperature. The blots were washed again and signals were visualized using enhanced chemiluminescence system as per manufacturer's protocol (GE Healthcare) or Kwik Quant Imager (Kindle Biosciences). Primary antibodies used in the immunoblotting (IB), immunoprecipitation (IP), and Chromatin Immunoprecipitation sequencing (ChIP-seq) assays are as follows: AR_IP, IB, ChIP-Seq (Millipore, 06-680); pS81-AR_IB (Millipore, 07-1375-EMD); RNA Pol II_IP, IB (Abcam, ab5408); ERG_IB (Abcam, a92513); PSA_IB (Dako, A0562); H3-acetyl K27_IP, IB, ChIP Seq (Abcam, ab32104) cPARP_IB (Cell Signaling Technology, 9541s); Cleaved caspase-3_IB (Cell Signaling Technology, 9664t); CDK7_IP, IB (Cell Signaling Technology, 2916s); CDK9_IP, IB (Cell Signaling Technology, 2316s); CDK12_IB (Cell Signaling Technology, 11973S); CDK13_IB (Sigma Cat. #ABE1860); Cyclin H_IB (Cell Signaling Technology, 2927T); HA_IP, IB (Cell Signaling Technology, 2367s); ERK1/2_IP, IB (Cell Signaling Technology, 9107s); phospho-ERK1/2_IB (Cell Signaling Technology, 9101s); phospho-Threonine_IB (Cell Signaling Technology, 9381s); PP2A alpha_IB (Abcam, ab32104); phospho-MED1_IB (Abcam, ab60950); Anti-GST_IB (Cell Signaling Technology, 2624); Anti-AKT_IB (Cell Signaling Technology, 9272); Anti-phosphoAKT_IB(Cell Signaling Technology, 4060); Anti-phospho-AR (Ser-515) _IB (Abeam, ab128250); Anti-RNA Pol 'LIB (Abeam, ab5408); Anti-phospho-pol II (Ser-5)_IB (Abeam, ab ab5095); Anti-phospho-CDK7 (Tlu-170) _IB (Millipore, ABS567); MED1_IP, IB, ChIP Seq (Bethyl, abA300-793A), Ki67_IHC (Cell Signaling Technology, 9661), and GAPDH (14C10), IB (Cell Signaling Technology, 3683s) for loading control. All antibodies were employed at dilutions suggested by the manufacturers.

For endogenous immunoprecipitation experiments, nuclear extracts were obtained from VCaP and LNCaP cells using NE-PER nuclear extraction kit (Thermo Scientific, 78835). Nuclear pellet was then lysed in IP buffer (20 mM Tris pH7.5, 150 mM NaCl, 1% Triton-X 100, Protease/Phosphatase Inhibitor) by sonication. Nuclear lysates (0.35-1.0 mg) were pre-cleaned by incubation with protein G Dynabeads (Life Technologies) for 1 h on a rotator at 4° C.

5 μg antibody was added to the pre-cleared lysates and incubated on a rotator at 4° C. overnight. Protein G Dyna-beads were then added for 1 h. Beads were washed twice in IP buffer, containing 300 mM NaCl, and resuspended in 40 μL of 2× loading buffer and boiled at 95° C. for 5 mM for separation of the protein and beads. Samples were then analyzed by SDS-PAGE and western blotting as described above.

PROTAC Studies

ARD-69, a highly Potent Proteolysis Targeting Chimera (PROTAC) degrader of androgen receptor (4), was used at a concentration of 100 nM for the set time points to analyze the effect of AR degradation on MED 1 phosphorylation and its recruitment to the chromatin through fractionation assay or western blotting as discussed above.

Kinase Assay

The kinase assay was performed by preparing the master mixture of 3 ul (5×) kinase assay buffer, 0.5 ul of 500 uM ATP (BPS Bioscience, 79603), 1.25 ul (1 ug/ul) Human Recombinant GST-MED1 protein (Lifespan Biosciences, LS-G59680-25), and 7.75 ul of kinase assay grade water per reaction for the desired number of reactions. To the test inhibitor control 2.5 ul of THZ1 (100 n M) was used. Additionally, kinase assay reaction mixtures containing no ATP and CDK7 were used as negative controls. Next, CAK complex-CDK7/CyclinH/MAT1 enzyme (BPS Bioscience) was thawed and diluted to (10 ng/111) in 1× kinase assay buffer. The reactions were initiated by adding 10 ul of diluted CAK complex to the designated wells and incubated at 30° C. for 60 min. After the incubation the reaction was stopped, and the mixture were analyzed through western blotting.

For luminescence-based CDK7 kinase activity analysis wild type MED1-peptide "SPAYTPQNLD" and mutant MED1-peptide "SPAYAPQNLD" (GenScript, U2051EC280_1, U2051EC280_3) were used. Following the above protocol, briefly after 60 min incubation, post addition of CAK complex, ADP-GLOW reagent (Promega, V6930) was thawed and 25 ul of the reagent was added to each well, the plate was covered with aluminum foil and incubated at room temperature (RT) for 45 min. After the incubation Kinase-Detection reagent (BPS Bioscience, 79603) was thawed and 50 ul of the reagent was added to each well and incubated for another 45 min at RT under dark conditions. After 45 min incubation luminescence was measured using the microplate reader (Note: in luminescence-based kinase assay, CAK-complex+CTD-peptide (BPS Bioscience)+ATP was used as a positive control, were as CAK complex+ Human MED1 protein without ATP was used as a negative control to subtract the background readings).

Phos-Tag SDS-PAGE

The electrophoretic mobility shift in phosphorylated pro-teins was studied by following the Manganese (II)-Phos-tag SDS-PAGE (FUJIFILM Wako Pure Chemical Corporation, 30493521) method as described previously. Following the specific treatment, the cells were subjected to lysate prepa-ration as mentioned above and analyzed through Phos-tag SDS PAGE. Briefly, a 3.5% (wt/vol) separating gel solution containing 50 μM polyacrylamide-bound Mn2⁺-Phos-tag and 0.5% (wt/vol) agarose and a stacking gel solution of 3.5% (wt/vol) containing 0.5% (wt/vol) agarose was pre-pared. The gel was run under constant-current conditions at room temperature for 3-4 h. Upon completion of the run the gel was removed and soaked in 100 ml of blotting buffer containing 1 mM EDTA for 10 min. Wet tank transfer apparatus equipment was used to transfer the proteins on PVDF.

Site Directed Mutagenesis pWZL hygro Flag-HA TRAP220 wt plasmid was used and purchased from Addgene (plasmid #17433). Primers were designed, and Site-directed mutagenesis was per-formed by the QuikChange II XL site-directed Mutagenesis Kit (Agilent Technologies, 200521). Two single mutants with point mutation T1032A and T1457A as well as a double mutant containing both T1032A and T1457A mutations were generated, using the manufacturer's protocol. All plas-mids were verified by DNA sequencing.

Primers used for mutagenesis are:

```
MED1 (T1032A) Fwd
                                (SEQ ID NO: 1)
5'-GTT CTT CTA ACA GAC CTT TTG CCC CAC CTA CCA
GTA C-3'

MED1 (T1032A) Rev
                                (SEQ ID NO: 2)
5'-GTA CTG GTA GGT GGG GCA AAA GGT CTG TTA GAA
GAA C-3' 3'

MED1 (T1457A) Fwd
                                (SEQ ID NO: 3)
5'-GCC ATA GTA AGT CAC CAG CAT ATG CCC CCC AGA
ATC TG-3' 3'

MED1 (T1457A) Rev
                                (SEQ ID NO: 4)
5'-CAG ATT CTG GGG GGC ATA TGC TGG TGA CTT ACT
ATG GC-3' 3'

MED1 (T1457D) Fwd
                                (SEQ ID NO: 5)
5'-GCC ATA GTA AGT CAC CAG CAT ATG ACC CCC AGA
ATC TG-3' 3'

MED1 (T1457D) Rev
                                (SEQ ID NO: 6)
5'-CAG ATT CTG GGG GTC ATA TGC TGG TGA CTT ACT
ATG GC-3' 3'
```

Gene Overexpression Studies

Plasmids expressing wt-MED1, T1032A-MED1, T1457A-MED1, T1457D-MED1, DM-MED1 (containing both T1032A and T1457A mutations) and pcDNA3-CDK7-HA were transfected into LNCaP cells with Lipofectamine 2000 (Invitrogen Life Technologies, 12566014) as per manufacturer's protocol. Cells were then harvested 48/72 h post-transfection and used in the overexpression assays, and subjected to western blotting or used for further experi-ments.

RNA Interference

For knockdown experiments, cells were seeded in six-well plates and transfected with 100 nM ON-TARGETplus SMARTpool siRNA (Dharmacon) targeting MED1 (Dhar-macon, L-004126-00-0005), CDK7 (Dharmacon, L-003241-00-0005), CDK9 (Dharmacon, L-003241-00-0005), CDK12 (Dharmacon, L-004031-00-0005), CDK13 (Dharmacon, L-004688-00-0005), PPP2AC (Dharmacon, L-003598-01-0005), AR (Dharmacon, L-003400-00-0005), MAPK1 (Dharmacon, L-003555-00-0005), AKT (Dharma-con, L-003000-00-0005) and non-targeting Pool as a nega-tive control (Dharmacon, D-001810-10-05) using lipo-fectamine RNAiMAX (Invitrogen, 13778150) according to the manufacturer's instructions. Individual siRNA's target-ing 3' UTR of MED1 (J-004126-10-0002) and CDK7 (Dhar-macon, J-003241-09-0002 and J-003241-10-0002) were also used. Cells were then harvested 48/72 h post-transfec-tion and used in cell proliferation, western blot analysis, qRT-PCR, and RNA-seq experiments.

39

RNA Isolation and Quantitative Real-Time PCR

Total RNA was isolated from cells using miRNeasy Mini Kit (Qiagen, 74106) and cDNA was synthesized from 1 μg total RNA using SuperScriptIV (Life Technologies, 18090200). qRT-PCR was performed using Fast SYBR Master Mix (Life Technologies, 4385617) or Taqman Fast Advance MMIX (Life Technologies, 4444964), and analyzed on QuantStudio3 (Applied Biosystems, USA). The target mRNA expression was quantified using ΔΔCt method, as normalized to GAPDH transcript levels. Primers were designed using Primer3 Input (version 0.4.0) (bioinfo.ut.ee/primer3-0.4.0/primer3) and synthesized by Integrated DNA Technologies.

The primer sequences for the SYBR green assays qPCR used are as follows:

```
zbtb16_qPCR_fwd_
                                (SEQ ID NO: 7)
CAGTTTTCGAAGGAGGATGC; 3' zbtb16_qPCR_rev_
                                (SEQ ID NO: 8)
CCCACACAGCAGACAGAAGA; 3' erg_qPCR_fwd_
                                (SEQ ID NO: 9)
CGCAGAGTTATCGTGCCAGCAGAT; 3' erg_qPCR_rev_
                                (SEQ ID NO: 10)
CCATATTCTTTCACCGCCCACTCC; 3' psa (klk3)_qPCR_fwd_
                                (SEQ ID NO: 11)
ACGCTGGACAGGGGGCAAAAG; 3' psa (klk3)_qPCR_rev_
                                (SEQ ID NO: 12)
GGGCAGGGCACATGGTTCACT; 3' tmprss2_qPCR_fwd_
                                (SEQ ID NO: 13)
CAGGAGTGTACGGGAATGTGATGGT; 3' tmprss2_qPCR_rev_
                                (SEQ ID NO: 14)
GATTAGCCGTCTGCCCTCATTTGT; 3' fkbp5_qPCR_fwd_
                                (SEQ ID NO: 15)
TCTCATGTCTCCCCAGTTCC; 3' fkbp5_qPCR_rev_
                                (SEQ ID NO: 16)
TTCTGGCTTTCACGTCTGTG; 3' slc45a3_qPCR_fwd_
                                (SEQ ID NO: 17)
TCGTGGGCGAGGGGCTGTA; 3' slc45a3_qPCR_rev_
                                (SEQ ID NO: 18)
CATCCGAACGCCTTCATCATAGTGT; 3' ar_qPCR_fwd_
                                (SEQ ID NO: 19)
CAGTGGATGGGCTGAAAAAT; 3' ar_qPCR_rev_
                                (SEQ ID NO: 20)
GGAGCTTGGTGAGCTGGTAG; 3' gapdh_qPCR_fwd_
                                (SEQ ID NO: 21)
TGCACCACCAACTGCTTAGC; 3' gapdh_qPCR_rev_
```

40

-continued
```
                                (SEQ ID NO: 22)
GGCATGGACTGTGGTCATGAG. 3'
```

RNA-seq Library Preparation and Sequencing

RNA-seq libraries were constructed using the TruSeq sample Prep Kit V2 (Illumina) according to the manufacturer's instructions. Briefly, 1 μg of purified RNA was poly-A selected and fragmented with fragmentation enzyme. After first and second strand synthesis from a template of poly-A selected/fragmented RNA, other procedures from end-repair to PCR amplification were performed according to the instructions given in the protocol. Libraries were purified and validated for appropriate size on a 2100 Bioanalyzer DNA 1000 chip (Agilent Technologies, Inc.). The DNA library was quantitated using Qubit and normalized to 4 nM prior to pooling. Libraries were pooled in an equimolar fashion and diluted to a final concentration of 1.8 pM. Library pools were clustered and run on Nextseq500 platform (Illumina Inc.) with single-end reads of 75 bases. The details of the various ChIP-seq experiment along with the corresponding read statistics are given in Table 1.

RNA-seq Analysis

Single-end sequencing reads were demultiplexed using Illumina bcl2fastq, quality checked using FASTQC (bioinformatics.babraham ac uk/projects/fastqc), and aligned to the GRCh37 (release 27) genome using the STAR v2.5.1 aligner, with default settings. The read statistics generated by STAR v2.5.1 was used to ensure that the aligned reads in all samples were over 90% of the total reads. The transcripts were assembled using cufflinks and the count and FPKM tables were computed using cuffnorm. Principal component analysis on the FPKM values was used to cluster the samples for further quality check.

Differential Gene Expression Analysis

Figure 9G:
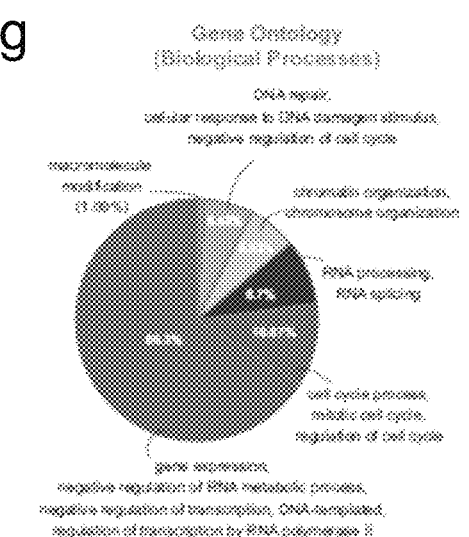
FIG. 9. Prostate cancer cells with hyperactive AR-signaling are sensitive to CDK7 inhibition. (a) GI$_{50}$ for THZ1 in a panel of eight PCa cell lines. (b) Immunoblot analysis of AR, p-MED1, MED1, CDK7 in six AR positive and four AR negative PCa cell lines, GAPDH was used as the loading control. (c) Colony formation assays in the presence of THZ1. Cells were cultured in the presence or absence of THZ1 for 12-14 days followed by staining (d) Annexin V-FITC staining showing percentage of apoptotic cells upon THZ1 treatment. (e) Immunoblot showing cleaved PARP and cleaved caspase-3 in cells treated with 200 nM THZ1 for 24 h. (f) Fold changes of differentially expressed genes determined by RNA-seq in cells treated with 100 nM THZ1 for 24 h. (g) Gene Ontology (GO) terms for genes down-regulated, by at least 4-fold, upon THZ1 treatment in VCaP and LNCaP cells. (h) GSEA network plot showing positively (red) and negatively (blue) enriched hallmark signature gene sets, as determined by GSEA with FDR q<0.1, in THZ1 treated VCaP and LNCaP cells. (i) Increased p-MED1 and reduced PP2A levels in AR driven Enzalutamide refractory PCa cells. Immunoblot analysis of indicated targets in four parental and enzalutamide resistant PCa cell lines. (j) Immunoblot analysis of p-MED1, MED1, PSA, cleaved PARP, cleaved caspase-3 in the four enzalutamide resistant PCa cell lines treated with vehicle or 200 nM THZ1 for 24 h. (k)

Genes differentially expressed between any two sets of treatment were determined using DESeq2 (bioconductor.org/packages/release/bioc/html/DESeq.html), a statistical tool that employs shrinkage estimates to compute fold changes. In all our calculations, the raw RNA-seq read counts from biological duplicates, for each treatment condition, was used as the input for DESeq2. Only genes that displayed at least 2-fold change in their expression levels, with an adjusted p-value <1e-10, were used for comparative analysis (FIGS. 3c, 7c, 8b, and 11a), curation of gene signatures for Gene set enrichment analysis (FIGS. 5j, 11d) and determination of gene ontology (FIG. 9g).

Gene Ontology Analysis

The Gene Ontology (GO) associated with a given set of genes was determined using the clueGO and cluepedia plugins for cytoscape. We specifically focused on the GO for biological processes (GO:BP), limited our analysis only to experimentally verified processes, and leveraged the integrated graphical tools in clueGO for our visualization needs. The results showed excellent agreement with gene ontologies obtained from other sources such as g:Profiler (biit.cs.ut.ee/gprofiler) and GO using the Panther Classification system (pantherdb.org).

Gene Set Enrichment Analysis

Functional class scoring of the all differentially expressed genes, against a given gene signature, was performed using the Gene set enrichment analysis (GSEA) tool, developed by the Broad Institute (www.software.broadinstitute.org/gsea). The Different Gene Sets Used for GSEA are as Follows:

Hallmark signatures (shown in FIGS. 1g, 9h, 3e, 8d, 11b, and 11c): The 50 hallmark gene sets were directly obtained from the molecular signature database msigDB maintained by the Broad Institute (software.broadinstitute.org/gsea/msigdb).

Signature for up-regulation of AR target genes (shown in FIG. 7E): Determined as genes commonly upregulated between VCaP and LNCaP, with at least 2-fold increase in expression levels and p<1e-10 (see middle panel in FIG. 7c). This 128 gene-signature consists of PGM3, TMCC3, APPBP2, PLPP1, TUBA3D, CAPZB, KIF22, ZCCHC6, LAT2, LRRFIP2, FKBP5, MRPS18A, SMS, NDFIP2, ABCC1, NDRG1, MTMR9, AGR2, BMPR1A, LRRC59, SNX25, TRIM3, CAMKK2, KRT18, SASH1, HMGCR, LIFR, HMGXB3, SSR3, ODC1, DHCR24, RHOU, UAP1, ELL2, PCMT1, SOCS2, CHRNA2, ORMDL2, PFKFB2, ACSL3, PMEPA1, SPDEF, SSR1, STEAP4, LDLR, GADD45G, SELENOS, FADS2, MICAL1, KCTD3, LRRC8A, HERC3, BMPR1B, SHROOM3, FGD4, IGFIR, PCTP, KLK3, MPC2, CREB3L4, MBOAT2, LRIG1, EAF2, SDK1, NSDHL, CSGALNACT1, VLDLR, GLUD1, ENDOD1, GLB1L2, ACAD8, THYN1, VPS27B, NCAPD3, PART1, MERTK, PRKCA, DBI, ITN, KCNMA1, CLDN8, ATAD2, PEX10, ELK4, SLC45A3, NBL1, AZGP1, CDC42EP3, FZD5, ATP1A1, SLC15A2, TMEM79, SSR2, KLF15, SEC11C, B2M, NNMT, NKX3-1, C19orf48, FASN, KRT8, EFCAB12, KLC2, DOLK, ZNF613, LDLRAD3, SSR4, MFSD5, C1orf116, TMEM50A, TMPRSS2, HIST2H2BE, ATP6V0A2, FAM174B, ANKRD37, INSIG1, C9orf152, MYBPC1, STK39, MTOR, UBE2J1, FICD, PTPRCAP, AMACR, ZNF350, OTUD7B, PRAG1, PAGR1.

Signature for down-regulation of AR target genes (shown in FIG. 7E): Determined as genes commonly downregulated between VCaP and LNCaP, with at least 2-fold decrease in expression levels and p<1e-10 (see lower panel in FIG. 7c). This 91 gene-signature consists of ITGA2B, MLXIPL, SAMD4A, DAPK2, RAI14, CDH3, MTHFD2, ASNS, GSDMB, RBMS2, NAALAD2, OPRK1, COL16A1, C20orf194, PYGL, RIMS4, OLFM2, BBC3, DBP, MAST1, EXPH5, ASIC1, NCOA7, STC2, SLC25A36, GADD45A, ADCY7, PMS2, SDC4, ATP8A1, TRERF1, KIAA1683, C1QTNF6, PSAT1, DOCK10, KIF12, SYTL2, SORL1, FRAS1, RNF165, MAP3K21, ACKR3, NR6A1, SESN3, CAPN5, DOC2A, ITPR1, SLC7A11, CNKSR3, TSPAN7, COLEC12, NAPEPLD, CAMK2N1, NFASC, ZNF503, SMAD3, MAPRE2, ATG16L2, GNG4, ENC1, TRIB1, NABP1, NR1D2, LPCAT4, PCED1B, MTURN, DDN, TNFSF15, CAPN12, TARSL2, AHNAK2, ZFP36L1, BTN3A2, MAPT, PLA2G2A, COLCA1, SRGAP3, JARS, SVIL, ATP6AP1L, POU5F1B, CCDC18-AS1, C5orf66, AC092902.2, PEG10, SRP14-AS1, PCAT1, RASSF5, AL355987.4, SRCIN1, MIR4697HG.

Signature for genes down-regulated upon ERG knock-down (shown in FIG. 11d): We used two different signatures to establish the down-regulation of ERG in THZ1 treated VCaP cells. The first is a 539 gene signature determined from the list of the DE genes (at least 2-fold change in expression levels) provided along with the microarray data in GSE58975. The second signature, consisting of 194 genes, was determined by differential gene expression of RNA-seq data for shNT and shERG from GSE110657. We only retained genes with at least 2-fold decrease in expression levels with p<1e-80 yielding the following 194 gene signature: ST7, SCIN, E2F2, ARHGAP6, COL9A2, HEXB, LAMC2, BCAS1, SLC9A3R2, SLC9A3, NUCB2, ST6GALNAC1, ACADVL, MCM2, ATP2A3, CA12, MGLL, CACNG4, WDR62, MCM6, REXO2, ITM2A, FAM234B, FTL, PIGS, FXYD3, MLF2, WDR7, TXNL1, SEL1L3, CDC45, BLNK, CRISP3, GGT1, SGSM3, SGK2, MYBL2, BMP7, MID1, ESRP1, NCALD, MCM4, ASAH1, SLC1A5, HPN, SIPA1L3, EPHB6, AGFG2, TSPAN13, AGR2, CORO2A, ENG, NPDC1, SH3PXD2A, CWH43, GALNT7, KLHL5, B3GAT1, KRT18, MGP, COPZ1, ERGIC1, HGD, ABCB6, SDC1, CAPZA1, TSPAN1, SLC36A1, SPDEF, MBOAT7, PPDPF, AIF1L, TSPAN8, VGF, SNRPN, SUMF2, FGF13, GDF15, MCCC2, PCNA, ATP8A2, NTS, REG4, YWHAQ, ANXA1, LAMC1, KLF4, RAB1A, MYOF, PPFIA2, APP, DOPEY2, KLK3, PRKACB, SLC39A1, CREB3L4, ILF2, TRPM8, GRIP2, EAF1, LIX1, ANO7, EGFR, CDCA5, SYTL5, GSN, MKI67, PLBD2, TMEM45B, PART1, AK5, ACSS1, PTPRN2, PCDH1, RAB11FIP1, ATAD2, MYO1E, ERG, COLEC12, SPON2, TFF1, SLC37A1, CSTB, LY6E, KIAA1522, S100A11, FSTL1, FBLN2, TGM4, S100P, ANXA5, RELL2, SHH, MID1IP1, SMCO4, MCM7, PSCA, KLK2, KRT80, TK1, SRRM2, RNF187, CRTAP, KRT8, CANT1, KCNK3, ENC1, RRM2, ID4, DAG1, JUP, MFSD4A, FZD4, CCNE2, SCUBE2, COX8A, MYO1D, TYMS, NAALADL2, ADAMTSL1, GATA2, BACE2, PYCR1, PCP4, DAZAP2, PTP4A2, SEPT9, LRRC26, FAM174B, AIDA, CYP4F12, VSIG10L, BCAM, PP7080, C9orf152, FAM111B, CLDN4, COLCA1, TUBB, ARRDC1, S100A10, PAPSS2, SCAMPS, SLC44A4, EML6, TSTD1, SNHG14, AC005077.4, UGT1A1, ARPIN, UGT1A3, TMEM141, PWAR6, SSTR5-AS1.

Apart from the commonly used gene set enrichment plot, we also represent our enrichment analysis using a GSEA network plot, as shown in FIGS. 9h, 3e, 8d, and 11b. These plots were generated from the analysis of the 50 hallmark signatures using an in-house python script based on the graph-tool library (graph-tool.skewed.de). Here, each signature is represented such that: (i) the size of the circle is directly proportional to its normalized enrichment score (NES), and (ii) the width of the line connecting any two signatures is directly proportional to the number of genes shared between them.

Chromatin-Bound Protein Extraction

Chromatin bound protein extraction was performed following the protocol described in Pawar et al. Briefly, 10 million cells were collected and washed with DPBS, and were resuspended in 250 μl Buffer A (10 mM HEPES pH 7.9, 10 mM KCl, 1.5 mM $MgCl_2$, 0.34 M sucrose, 10% glycerol, 1 mM DTT) supplemented with 0.1% TritonX-100 and incubated on ice for 10 min. The nuclei pellet was collected by centrifugation at 1300×g for 5 min at 4° C., washed in Buffer A and centrifuged again with the same settings. The nuclear pellet was then resuspended in Buffer B (3 mM EDTA, 0.2 mM EGTA, 1 mM DTT) and incubated on ice for 30 min. The chromatin pellet was collected by centrifugation at 1700×g for 5 min at 4° C., washed in Buffer B and centrifuged again with the same settings. The proteins were incubated on ice in Buffer B with 150 mM NaCl for 20 min and centrifuged at 1700×g for 5 min to remove proteins soluble in 150 mM salt concentrations. The pellet was then incubated in Buffer B with 300 mM NaCl on ice for 20 min and centrifuged again at 1700×g to obtain the final chromatin pellet. The chromatin pellet was dissolved in sample buffer, sonicated for 15 seconds, and boiled at 95° C. for 10 min. Samples were analyzed using Immunoblot analysis as described previously. All buffers were supplemented with Pierce protease inhibitor and Halt protease & phosphatase inhibitors.

Chromatin Immunoprecipitation (ChIP) and ChIP-seq

For ChIP-seq experiments, LNCaP and VCaP cells were serum starved, as mentioned earlier, for 72 h followed by 12 h treatment with 200 nM THZ1 or 10 μM MDV3100 in presence/absence 10 nM DHT. ChIP was performed using iDeal ChIP-seq Kit for Transcription Factors (Diagenode, C01010170) according to manufacturer's protocol. In brief, the cells were crosslinked with 1% formaldehyde in culture medium for 10 min at room temperature. Cross-linking was terminated by the addition of ⅟₁₀ volume 1.25 M glycine for 5 min at room temperature followed by cell lysis and sonication (Bioruptor, Diagenode), resulting in an average chromatin fragment size of 200 bp. Chromatin equivalent to $5\times10^6$ cells was isolated and incubated with 10 μg antibody overnight at 4° C. (MED1, H3-acetyl K27, AR, and IgG (Diagenode). ChIP-seq libraries were prepared from the ChIP-enriched DNA samples using the TruSeq ChIP Library Preparation Kit (Illumina, IP-202-1012, IP-202-1024) and protocol. In brief, ChIP-enriched DNA (1-10 ng) was converted to blunt-ended fragments. A single A-base was added to fragment ends followed by ligation of Illumina adaptors. The adaptor-modified DNA fragments were enriched by PCR using the Illumina Barcode primers and Phusion DNA polymerase. PCR products were size selected using 3% NuSieve agarose gels (Lonza) followed by gel extraction using QIAEX II reagents (QIAGEN). Libraries were quantified with the Bioanalyzer 2100 (Agilent) and sequenced on the Illumina NextSeq 500 Sequencer (75 nucleotide read length).

ChIP-seq Analysis

Sequencing reads were quality checked with FASTQC (www.bioinformatics.babraham.ac.uk/projects/fastqc) and aligned to the GRCh37 (release 27) genome using the STAR v2.5.1 aligner with default settings. PCR duplicate reads in the aligned bam files were removed using samtools, bam files were converted to CPM normalized bigwig tracks using deeptools, and viewed using the Integrated Genomics Viewer or the UCSC genome browser. Single end reads were extended up to the fragment length (200 bp) along the read direction. The details of the various ChIP-seq experiment along with the corresponding read statistics are given in Table 2.

Enrichment Analysis of ChIP-seq Data

The enrichment peaks for the various transcription factors and histone marks were computed using MACS2, with default settings. Regions found to ubiquitously enriched across a number of next-generation sequencing experiments, also known as the blacklisted peaks (sites.google.com/site/anshulkundaje/projects/blacklists), were excluded in all subsequent analysis.

Overlap of Enrichment Peaks

Figure 1B:
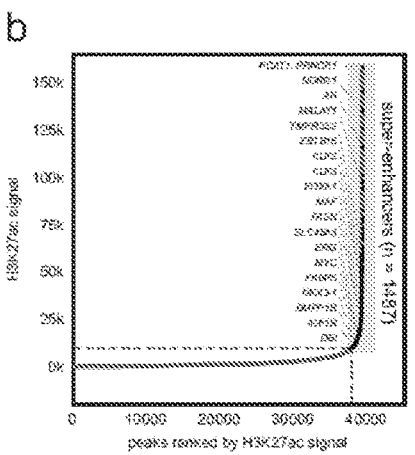
Figure 7A:
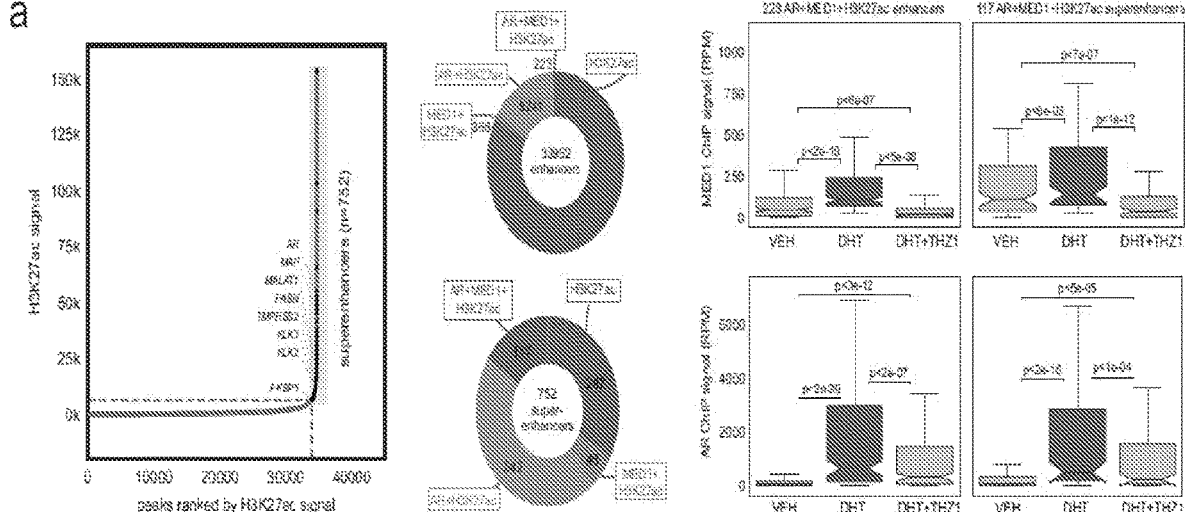
FIG. 7: CDK7 inhibition blocks MED1 chromatin recruitment and AR mediated transcription. (a) Left: Super-enhancer plot showing the 752 super-enhancers and 33952 enhancers in H3K27ac ChIP-Seq in LNCaP cells, Middle: Pie chart showing the overlap of AR and MED1 enrichment peaks with the H3K27ac enhancers and super-enhancers, and Right: MED1 and AR tag density in the 223 AR+MED1+H3K27ac enhancers and 117 AR+MED1+ H3K27ac super-enhancers regions, showing increased AR and MED1 binding upon DHT treatment and their reversal upon treatment with 200 nM THZ1 for 6 h. (b, c) Global transcriptome profiling by RNA-seq demonstrating the reversal of DHT induced transcriptome by THZ1. Total RNA from cells grown in steroid deprived media for 72 h followed by stimulation with 10 nM DHT with or without 100 nM THZ1 for 12 h was used for RNA-seq. Venn diagram displaying differentially expressed (DE) genes in VCaP and LNCaP cells, for DHT vs. DMSO (panel b) and DHT+THZ1 vs. DHT (panel c). (d) Heatmap displaying the effect of THZ1 inhibition of AR-signaling by completely reversing the expression levels of DHT-upregulated (top) and DHT-downregulated genes (bottom). Colors denote the z-score for the FPKM values. (e) GSEA plots for genes differentially expressed upon THZ1 treatment showing the complete reversal of genes commonly up- and down-regulated upon DHT-stimulation. (f) qRT-PCR analysis in LNCaP and VCaP cells, using total RNA from cells treated as in (b) and (c), showing complete reversal of DHT-induced AR target gene expression upon THZ1 treatment. Enzalutamide served as a positive control that displayed AR target reversal at 10 μM, demonstrating the higher efficacy of THZ1 in blocking AR-mediated transcription. Data showing mean±S.E. (n=3).
Figure 7D:
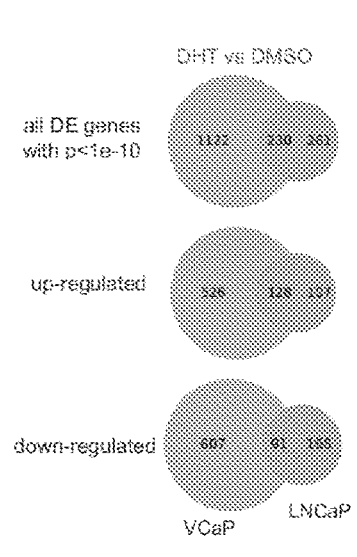
Figure 7D:
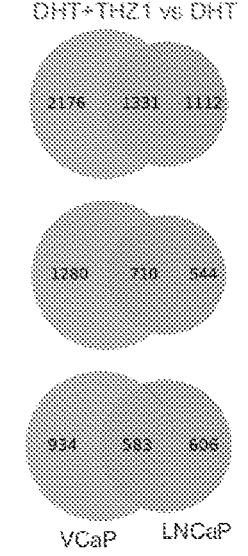
Figure 7D:
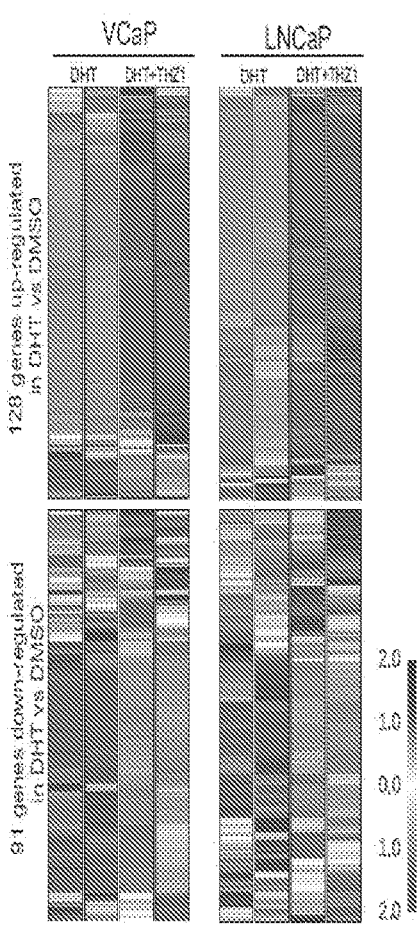
Figure 8C:
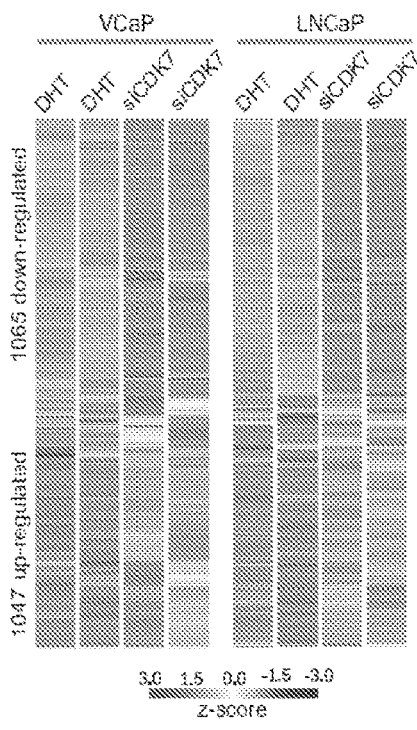
FIG. 8: CDK7 knockdown blocks AR-mediated transcription. (a) Immunoblot validation of CDK7 knockdown in LNCaP and VCaP cells grown in steroid-depleted media for 72 h followed by vehicle or 10 nM DHT stimulation for 12 h, with GAPDH as the loading control. Total AR shows no change upon CDK7 knockdown. (b) Venn diagram showing the degree of overlap between genes differentially expressed (DE) upon CDK7 knockdown in VCaP and LNCaP cells, as determined by RNA-seq. The left, middle and right panels correspond to all differentially-expressed, up-regulated, and down-regulated genes, respectively. (c) RNA-seq heatmap showing common differentially expressed genes upon CDK7 knockdown in VCaP and LNCaP cells. (d) GSEA network plot of the various msigDB hallmark signatures displaying positive (red) and negative (blue) enrichment, with a significance of FUR q<=0.05, in CDK7 knockdown LNCaP and VCaP cells. Here, the yellow and green outlines represent signatures enriched positively and negatively, respectively, in both cell lines. CDK7 knockdown leads to negative enrichment of the hallmark androgen response (indicated with bold green) in both cell lines.
Figure 8D:
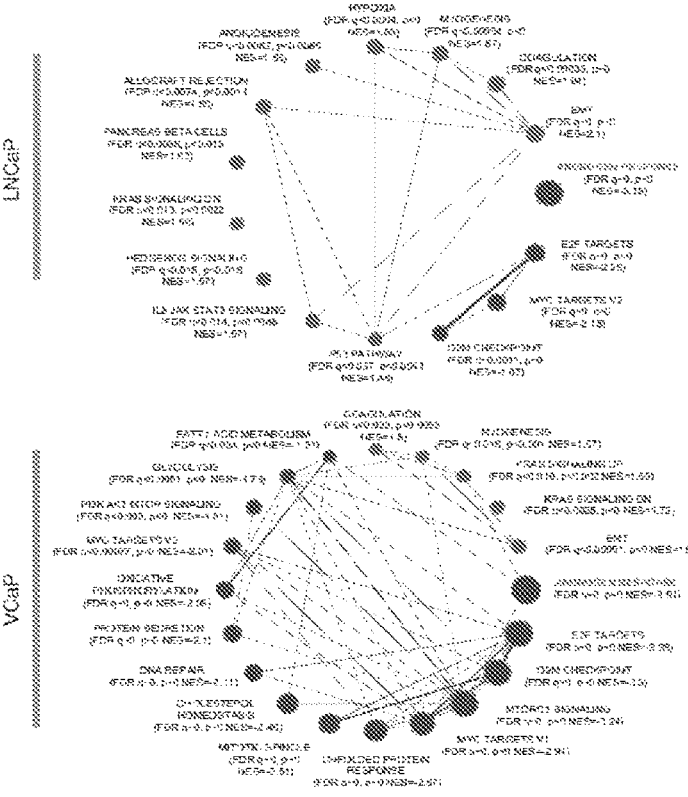

Overlap analysis of enrichment peaks in different samples was performed using an in-house python script. In our analysis, two peaks were considered to be overlapping even if they share a single base. The same overlap protocol was also followed to estimate the overlap between the AR and MED1 enrichment peaks with the H3K27ac enhancers and superenhancers, the statistics of which are shown in FIGS. 1b and 7a.

Determination of Super-Enhancers and ChIP Signal Under Super-Enhancers

The enrichment peaks were clustered into enhancers and super-enhancers using an in-house python script that closely follows the ROSE protocol for determining super-enhancers. Our code, which has been tuned for speed and multi-processing capabilities, essentially yield the same results as ROSE (bitbucket.org/young_computation/rose). The enrichment peaks and the super-enhancer regions were annotated using the annotation information provided with GRCh37 genome. In computing the ChIP signal in an enhancer/superenhancer region we only accounted for the signal from the enrichment peaks thereby effectively ignoring the background signal.

Motif Analysis of Enrichment Peaks

We used Centrimo, a statistical tool that performs motif discovery using the central motif enrichment analysis method, to analyze the enrichment of known transcription factor binding motifs in the vicinity of the AR and MED1 enrichment peaks. The positional weight matrices for over 680 human transcription factor motifs, used as the input to Centrimo, were obtained from the HOmo sapiens COmprehensive MOdel COllection (HOCOMOCO) database (hocomoco11.autosome.ru). We also performed de novo motif discovery using MEME-ChIP which also confirmed the massive enrichment of AR binding motifs in both AR enriched and AR and MED1 coenriched regions, similar to that shown in FIG. 2b.

Analysis of Tumor vs Normal Samples

Figure 2A:
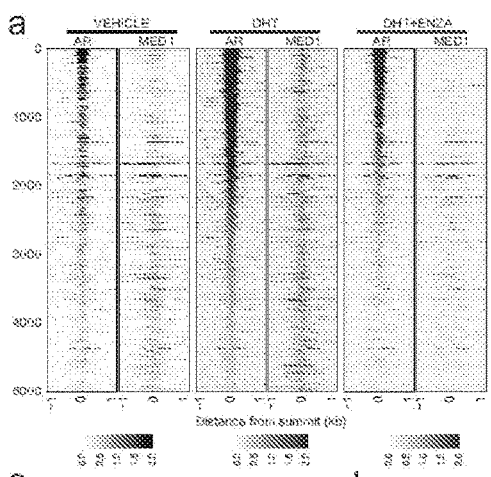
FIG. 2: ChIP-seq analysis reveal increased recruitment of AR and MEM to the super-enhancer regions in prostate cancer. (a) Heatmap representation of overlapping AR and MED1 ChIP-seq enrichment peaks in VCaP cells treated with vehicle, DHT, and DHT plus Enzalutamide (DHT+ENZA). The enriched peaks were rank-ordered based on the levels of AR and MED1 tag density within the −1 kb and +1 kb genomic region flanking the peak summit (b) Motif analysis of all genomic regions enriched in AR (left), MED1 (center), and co-enriched in AR and MED1 (right) showing the top 10 consensus motifs along with their p-values, as determined by Centrimo. The bottom panel shows the probability of finding the androgen receptor binding motif ANDR_HUMAN_H11M0.1.A, its motif sequence, and the percentage of peaks containing the mentioned motif. (c) Genome-wide averaged AR ChIP density in 7 normal (gray lines) and 13 prostate tumor tissue samples (red lines); symbols marked normal, and tumor represent the corresponding sample-averaged ChIP densities. (d) Violin plots showing the overlap between AR+MED1+H3K27ac regions (divided into 4,136 enhancers and 968 super-enhancers) in VCaP cells and AR enrichment peaks in 7 normal and 13 tumor samples. (e) Bar plot showing the overlap between the percentage of the 9181 T-ARBS and 2690 N-ARBS, that correspond to enriched AR binding sites in tumor and normal tissues, respectively, with AR+MED1+H3K27ac enhancers and super-enhancers. Rest refers to non-overlapping ARBS. (f) Average, per enrichment peak, AR-binding levels at genomic regions co-enriched in AR, MED1 and H3K27ac were calculated and subdivided into those overlapping with the 4136 AR+MED1+H3K27ac enhancers (top panel) and the 968 AR+MED1+H3K27ac super-enhancers (bottom panel). Here, normal and tumor (filled circles) refer to AR enrichment peaks in all normal and all tumor samples overlapping with the AR+MED1+H3K27ac enhancers and super-enhancers, and N-ARBS and T-ARBS (open squares) refer to AR-binding sites, previously identified using a differential analysis of normal and tumor tissue samples, overlapping with the AR+MED1+H3K27ac enhancers and super-enhancers. The per peak average signal in both the enhancers and super-enhancers are relatively higher compared to the global average in panel (c), while a noticeable enrichment in tumor samples is only seen for the super-enhancers. However, T-ARBS in both enhancers and super-enhancers display a higher enrichment compared to the corresponding N-ARBS. (g) AR ChIP-seq tracks in the vicinity of FKBP5 (left) and BMPR1B (right) for the 7 normal and 13 tumor samples, alongside AR, MED1, BRD4, and H3K27ac ChIP-seq in DHT-stimulated VCaP cells. The significance levels were estimated using a two-sided Mann-Whitney U-test.
Figure 2B:
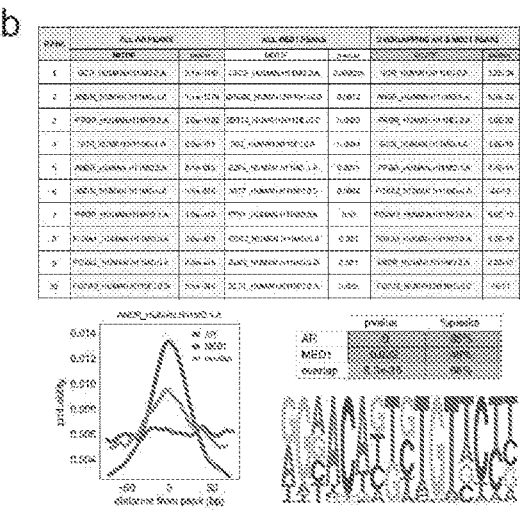
Figure 2C:
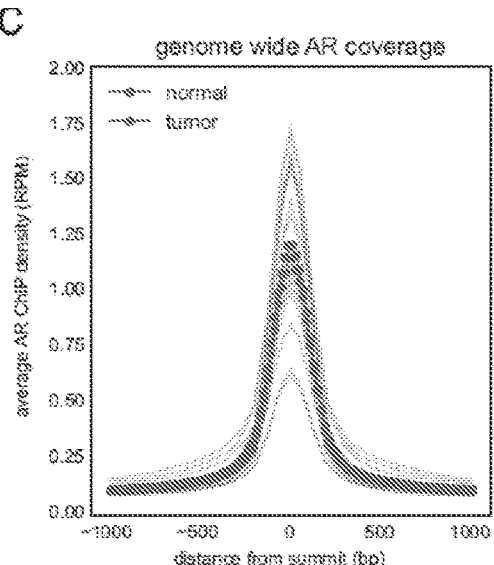
Figure 2D:
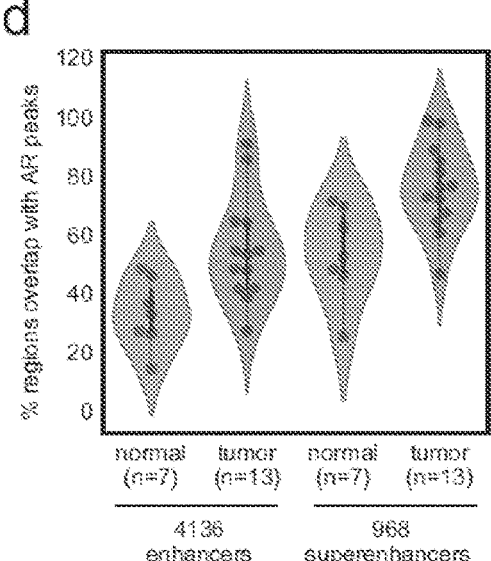
Figure 2G:
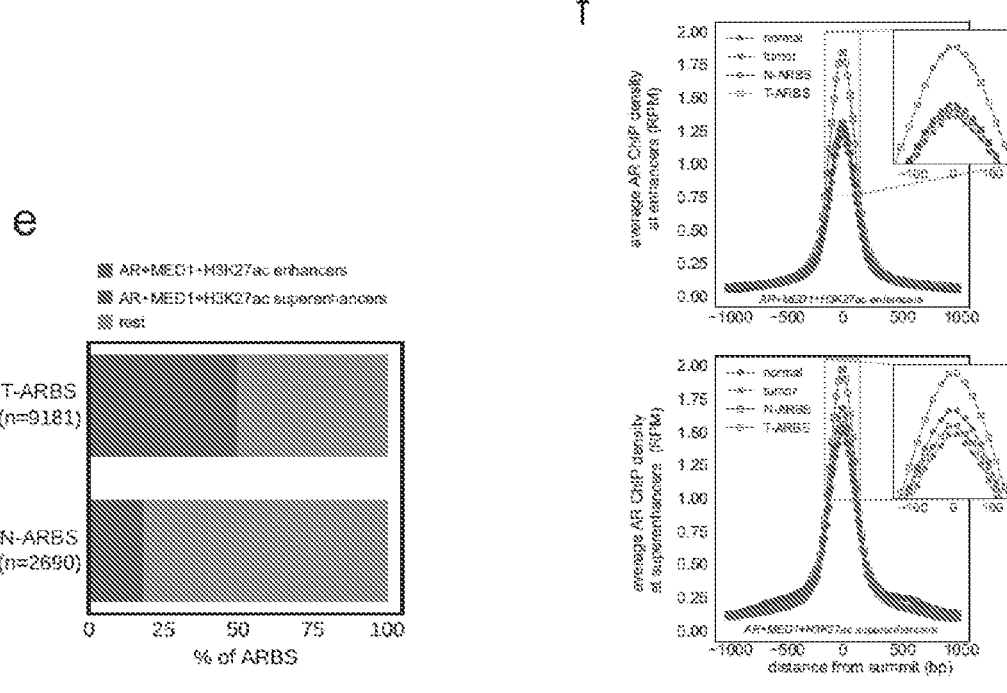

AR ChIP-seq data from 7 normal and 13 tumor tissue samples (GEO accession number GSE70079) were aligned and preprocessed as described. For each sample, we determined the group of enrichment peaks that overlapped with AR+MED1+H3K27ac enhancers and super-enhancers in VCaP cells (FIG. 1b). The distribution of the overlapping regions and the total ChIP signal contained in them are shown in FIGS. 2d and 1f, respectively. Pomerantz et. al. previously used an unsupervised clustering technique and identified 2690 AR binding sites in normal tissues (N-ARBS) and 9181 AR binding sites in tumor samples (T-ARBS). We performed an overlap analysis and identified the subset of N-ARBS and T-ARBS that were directly regulated by the AR+MED1+H3K27ac enhancers and super-enhancers.

Murine Prostate Tumor Xenograft Model

In vivo efficacy studies were performed in accordance with protocols approved by the Institutional Animal Care and Use Committee (IACUC) at the University of Pennsylvania and in compliance with all regulatory standards. Four to five-week-old male NOD SCID gamma mice (Jackson Lab, 005557) were procured from Jackson Laboratory. In the VCaP experiment, $2\times10^6$ VCaP prostate cancer cells suspended in 80 μL of RPMI-1640 with 50% Matrigel (BD Biosciences) were implanted subcutaneously into the dorsal flank of the mice. The animals were castrated when the tumor volumes reached approximately 150 mm³. After castration, once the tumor relapsed to 150 mm³, mice were randomized into two groups, treated with either 10 mg/kg body weight THZ1 or vehicle (D5W) intraperitonially b.i.d for 4 weeks. Tumor growth was recorded using digital calipers and tumor volumes were estimated using the formula $(\pi/6)(L\times W^2)$, where L=length and W=width of tumor. Body weight during the study was also monitored. At the end of the treatment regimen the mice were sacrificed and were extracted for further analysis.

Immunohistochemistry for Mouse Xenografts

Xenograft tumor pieces were fixed in 4% of formaldehyde for 48 h and paraffin embedded. Paraffin embedded sections from the tumors of treated and untreated mice were deparaffinized, rehydrated and subjected to epitope retrieval stained with a phospho-MED1 antibody (1:4000/1:2000), anti-PSA antibody (1:1000), anti-Ki67 (1:500), or anti-cleaved caspase3 antibody (1:1000) followed by peroxidase-based detection and counterstaining with hematoxylin using the Leica Bond Rxm system. Photographs were taken on a Leica DMI6000B inverted light and fluorescent microscope with a 20× objective. images were assessed and quantified in ImageJ.

Plasma PSA ELISA Assay

Whole blood of the xenograft bearing mice was collected with heparinized blood collecting tubes (Fisherbrand, 02-668-10), and cells were removed from plasma by centrifugation for 10 minutes at 2,000 g at 4° C. The plasma was used to detect PSA levels using the Human PSA ELBA Kit (Abeam, ab113327) following the manufacturer's protocol. In brief, we diluted the mice plasma ten time with Assay Diluent A, and LNCaP culturing media was used as a positive control. Serially diluted standards were used for quantification. 100 µL of each sample was loaded on the human PSA specific antibody coated 96-well plate in duplicates and the plate was incubated overnight at 4° C. to allow the PSA presented in samples to bind to the wells. The wells were then washed, and biotinylated anti-Human PSA antibody was added. After washing away unbound biotinylated antibody, HRP-conjugated streptavidin was added into the wells. The wells were again washed and developed with a TMB substrate solution followed by the addition of the stop solution and colorimetric measurement of the intensity at 450 nm. The concentrations of the PSA in the samples were calculated based on the standard curve.

TMA Analysis

Tumor sample containing slides were incubated at 60° C. for at least 2 h. Slides were then placed in EnVision FLEX Target Retrieval Solution, Low pH (Agilent DAKO, K800521-2) in a PT Link instrument (Agilent DAKO, PT200) at 75° C., heated to 97° C. for 20 min, and then cooled to 75° C. Following washing in IX EnVision FLEX Wash Buffer (Agilent DAKO, K800721-2) for 5 min slides were treated with Peroxidazed 1 (Biocare Medical. PX968M) for 5 min and Background Punisher (Biocare Medical, BP974L) for 10 min, with 5 min washes wash of 1× EnVision FLEX Wash Buffer for 5 min after each step. Rabbit polyclonal phospho-MED1 or AR diluted 1:500 in EnVision FLEX Antibody Diluent (Agilent DAKO, K800621-2) was added to each slide, which were then cover slipped with parafilm, placed in a humidifying chamber, and incubated overnight at 4° C. On the next day, slides were washed in 1× EnVision Wash Buffer for 5 min and then incubated in Mach2 Doublestain 1 (Biocare Medical, MRCT523L) for 30 min at room temperature in a humidifying chamber. The slides were rinsed in 1× EnVision Wash Buffer 3 times for 5 min each following by treatment with a Betazoid DAB solution (1 drop to iml buffer; Biocare Medical, BDB2004L) for 5 min. Slides were rinsed twice in distilled water, and treated with EnVision FLEX Hematoxylin (Agilent DAKO, K800821-2) for 5 min. Finally, the slides were rinsed several times in tap water, dried completely and dipped in xylene for approximately 15 times. EcoMount (Biocare Medical, EM897L) was added to each slide, which was then cover slipped.

TABLE 1

Table of replicate RNA-seq experiments used in this study, along wit]h statistics for the number of uniquely mapped reads (Related to RNA-seq library preparation and analysis).

| | | Replicate1 | | Replicate2 | |
|---|---|---|---|---|---|
| Cell line | Treatment | # unique mapped reads (million) | % of total reads | # unique mapped reads (million) | % of total reads |
| LNCaP | VEH | 12.66 | 87.80 | 19.81 | 87.86 |
| LNCaP | DHT | 18.46 | 87.67 | 12.5 | 88.17 |
| LNCaP | DHT + THZ1 (6 h) | 15.59 | 83.19 | 13.7 | 82.65 |

TABLE 1-continued

Table of replicate RNA-seq experiments used in this study, along wit]h statistics for the number of uniquely mapped reads (Related to RNA-seq library preparation and analysis).

| | | Replicate1 | | Replicate2 | |
|---|---|---|---|---|---|
| Cell line | Treatment | # unique mapped reads (million) | % of total reads | # unique mapped reads (million) | % of total reads |
| LNCaP | 24 h DMSO | 22.47 | 91.11 | 31.82 | 91.09 |
| LNCaP | 24 h THZ1 | 20.29 | 83.02 | 15.29 | 83.16 |
| VCaP | VEH | 17.21 | 86.94 | 12.21 | 85.81 |
| VCaP | DHT | 21.89 | 88.99 | 17.45 | 89.03 |
| VCaP | DHT + THZ1 (6 h) | 10.46 | 80.49 | 12.62 | 79.39 |
| VCaP | 24 h DMSO | 12.92 | 90.03 | 12.96 | 91.80 |
| VCaP | 24 h THZ1 | 10.55 | 87.89 | 9.51 | 85.27 |
| DU145 | 24 h DMSO | 22.33 | 90.55 | 26.91 | 90.18 |
| DU145 | 24 h THZ1 | 23.35 | 91.29 | 27.86 | 90.84 |
| LNCaP | DHT + siNT | 26.54 | 90.61 | 20.98 | 90.61 |
| LNCaP | DHT + siCDK7 | 19.45 | 82.71 | 16.51 | 82.25 |
| LNCaP | DHT + siMED1 | 21.62 | 81.05 | 19.1 | 79.92 |
| VCaP | DHT + siNT | 11.54 | 78.95 | 15.61 | 78.31 |
| VCaP | DHT + siCDK7 | 9.92 | 39.88 | 9.65 | 42.34 |
| VCaP | DHT + siMED1 | 9.81 | 47.51 | 10.17 | 48.83 |

TABLE 2

Table of ChIP-seq experiments/ChIP-seq data used in this study (Related to ChIP-seq library preparation and analysis).

| Cell line | Treatment | ChIP | # unique mapped reads (million) | % of total reads | GEO accession # |
|---|---|---|---|---|---|
| VCaP | VEH | AR | 32.33 | 87.40 | GSE55062 |
| VCaP | DHT | AR | 30.87 | 88.21 | GSE55062 |
| VCaP | DHT + ENZA | AR | 34.95 | 88.23 | GSE55062 |
| VCaP | DHT | BRD4 | 31.05 | 87.25 | GSE55062 |
| VCaP | DHT | H3K27ac | 22.37 | 71.06 | — |
| VCaP | VEH | MED1 | 28.87 | 76.47 | — |
| VCaP | DHT | MED1 | 26.64 | 76.29 | — |
| VCaP | DHT + ENZA | MEDI | 34.69 | 78.00 | — |
| VCaP | parental | H3K27ac | 29.65 | 92.79 | GSE96652 |
| VCaP | parental | H3K27ac | 32.1 | 92.87 | GSE96652 |
| VCaP | parental | H3K27ac | 24.62 | 92.83 | GSE96652 |
| LNCaP | VEH | AR | 67.36 | 89.02 | — |
| LNCaP | DHT | AR | 66.84 | 90.08 | — |
| LNCaP | DHT + THZ1 | AR | 57.24 | 88.43 | — |
| LNCaP | VEH | MED1 | 77.35 | 90.42 | — |
| LNCaP | DHT | MED1 | 54.22 | 90.78 | — |
| LNCaP | DHT + THZ1 | MED1 | 56.77 | 91.06 | — |
| LNCaP | parental | H3K27ac | 25.63 | 89.42 | — |
| tissue | normal | AR | — | — | GSE70079 |
| tissue | tumor | AR | — | — | GSE70079 |

TABLE 3

Table showing the primers reagents/kits, antibodies, siRNA, and drugs used
in this study (Related to Experimental Procedures)
Primer sequences for SYBR green PCR used in the study

| Gene | Forward Primer | Reverse Primer | Source |
|---|---|---|---|
| KLK3 | ACGCTGGACAGGGGGCAAAAG (SEQ ID NO: 23) | GGGCAGGGCACATGGTTCACT (SEQ ID NO: 24) | IDT |
| TMPRSS2 | CAGGAGTGTACGGGAATGTGATGGT (SEQ ID NO: 25) | GATTAGCCGTCTGCCCTCATTTGT (SEQ ID NO: 26) | IDT |
| FKBP5 | TCTCATGTCTCCCCAGTTCC (SEQ ID NO: 27) | TTCTGGCTTTCACGTCTGTG (SEQ ID NO: 28) | IDT |
| SLC45A3 | TCGTGGGCGAGGGGCTGTA (SEQ ID NO: 29) | CATCCGAACGCCTTCATCATAGTGT (SEQ ID NO: 30) | IDT |
| ZBTB16 | CAGTTTTCGAAGGAGGATGC (SEQ ID NO: 31) | CCCACACAGCAGACAGAAGA (SEQ ID NO: 32) | IDT |
| GAPDH | TGCACCACCAACTGCTTAGC (SEQ ID NO: 33) | GGCATGGACTGTGGTCATGAG (SEQ ID NO: 34) | IDT |
| AR | CAGTGGATGGGCTGAAAAAT (SEQ ID NO: 35) | GGAGCTTGGTGAGCTGGTAG (SEQ ID NO: 36) | IDT |
| ERG | CGCAGAGTTATCGTGCCAGCAGAT (SEQ ID NO: 37) | CCATATTCTTTCACCGCCCACTCC (SEQ ID NO: 38) | IDT |

Antibodies used in the study

| Antibody | Application | Source | Catalogue No |
|---|---|---|---|
| Anti-pS81-AR | IB | Millipore | 07-1375-EMD |
| Anti-AR | IB, IP, ChIP-seq | Millipore | 06-680-EMD |
| Anti-phosphor-MED1 | IB | Abcam | ab60950 |
| Anti-MED1 | IB, IP, ChIP-seq | Bethyl | abA300-793A |
| Anti-CDK9 | IB | Cell Signaling Technology | 2316S |
| Anti-PSA | IB | Daco North America | A0562 |
| Anti-CDK12 | IB | Cell Signaling Technology | 11973S |
| Anti-CDK12 | IB | Sigma | ABE1860 |
| HA | IB, IP | Cell Signaling Technology | 2367S |
| Cyclin H | IB | Cell Signaling Technology | 2927T |
| MAT1 | IB | Abcam | ab-1695-46 |
| Anti- cPARP | IB | Cell Signaling Technology | 9541S |
| Anti-RNA Pol II | IB | Abcam | ab5408 |
| Anti-ki67 | IHC | Cell Signaling Technology | 9661 |
| Anti-ERG | IB | Abcam | a92513 |
| Anti-CDK7 | IP, IB | Cell Signaling Technology | 2916s |
| Anti-phospho-CDK7 (Thr-170) | IB | Millipore | ABS567 |
| Anti-Rabbit (peroxidase conj.) | IB | Thermo Fisher Scientific | 0032460 |
| Anti-Mouse (peroxidase conj.) | IB | Thermo Fisher Scientific | 0032430 |
| Anti-ERK1/2 | IB | Cell Signaling Technology | 9107s |
| Anti-phospho-ERK1/2 | IB | Cell Signaling Technology | 9101s |
| Anti-phospho-Threonine | IB | Cell Signaling Technology | 9381s |
| Anti-PP2A alpha | IB | Abcam | ab32104 |
| Anti-H3-acetyl K27 | ChIP-seq | Abcam | ab4729 |

-continued

Antibodies used in the study

| Antibody | Application | Source | Catalogue No |
|---|---|---|---|
| Anti-Cleaved caspase-3 | IB | Cell Signaling | 9664t |
| Anti-GAPDH (14C10) | IB | Cell Signaling Technology | 3683S | siRNA used in the study

| siRNA | Source | Catalogue No |
|---|---|---|
| siMED1 | Dharmacon | L-004126-00-0005 |
| siCDK7 | Dharmacon | L-003241-00-0005 |
| siCDK9 | Dharmacon | L-003241-00-0005 |
| siCDK12 | Dharmacon | L-004031-00-0005 |
| siCDK13 | Dharmacon | L-004688-00-0005 |
| siPPP2CA | Dharmacon | L-003598-01-0005 |
| siAKT | Dharmacon | L-003000-00-0005 |
| siMAPK1 | Dharmacon | L-003555-00-0005 |
| siCDK7 | Dharmacon | J-003241-09-0002 |
| siCDK7 | Dharmacon | J-003241-10-0002 |
| siCDK7 | Dharmacon | J-004126-10-0002 |
| siNT | Dharmacon | D-00 1810-10-05 |

Drugs used in the study

| Drug | Source | Catalogue No |
|---|---|---|
| THZ1 | MedChem Express | HY-80013A/ CS-3168 |
| THZ1R | MedChem Express | MedChem Express |
| LDC000067 | Selleckchem | S7461 |
| Trametinib | Selleckchem | S2673 |

-continued

Drugs used in the study

| Drug | Source | Catalogue No |
|---|---|---|
| Dinaciclib | Selleckchem | S2768 |
| 5α-Dihydrotestosterone | Cerilliant | D-073 |
| EGF | Thermo Fisher Scientific | PHG0311L |
| MK2206 | MedChem Express | HY-10358 |

Cell lines used in the study (All cell lines were obtained from ATCC, otherwise specified)

| Cell line | Origin | Tissue | Catalogue No |
|---|---|---|---|
| LNCaP | *Homo sapiens*, human | prostate | CRL-1740 |
| VCaP | *Homo sapiens*, human | prostate | CRL-2876 |
| 22RV1 | *Homo sapiens*, human | prostate | CRL-2505 |
| LAPC4 | *Homo sapiens*, human | prostate | CRL-13009 |
| PC3 | *Homo sapiens*, human | prostate | CRL-7934 |
| DU145 | *Homo sapiens*, human | prostate | HTB-81 |
| RWPE | *Homo sapiens*, human | prostate | CRL-11610 |
| LNCaP-AR-KO | Derived from LNCaP (AR knockout) | prostate | |
| LNCaP-AR | Derived from LNCaP (Over expressing AR) | prostate | |
| LNCaP-AR-957L | Derived from LNCaP-AR (Enzalutamide Resistant) | prostate | |
| LNCaP-MDVR | Derived from LNCaP (Enzalutamide Resistant) | prostate | |
| LAPC4-MDVR | Derived from LAPC4 (Enzalutamide Resistant) | prostate | |
| VCaP-380R | Derived from Vcap (Enzalutamide Resistant) | prostate | |

Reagents/kits used in the study

| Item | Source | Catalogue No |
|---|---|---|
| RNA library preparation kit | Illumina | |
| ChIP Seq kit | Diagenode | C01010055 |
| NE-PER nuclear and cytoplasmic protein extraction kit | Thermo scientific | 78835 |
| Annexin V FITC kit | Sigma | APOAF-20TST |
| miRNeasy Mini Kit | Qiagen | 74106 |
| SuperScriptIV | Life Technologies | 18090200 |
| SYBR Master Mix | Life Technologies | 4385617 |
| Taqman Fast Advance MMIX | Life Technologies | 4444964 |
| Cell titer glow reagent | Promega | G7572 |
| Phos-tag (TM) Acrylamide AAL-107 | FUJIFILM Wako Pure Chemical Corporation | 30493521 |
| RNAiMAX | Invitrogen | 13778150 |
| Pierce Protease Inhibitor Tablets | Thermo scientific | A32965 |
| Halt Protease and Phosphatase Inhibitor Cocktail | Thermo scientific | 1861280 |
| Dyna beads protein G | Invitrogen | 10004D |
| Lipofectamine ™ 2000 CD Transfection Reagent | Invitrogen | 12566014 |
| Tween-20 | Thermo scientific | TA-125-TW |
| DTT | Thermo scientific | 707265ML |
| PSA ELISA Kit | Abcam | ab113327 |

Results

Figure 1C:
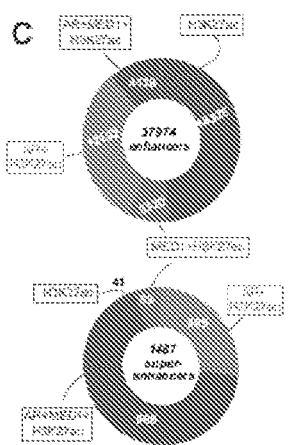
Figure 1D:
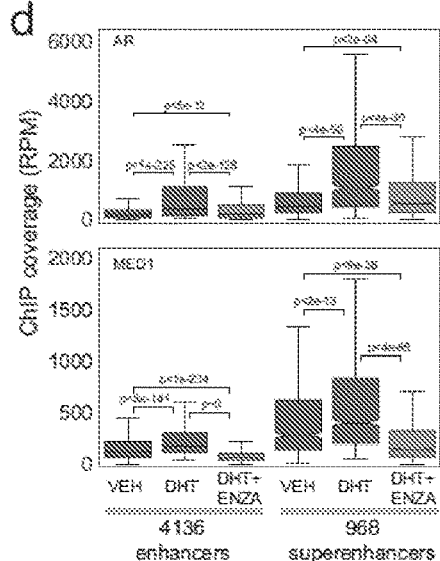

To systematically evaluate the significance of MED1 in establishing the ligand-dependent AR-cistrome and subsequent transcriptional amplification in PCa cells, we determined by ChIP-seq the genome-wide enrichment of MED1 and AR upon androgen (Dihydrotestosterone—DHT) stimulation in VCaP cells. We utilized VCaP cells, as this PCa cell line harbors AR genomic amplification found in greater than 85% of metastatic CRPC patients. As we reported previously, the average ChIP-seq signal for AR was highly enriched in DHT-treated cells, and this signal is significantly reversed with enzalutamide (FIG. 1a). Interestingly, MED1 also displayed increased chromatin association upon DHT stimulation, which was completely abolished by enzalutamide (FIG. 1a). This apparent trend may be attributed to the co-recruitment of AR and MED1 (FIG. 2a) to 5,014 regions that are highly enriched in Androgen Responsive Elements (FIG. 2b). To examine the nature of AR and MED1 bound sites, we first identified transcriptionally active regions using H3K27ac ChIP-seq in VCaP cells. This provided 93,004 regions clustered into 37,974 enhancers and 1,487 super-enhancers, which are clusters of enhancers densely occupied by transcription factors, cofactors, and chromatin regulators and display a wide variety of chromatin modifications, typically formed by gene amplification, translocation or transcription factor overexpression (FIG. 1b). Super-enhancers (SEs) have been found to play a significant role in the maintenance of cell-type specific gene expression patterns. Interestingly, these super-enhancer regions in VCaP cells are positioned within 100 kb of many AR-regulated coding genes and lncRNAs, including canonical AR targets such as TMPRSS2, KLK3, ZBTB16, SLC45A3, PCAT1, and PRNCR1, thus implicating these distal regulatory regions in AR transcriptional output. Our integrative analysis of H3K27ac, AR, and MED1 ChIP-seq data further exemplifies this point, wherein 92% of the super-enhancers but only 43% of the enhancers, were enriched in AR (AR+H3K27ac), while more strikingly 65% of the super-enhancers, compared to 11% of the enhancers, are co-enriched for both AR and MED1 (AR+MED1+H3K27ac) (FIG. 1c). We also found AR and MED1 enrichment to be significantly higher in the 968 super-enhancer regions when compared to the 4136 enhancer regions (FIG. 1d). These observations together clearly establish that ligand-dependent AR activation results in robust co-recruitment of AR and MED1 to super-enhancers, resulting in amplified expression of associated target genes, as exemplified by ChIP-seq tracks shown for FKBP5 (FIG. 1e). We next analyzed AR ChIP-seq data from normal and primary prostate tumors to ascertain whether AR recruitment to super-enhancers is elevated during tumor development. While no considerable difference was observed in the genome-wide AR binding levels between the tumor and normal (FIG. 2c), the tumor tissues displayed a pronounced enrichment of AR in the super-enhancer regions (FIG. 1f). In addition, 70-90% of the AR+MED1+H3K27ac superenhancers in VCaP, a cell line originally derived from vertebral metastasis, overlapped with AR enriched regions in primary tumors (FIG. 2d-g). These data suggest that a large number of AR-bound super-enhancers in the primary tumor may continue to be enlisted upon progression to metastasis via MED1 association to support super-enhancer/promoter long-range interactions required for transcriptional amplification.

Figure 26A:
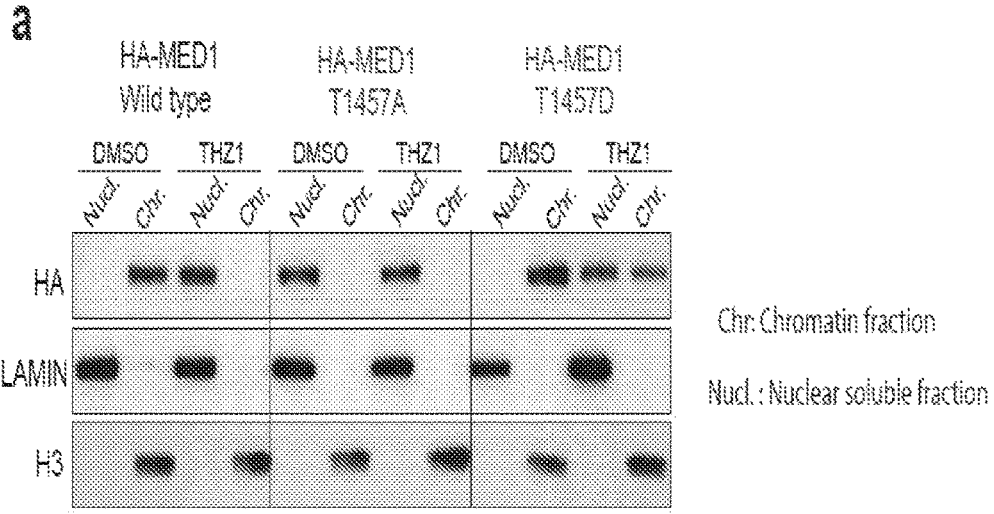
Figure 26B:
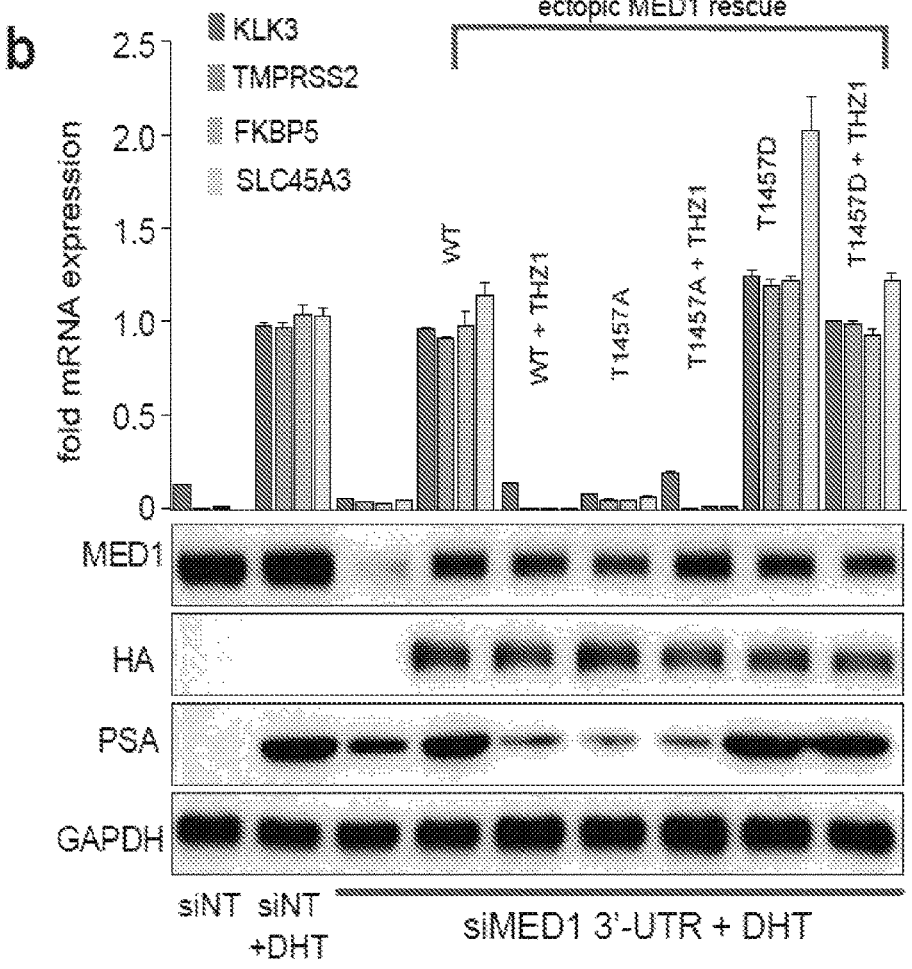

Since AR and MED1 interactions are highly localized to the super-enhancer regions, we hypothesized that MED1 recruitment to AR-target gene loci is pivotal for AR-transcriptional activity and that modulation of MED1 expression or activity could provide a novel route to resolve AR-dependent transcriptional addiction in PCa. To test this, we performed MED1 knockdown in LNCaP and VCaP cells and observed a complete reversal of DHT-induced transcriptional changes without affecting AR expression (FIG. 3a-d). Additionally, to address the effects of MED1 depletion on SE associated genes, we attempted to integrate the ChIP-seq and RNA-seq data from VCaP cells. First, we analyzed and found that the magnitude of expression of genes (FPKM values from RNA-seq) associated with AR+MED1+ H3K27ac containing enhancers and SEs were higher than that for the MED1+H3K27ac containing enhancers and SEs genes (FIG. 23A). Second, we found a significantly higher expression of genes associated with AR+MED1+H3K27ac containing superenhancers compared to AR+MED1+ H3K27ac enhancers (p<1e-05), suggesting that the MED1-AR interaction at SEs elicits much higher transcription of associated genes (FIG. 23A). Third, MED1 depletion led selective, significant decrease in the expression of genes associated with SEs containing AR+MED1+H3K27ac (p<6e-133), whereas genes marked with MED1+H3K27ac SE did not display any significant difference in expression (p<1e-01) (FIG. 23A). Importantly, Gene set enrichment analysis (GSEA) of the differentially expressed genes showed a highly significant negative enrichment of the Hallmark Androgen Response and growth associated transcriptional signatures (FIG. 1g and FIG. 3e and FIG. 26B). Together, these findings provide clear evidence for the integral role of MED1 in enhancer and SE associated AR target gene expression in prostate cancer.

MED1 Phosphorylation is Required for its Interaction with AR

Next, we investigated whether ligand-dependent AR activation leads to MED1 phosphorylation, which might promote its recruitment into the Mediator complex thereby facilitating chromatin binding. Using the Phos-tag immunoblot assay, in which the di-nuclear metal complex (1,3-bis [bis(pyridin-2-ylmethyl)amino]propan-2-olato dizinc(II)) specifically binds to phosphorylated amino acids and generates a mobility shift on acrylamide gels proportional to the number of incorporated phosphates, which detects phosphorylated forms of proteins, we observed two additional slow migrating bands for MED1 in nuclear extracts from cells stimulated with DHT, compared to vehicle control, which were eliminated upon phosphatase (CIAP) treatment (FIG. 1h). Phosphorylation of Threonine1032 (T1032) and Threonine1457 (T1457) of MED1 has been shown to promote its association with RNA Poll and other Mediator subunits, inducing chromatin looping by increasing recruitment of transcription factors and co-activators on chromatin. We confirmed that the DHT-induced MED1 phosphorylation sites are indeed these two previously observed threonine residues by performing HA-pulldown followed by phospho-Threonine (p-Thr) immunoblotting and a Phos-tag assay in LNCaP cells overexpressing HA-tagged wild type, T1032A, T1457A or double mutant (DM) MED1 (FIG. 1i and FIG. 4a). Interestingly, Phos-tag analysis of the T1457A mutant displayed a complete loss of phosphorylation on T1032 (FIG. 4b) and both the T1457A and DM MED1 mutants showed impaired associated with AR, suggesting that T1457 directed phosphorylation is a critical step required for the assembly of the AR-MED1 complex (FIG. 1i). Next, using the p-T1457 specific antibody (FIG. 4b) that does not detect the T1457A mutant, we observed a time-dependent increase in p-MED1 levels upon DHT stimulation with a concomitant increase in the expression of phosphoSer81-AR (p-AR), an active chromatin bound form of AR, suggesting a ligand-dependent phosphorylation of MED1 in AR positive PCa (FIG. 1j and FIG. 4c). In agreement, AR null LNCaP cells stimulated with DHT displayed no such increase in p-MED1 levels (FIGS. 4d and 24C). Reciprocal immunoprecipitation for MED1 and AR confirmed their ligand-induced phosphorylation-dependent interaction as shown by the complete loss of interaction when nuclear lysates were treated with CIAP (FIG. 1k). Our findings that p-MED1 is a key regulator of AR transcription led us to reason that p-MED1 might also be associated with PCa progression defined by increased AR signaling. To test this hypothesis and access the feasibility of p-MED1 as a prognostic marker, we analyzed prostate cancer tissue microarrays (TMA) containing benign adjacent (n=48), primary (n=228) and metastatic (n=96) prostate tumor samples, and found a progressive increase in nuclear p-MED1 levels from benign, localized, and metastatic sites (p<3e-12, p<1e-15 and p<4e-06) (FIGS. 1l and 1m and 24D-24E). These results are in agreement with our in vitro findings and provide a molecular basis for the use of p-MED1 as both a prognostic marker for advanced prostate cancer and as a therapeutically targetable activator of AR signaling for the treatment of PCa.

CDK7 Directly Phosphorylates MED1 at T1457

Figure 5B:
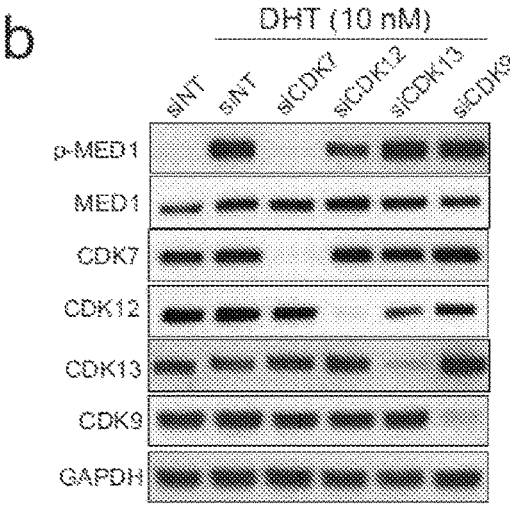
FIG. 5: CDK7 phosphorylates MED1 and its inhibition by THZ1 disrupts co-recruitment of AR and MED1 to the chromatin. (a) THZ1 blocks MED1 phosphorylation. Immunoblot analysis showing the levels of the indicated proteins in PCa cell lines treated with DMSO or TRA (trametinib—MEK inhibitor), LDC000067 (CDK-9 inhibitor), DIN (Dinaciclib—panCDK inhibitor), THZ1 (CDK7/12/13 inhibitor) for 24 h. p-ERK was used as positive control for TRA. (b) Knockdown of CDK7 affects DHT-induced p-MED1. Proteins extracted from LNCaP cells transfected with indicated siRNA and grown in steroid-depleted media for 48 h followed by treatment with vehicle or 10 nM DHT for 12 h were used. (c, d) Reciprocal co-IP analysis using nuclear lysates from LNCaP and VCaP cells with MED1 and CDK7 specific antibodies, demonstrating the interaction between MED1 and CDK7 in the transcriptional complex consisting of cyclinH, MAT1, RNA PolII and AR. (e) Left, THZ1 treatment leads to disruption of MED1-AR interaction. IP followed by immunoblotting, using nuclear extracts from cells treated with DMSO or 100 nM THZ1 for 6 h. Right, schematic depicting the disruption of MED1 and AR interaction by THZ1. (f) Immunoblot analysis demonstrating the loss of chromatin bound MED1 (p-MED1) upon THZ1 treatment. Chromatin, nuclear and cytoplasmic fractions from LNCaP cells that were serum starved for 3-days following stimulation with DHT and/or treatment with DMSO or THZ1 (100 nM) for 6 h were used to probe the indicated proteins. Enzalutamide at 5 μM was used as a direct anti-AR (g) Genome-wide averaged AR and MED1 ChIP-seq enrichment in LNCaP cells grown as in (f). (h) Heatmap representation of AR and MED1 overlapping ChIP-seq peaks in different treatment groups. (i) THZ1 treatment effectively blocks AR and MED1 recruitment to super-enhancers leading to reduced transcription of AR-target genes. ChIP-seq tracks, for AR and MED1, alongside RNA-seq tracks, on the KLK2, KLK3 and KLK4 locus for DHT-stimulated LNCaP cells in absence/presence of THZ1. H3K27ac ChIP-seq data and the super-enhancer associated with this region (displayed as a black bar in bottom left) are also shown.
Figure 5E:
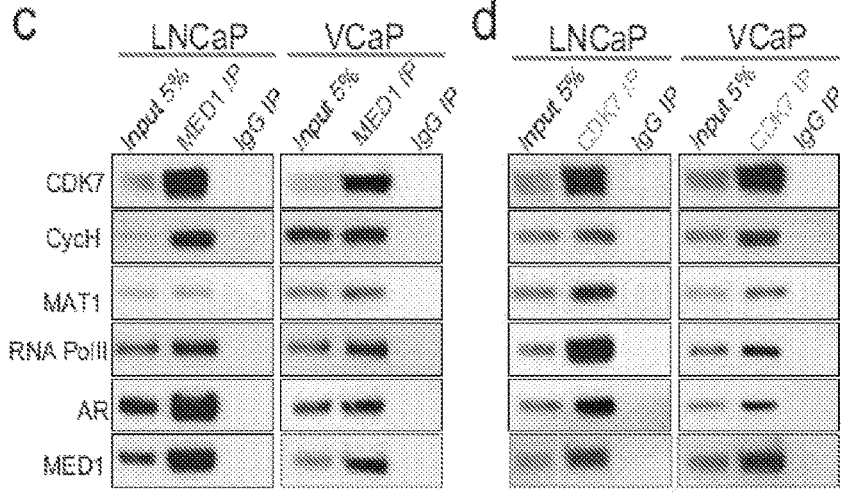
Figure 5E:
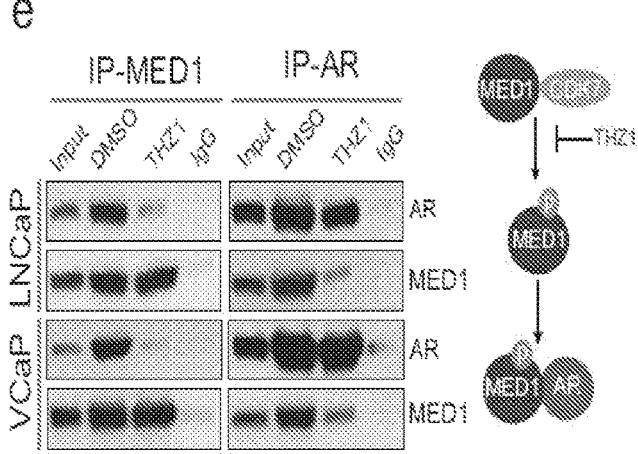
Figure 6C:
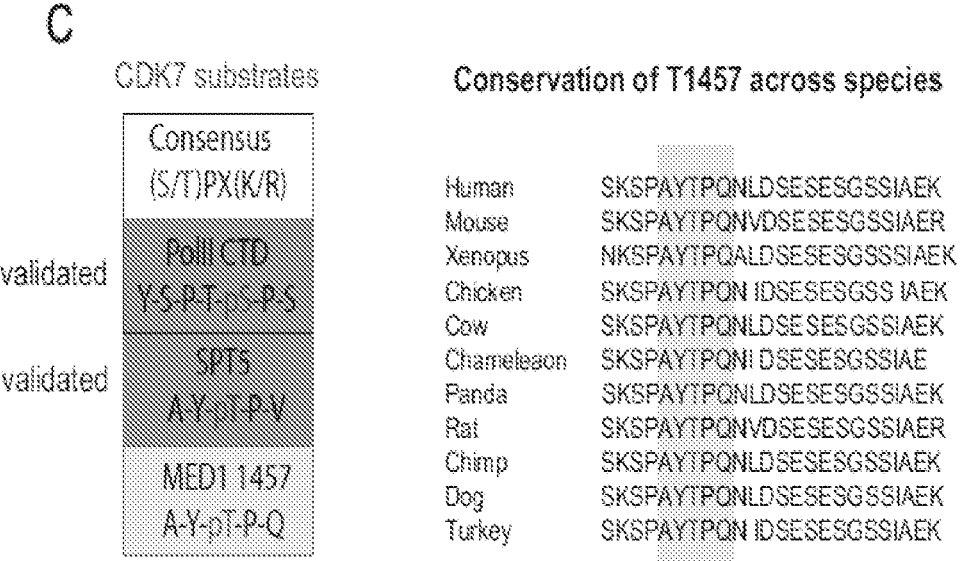
FIG. 6: CDK7 phosphorylates MED1 at T1457: (a) THZ1 treatment abolishes DHT-induced MED1 phosphorylation. Immunoblots showing the levels of p-MED1 and total MED1 in PCa cells grown in steroid deprived media for 72 h followed by stimulation for 12 h with 10 nM DHT in the presence of dmso or TRA (trametinib—MEK inhibitor), LDC (CDK-9 inhibitor), DIN (Dinaciclib—pan-CDK inhibitor), and varying concentrations of THZ1 (CDK7 inhibitor). p-ERK was used as positive control for trametinib treatment and GAPDH was used as loading control. (b) Knockdown of CDK7 significantly reduces DHT-induced MED1 phosphorylation and PSA expression. LNCaP cells were transfected with siNT or siMED1 and grown in steroid deprived media for 72 h followed by stimulation with 10 nM DHT for 12 h. THZ1 was used as positive control and GAPDH served as loading control. Total protein extracted was used for immunoblotting for the indicated target proteins. (c) Left: Comparison of the consensus CDK7 substrate (Ser/Thr-Pro-X-Lys/Arg, where X represents any possible residue) [SEQ ID NO:39] to well-established CDK7 target phosphorylation sites: the Tyr-Ser-Pro-Thr-Ser-Thr-Ser (SEQ ID NO:40) heptapeptide region in RNA Pol II C-Terminal Domain (CTD) and Thr-Pro dipeptide sequence in the transcription elongation factor SPTS. The T1457 in MED1 shows similarity with SPTS site and is indicated in red, and Right: Conservation of T1457 sequence motifs across species. The T1457 site is embedded in an IDR (Intrinsically disordered region) previously shown to be associated with the phase-separation property of MED1. (d) Protein feature view from RSCB protein data bank (www.rscb.org/pdb) showing the predicted phosphorylation sites (the green dot denotes the T1457 residue) and the degree of disorder (blue represents ordered regions, and red represents potentially disordered regions) in Homo Sapiens MED1 (uniprot accession ID: Q15648). (e) Phos-tag analysis showing the loss of DHT induced MED1 phosphorylation upon treatment with THZ1. The cells were treated with THZ1 (200 nM, 12 h) under starved or DHT stimulated conditions followed by nuclear protein extraction. For CIAP treatment nuclear fractions were treated with or without calf intestine alkaline phosphatase (CIAP) before Phos-tag SDS-PAGE and immunoblotting with MED1 antibody. Control immunoblots were done on standard gels with MED1 and GAPDH antibodies. (f) same as in e with cells transfected with siNT or siCDK7. (g) and (h) THZ1 reduces p-MED1 in a dose and time-dependent manner. Immunoblot showing dose- and time-dependent effect of THZ1 on p-MED1 expression in the indicated cell lines grown in standard growth conditions.
Figure 6D:
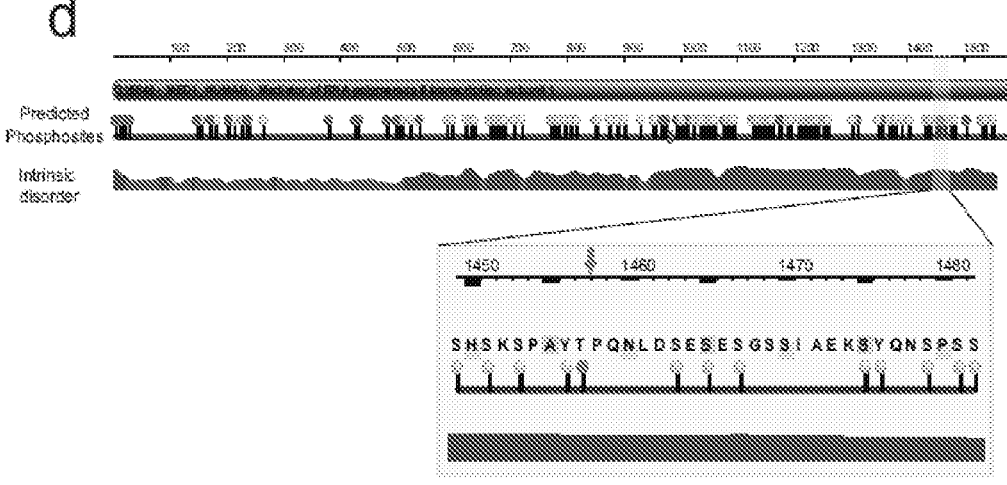
Figure 6H:
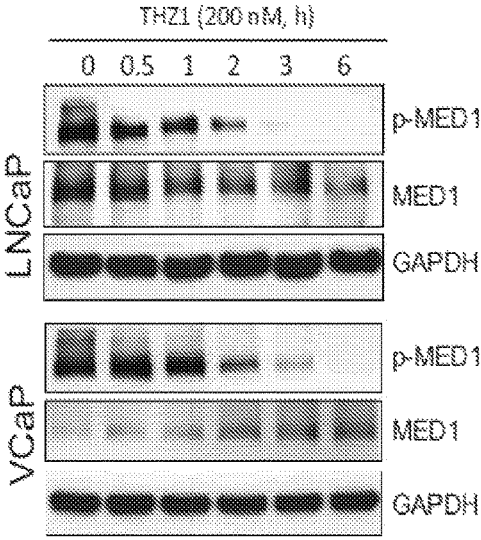
Figure 19D:
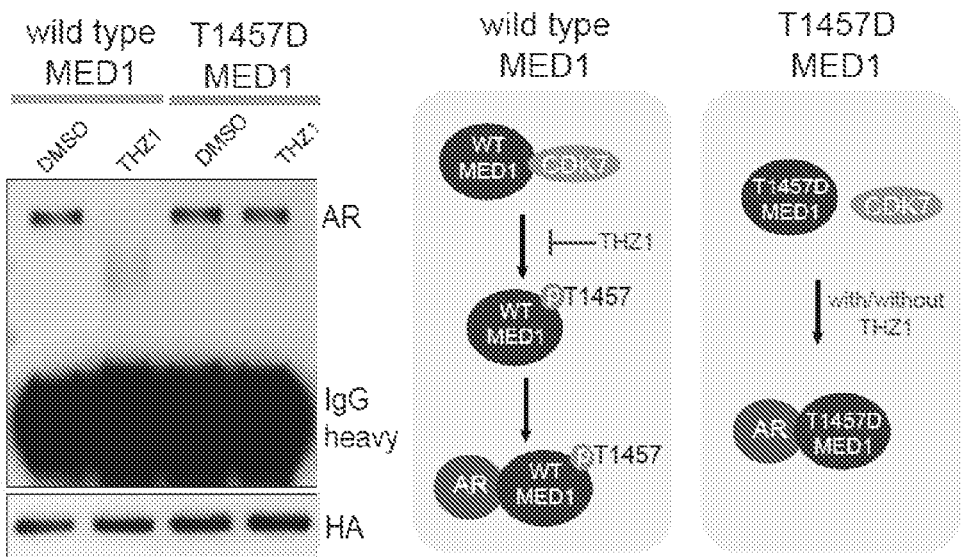
Figure 19E:
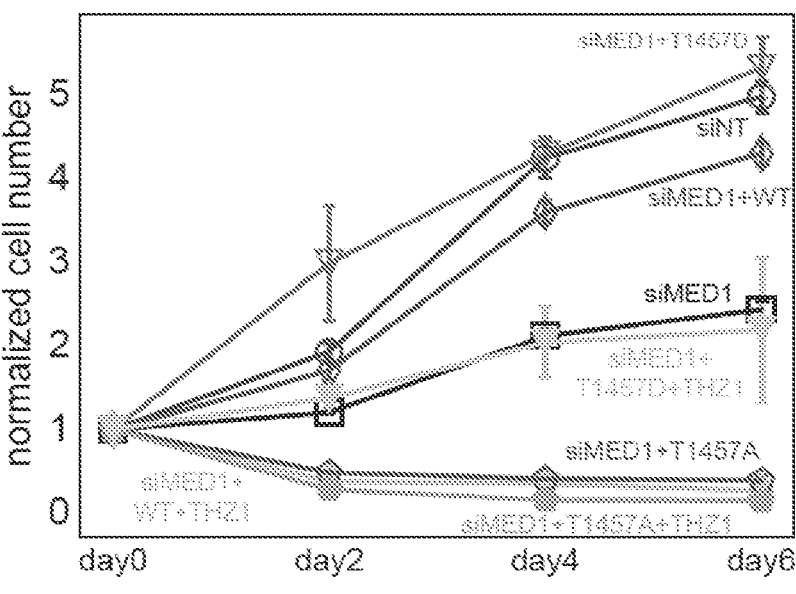
Figure 25A:
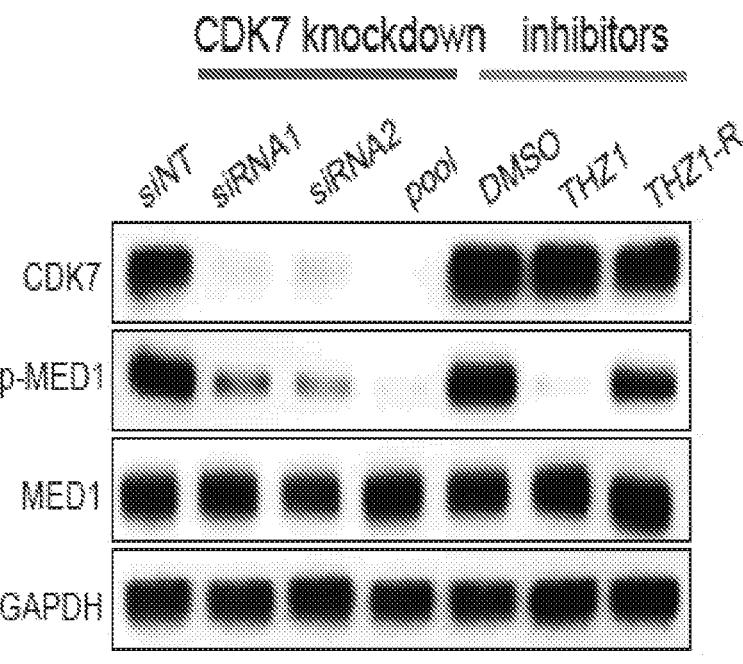
Figure 25B:
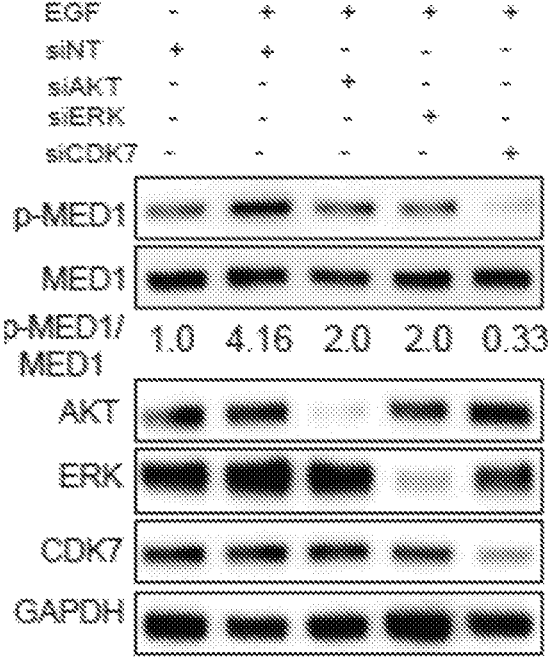
Figure 25C:
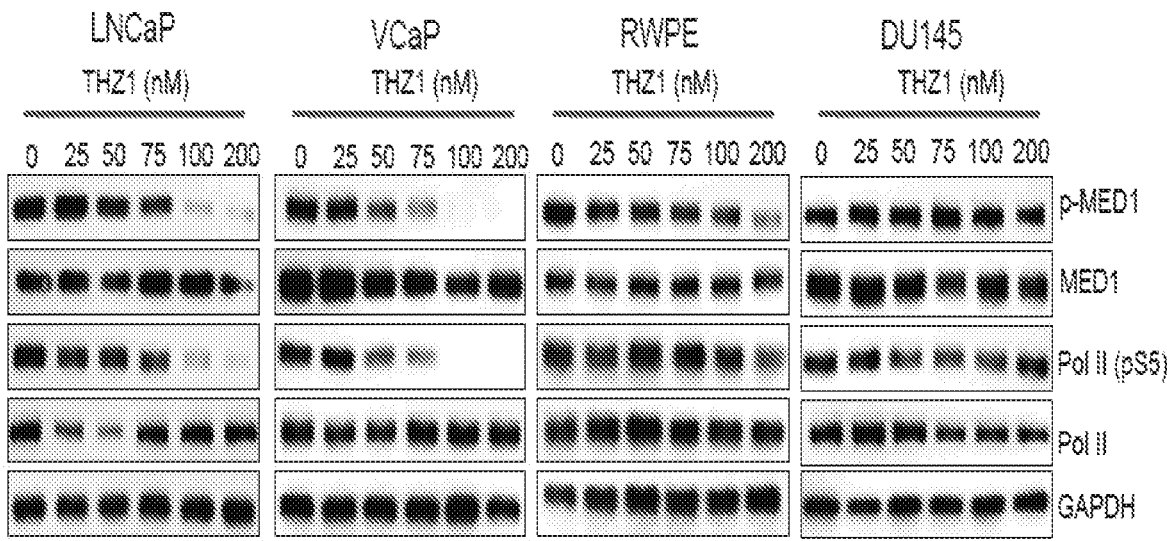
Figure 25D:
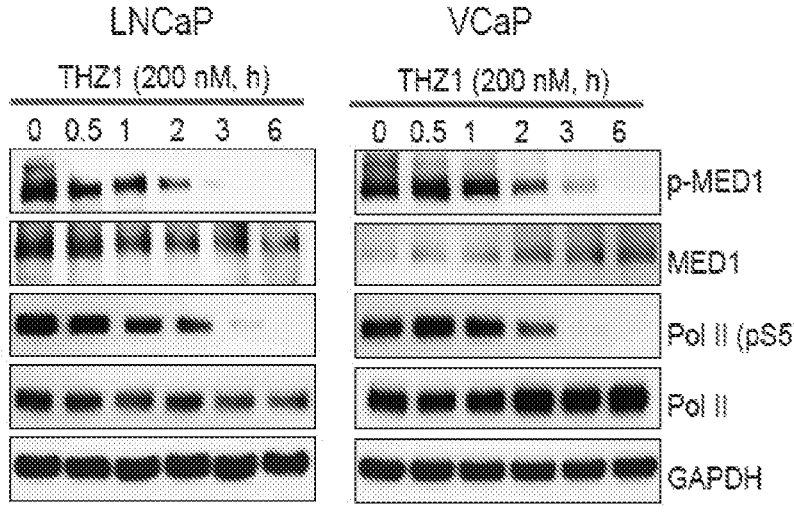
Figure 26C:
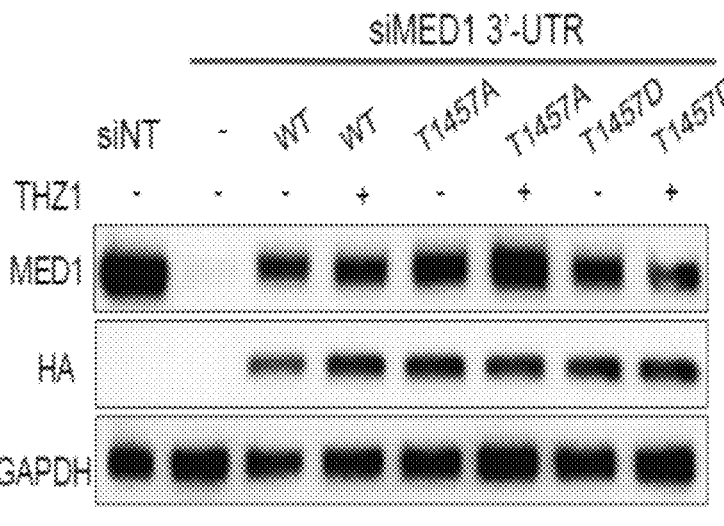
Figure 26D:
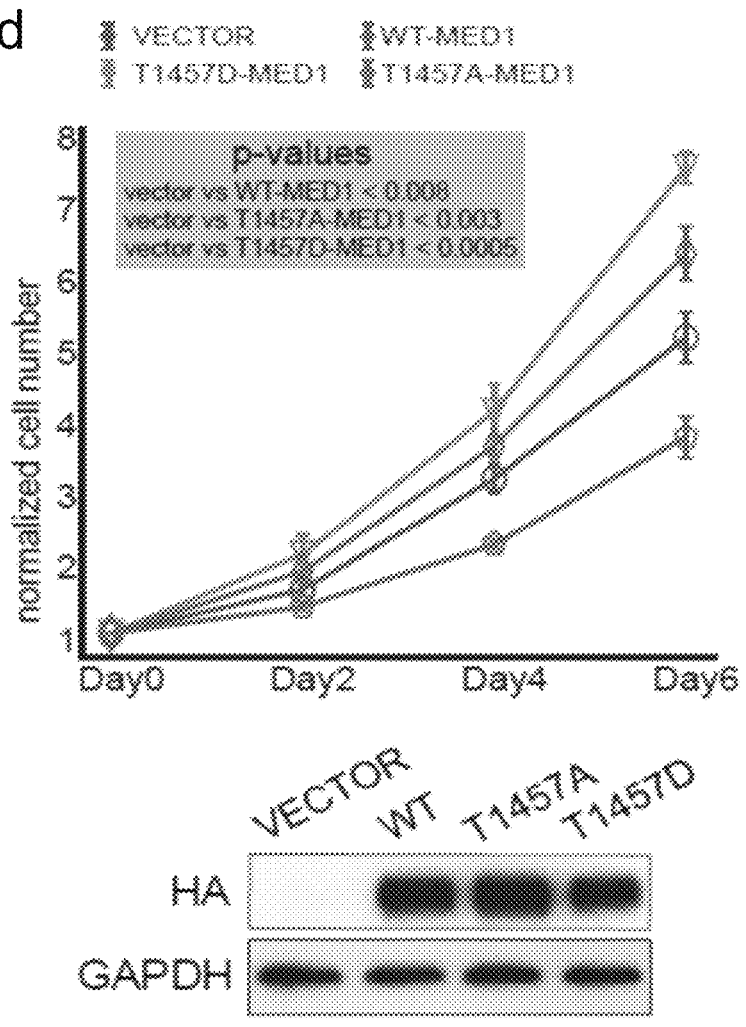

Next, to identify the kinase involved in the phosphorylation of MED1 in AR-driven PCa, we tested a series of transcriptional cyclin-dependent kinases (CDK), including CDK7, CDK8, CDK9, CDK12 and CDK13. We reasoned that transcriptional CDKs might be involved in MED1 phosphorylation as they have been previously shown to regulate processes associated with MED1 functions such as facilitation of gene-specific chromatin looping, coordination of chromatin modification events with pre-initiation complex assembly, and the regulation of transcriptional elongation by RNA PolII. We treated VCaP, LNCaP and mCRPC 22RV1 cell lines, which are characterized by three primary modes of AR dysregulation widely found in CRPC clinically, namely genomic copy-number amplification, gain-of-function mutation (T877A) and constitutively active splice variant, respectively, with a panel of CDK inhibitors. The pan-CDK inhibitor Dinaciclib completely abolished p-MED1 levels in all three tested cell lines grown in standard culture conditions (FIG. 5a). Contrary to previous reports that suggest ERK involvement in MED1 phosphorylation, we found that MEK inhibition with trametinib did not result in loss of p-MED1. Treatment with THZ1, a novel highly specific covalent inhibitor of CDK7/12 and 13 reduced p-MED1 levels at baseline and when stimulated with DHT, while the CDK9 specific inhibitor LDC had no such effect on p-MED1 levels (FIG. 5a and FIG. 6a). THZ1 is a phenylaminopyrimidine bearing cysteine-reactive acrylamide moiety and unlike most CDK inhibitors identified before, the THZ1 targeting site on CDK7/12/13 lies outside the kinase domain, providing possible explanations for the increased specificity of inhibition. To identify the specific CDK responsible for the phosphorylation of MED1, using a mixture of four siRNAs, we performed knock down of CDK7, CDK12, and CDK13 individually, along with CDK9 as a negative control. Interestingly, only CDK7 knockdown led to the loss of DHT induced p-MED1 with a parallel reduction in prostate specific antigen (PSA) levels, that served as a direct readout of AR transcriptional activity (FIG. 5b and FIG. 6b). The reduction in p-MED1 was further confirmed using individual siRNA against CDK7 as well as THZ1-R—a non-cysteine reactive analogue of THZ1 as a negative control (FIG. 25A). However, CDK7 rescue was able to restore the p-MED1 to the pre-knockdown levels (FIG. 19A). Additionally, mitogen induced p-MED1 was much strongly inhibited upon CDK7 knockdown, whereas knockdown of the previously reported MED1 kinase ERK or AKT displayed only a marginal reduction in the p-MED1 levels suggesting that these kinases could potentially be upstream effectors of CDK7 activity (FIG. 25B). CDK7 is a serine/threonine kinase that shows a preference for a proline in the +1 position relative to the phosphoacceptor residue. The RNA PolII CTD heptad sequence repeat, 1-YSPTSPS-7 (SEQ ID NO:41), in which CDK7 preferentially phosphorylates Ser5, obeys this rule. Additionally, CDK7 has been reported to phosphorylate sites containing Ser-Pro or Thr-Pro dipeptides within many DNA-binding transcription factors, including SPTS, E2F-1, Oct-1, and the tumor suppressor p53. Interestingly, the evolutionarily conserved T1457 phosphoacceptor residue of MED1 located in its intrinsically disordered region (IDR), appears remarkably similar to the SPTS site (FIGS. 6c and 6d). We next sought to determine whether CDK7 can directly phosphorylate T1457 on MED1 by performing in vitro kinase assays. Using purified recombinant components of CDK-activating-complex (CAK) comprising CDK7, Cyclin H and MAT1, and recombinant GST-tagged MED1 protein (amino acid 1391-1490) we observed Threonine phosphorylation, specifically at T1457, which was completely inhibited by THZ1 (FIG. 19B). This was further confirmed by assessing the ability of CDK7 to phosphorylate a wildtype or T1457A mutant peptide. While CDK7-mediated phosphorylation of the T1457 wildtype peptide was inhibited by THZ1 treatment in a dose-dependent manner, CDK7 exhibited no activity towards the T1457A mutant peptide (FIG. 19C). The role of CDK7 in regulating MED1 phosphorylation was further confirmed by Phos-tag analysis where we observed the loss of slow migrating p-MED1 bands upon CDK7 inhibition by THZ1 or siRNA mediated knockdown (FIGS. 6e and 6f). Furthermore, VCaP and LNCaP cells showed a dose- and time-dependent decrease in p-MED1 levels upon THZ1 treatment (FIGS. 6g and 6h). The VCaP and LNCaP cells showed a dose- and time-dependent decrease in MED1 p-T1457 levels that parallel reduced phosphorylation at Ser5 of RNA Poll upon THZ1 treatment (FIGS. 25C-25D). Intriguingly, AR negative RWPE and DU145 cells demonstrated no such decrease in p-MED1 or pS5-PolII levels even at the highest tested concentration of THZ1 (FIGS. 25C-25D). Reciprocal immunoprecipitation experiments confirmed an endogenous association between MED1 and CDK-activating kinase (CAK) complex comprising CDK7, cyclin H, and MAT1 along with RNA Poll and AR (FIGS. 5c and 5d). Subsequently, we observed the loss of endogenous MED1-AR complex formation upon THZ1 treatment in VCaP and LNCaP cells (FIG. 5e). We next sought to address the functional significance of phosphorylation of T1457 towards chromatin binding and AR interaction. Compared to the THZ1 sensitive wildtype MED1, the chromatin fraction was devoid of the T1457A mutant, whereas the T1457D phosphomimic was not only found in the chromatin fraction but its association to chromatin was insensitive to THZ1 (FIG. 26A). Notably, unlike wildtype MED1, the T1457D phosphomimic retained the interaction with AR in the presence of THZ1 (FIG. 19D). Furthermore, exogenous expression of phosphorylation mutants of MED1 after knockdown of endogenous MED1, demonstrated a reversal of the ligand-activated gene expression and cell proliferation by the T1457D phosphomimic, but not the T1457A mutant, even in the presence of THZ1 (FIG. 19E and FIGS. 26B-26C). Lastly, compared to wildtype MED1, overexpression of T1457A displayed a dominant negative phenotype, whereas T1457D expression led to a further increase in the proliferation of LNCaP cells (FIG. 26D). Together, these data identify MED1 T1457 as a novel substrate of CDK7 kinase and demonstrates its significance in AR signaling and PCa cell growth.

Figure 5F:
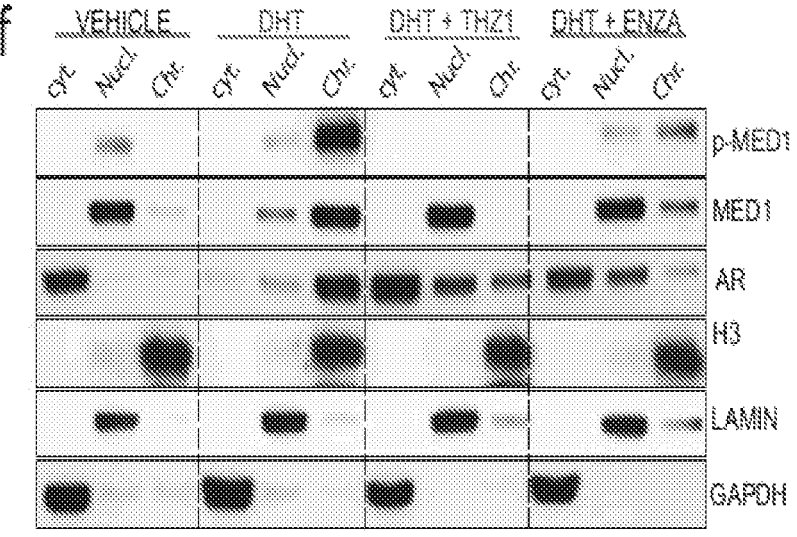
Figure 5G:
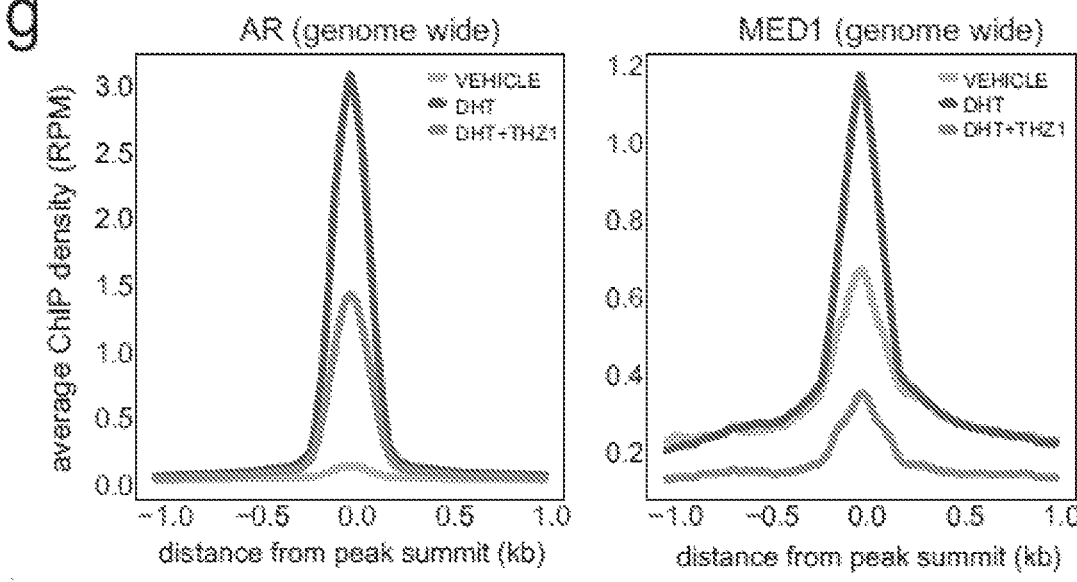

CDK7 Inhibition by THZ1 Leads to the Reversal of Ligand Induced MED1 Chromatin Recruitment Next, to test whether inhibition of CDK7 would result in the loss of MED1 chromatin accessibility, we isolated cytoplasmic, nuclear and chromatin protein fractions from DHT-stimulated (6 h) LNCaP cells, in the presence or absence of THZ1 (FIG. 5f). As expected, DHT-stimulation led to increased phosphorylation and recruitment of MED1 and AR to the chromatin from nuclear and cytoplasmic compartments, respectively, whereas THZ1 triggered a complete loss in the chromatin-bound levels of p-MED1/MED1 and confined the entire cellular fraction of MED1 to the nucleus (FIG. 20A). In contrast, the anti-androgen enzalutamide was unable to completely dissociate p-MED1 from the chromatin (FIG. 20A). These observations were further confirmed using ChIP-seq analysis of genome-wide MED1 and AR binding in LNCaP cells. As expected, the average ChIP-seq signal for MED1 and AR was highly enriched in DHT-treated cells (FIGS. 5g and 20B), and THZ1 blocked MED1 recruitment entirely (i.e., reversed the MED1 enrichment) and in turn significantly limited AR recruitment (i.e., led to significant AR de-recruitment) genome-wide as a consequent disruption of MED1-AR complex in both VCaP and LNCaP cells. Focusing our evaluation specifically on the MED1 and AR coincident peaks, we observed a complete abrogation of MED1 recruitment by THZ1 to the AR bound enhancers and super-enhancers (FIG. 5h and FIG. 7a). Examples of gene tracks of AR-specific genes co-occupied by MED1 and AR on upstream enhancers and super-enhancers (SE) validate the genome-wide findings (FIGS. 5i and 25C). RNA-seq analysis further confirmed that THZ1 mediated blockade of MED1 and AR recruitment to super-enhancers lead to massive down-regulation in the transcription of AR-target genes, as is readily seen in the RNA-seq genome browser tracks on the KLK locus (FIG. 5i). Our analysis also showed that THZ1 completely reversed almost all of the genome-wide DHT-induced differentially expressed AR target genes. (FIG. 5i and FIG. 7b-e).

Figure 20D:
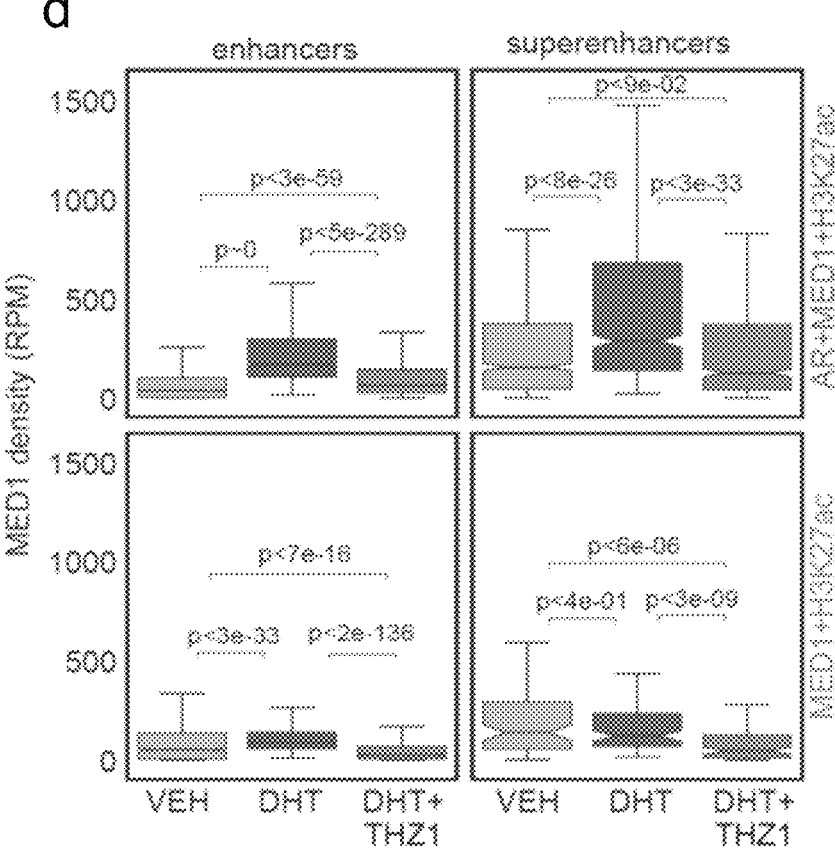
Figure 27A:
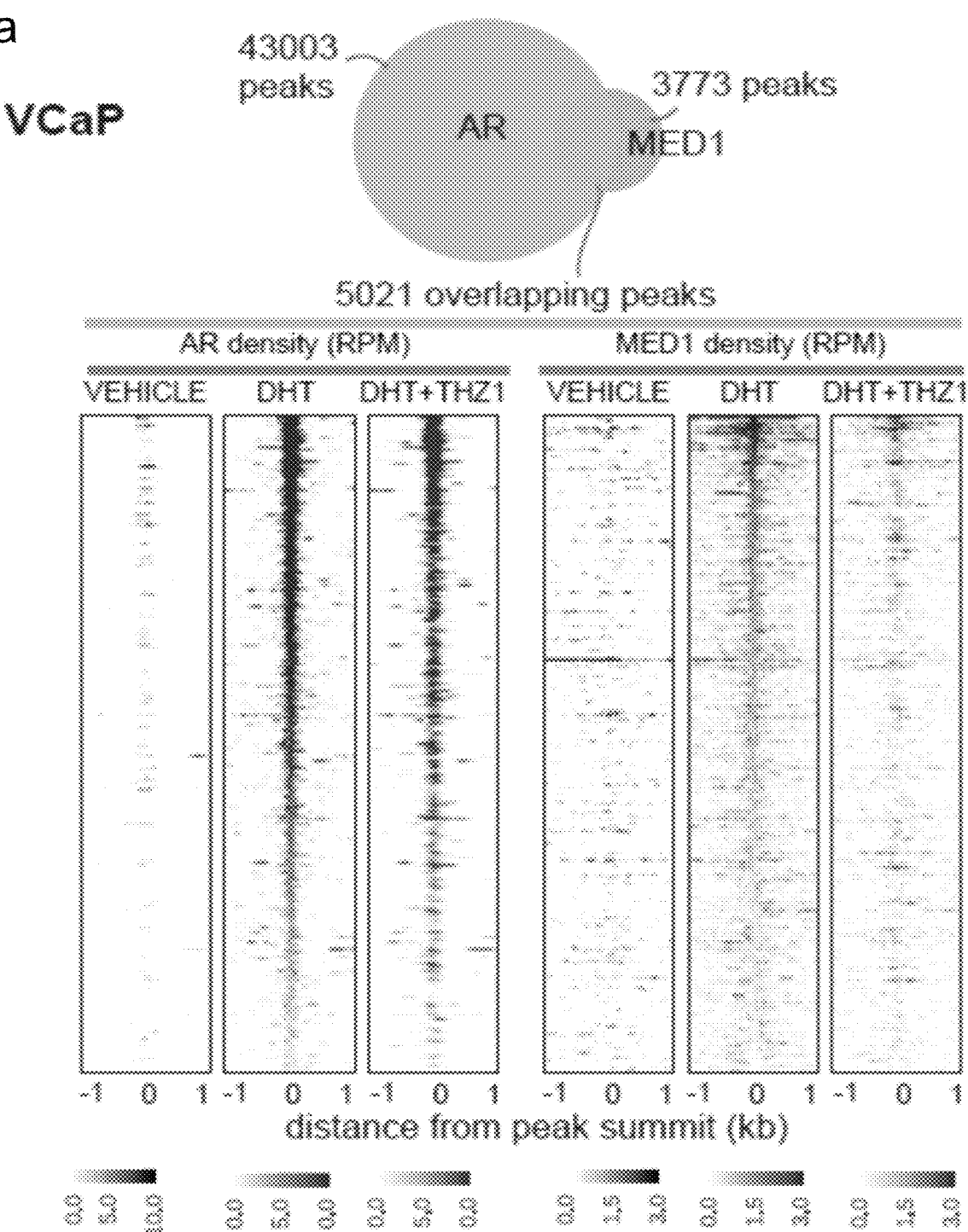
Figure 27B:
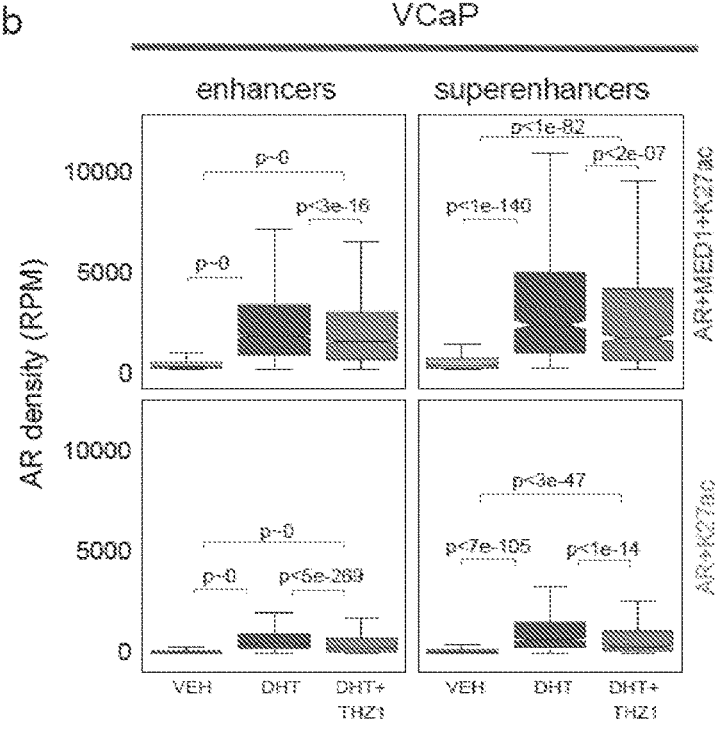
Figure 27C:
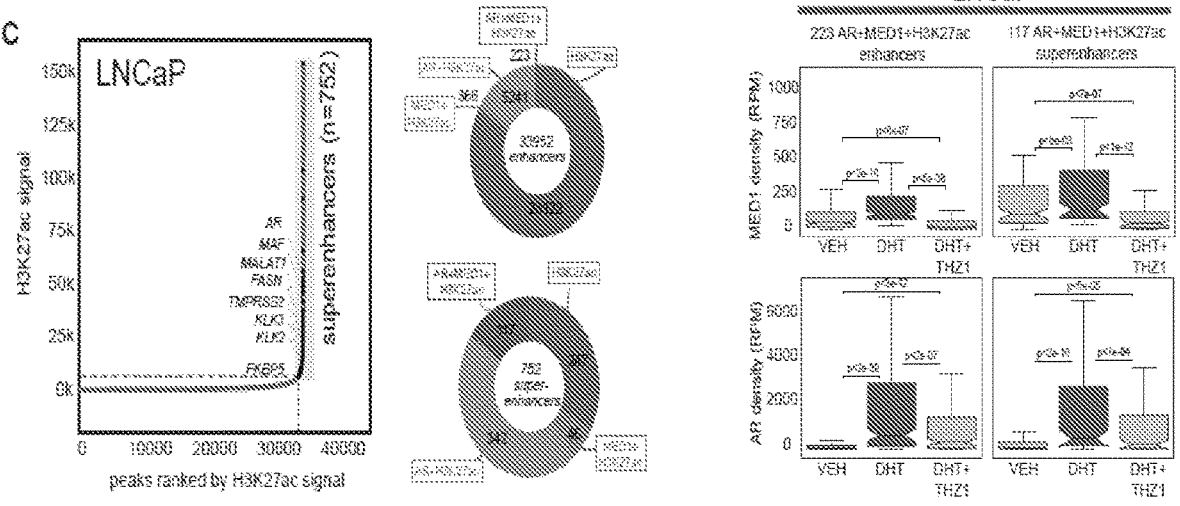
Figure 27D:
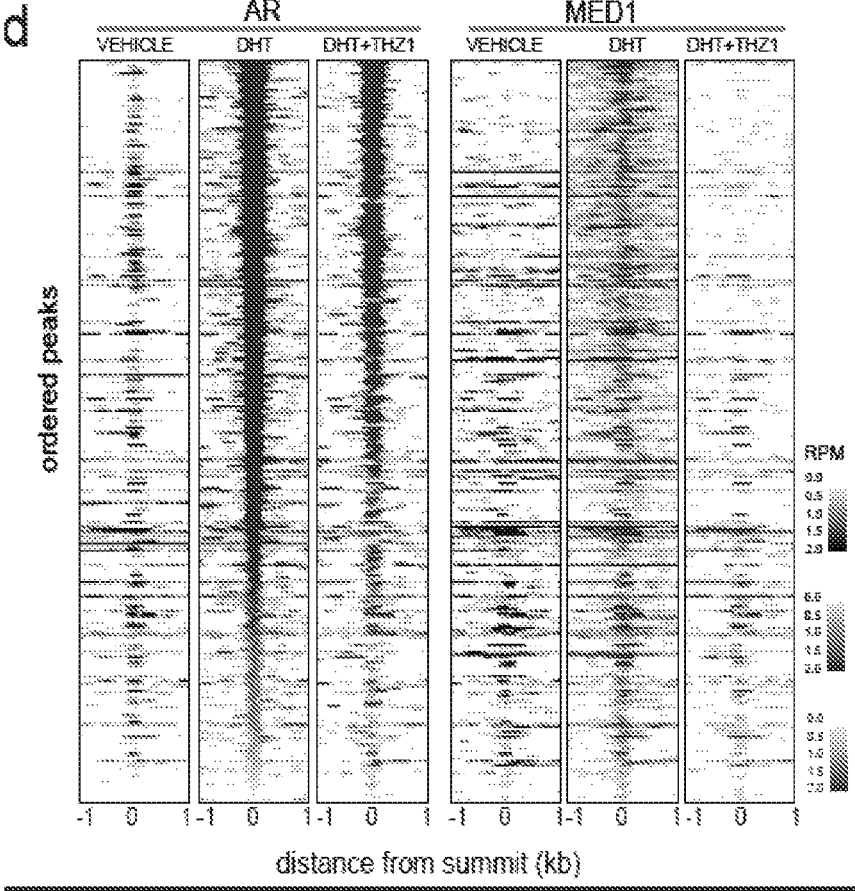
Figure 27E:
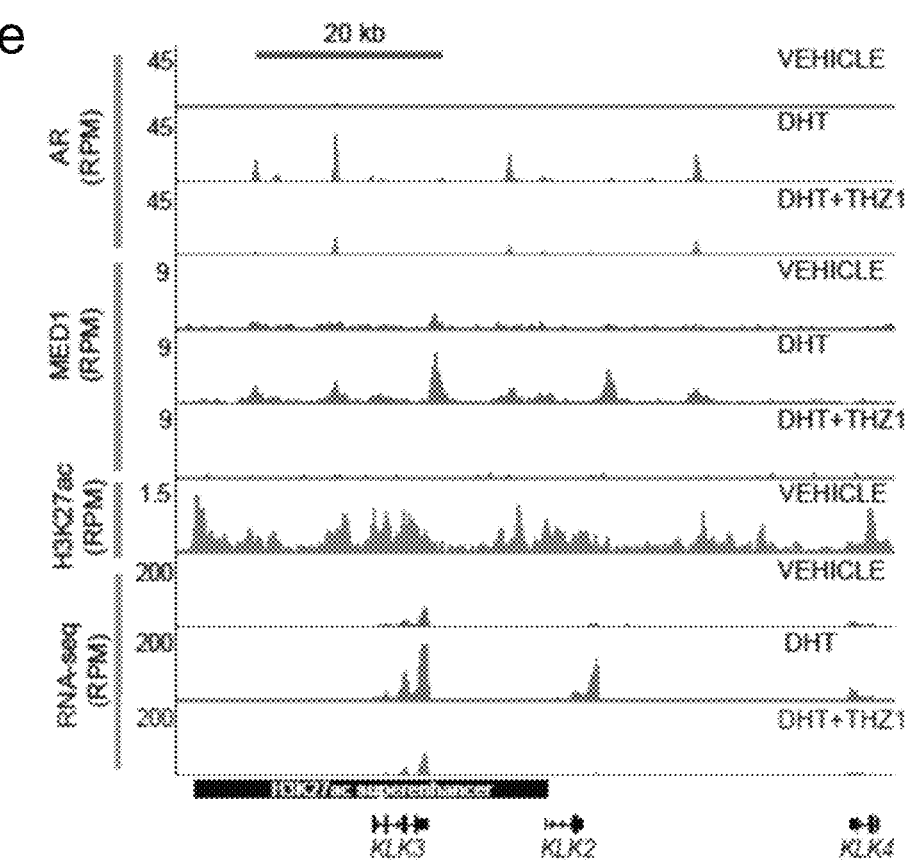

Next, focusing our evaluation specifically on the MED1 and AR bound regions (see FIG. 27A), DHT stimulated VCaP cells displayed increased MED1 levels in the AR occupied enhancers and SEs, defined by H3K27ac, whereas enhancers and SEs devoid of AR but positive for MED1 did not show any such increase, further establishing ligand-dependent recruitment of MED1 to the AR bound regulatory regions (FIG. 20D). Notably, AR was enriched at a much higher level at both the enhancers and SEs co-occupied by MED1 (FIG. 27A), suggesting the binding of MED1 following AR recruitment to the chromatin stabilizes the AR complex. As expected, THZ1 treated cells demonstrated more efficient loss of MED1 enrichment from the AR bound enhancers and SEs when compared to the AR-deficient MED1 containing enhancers and SEs (FIG. 20D). Similar observations were made in the LNCaP cells (FIGS. 27C-27E). Next, integration of the ChIP-seq data with RNA-seq transcriptome demonstrated that greater than 90% of DHT-induced genes common in VCaP and LNCaP cells were associated with AR and MED1 co-occupied enhancers and SEs (FIG. 20E). Interestingly, upon THZ1 treatment the SE associated genes displayed a significant reduction in expression (p<7e-18) compared to enhancer-associated genes (p<6e-14) (FIG. 20E). Additionally, GSEA analysis demonstrated a complete reversal in the expression of DHT-induced differentially expressed AR target genes upon THZ1 treatment in VCaP and LNCaP cells (FIGS. 27F-27H). Additionally, to compare the potency of THZ1 and enzalutamide in blocking DHT-induced AR target gene expression, LNCaP and VCaP cells were cells were treated with THZ1 or enzalutamide followed by DHT treatment and analyzed for canonical AR target gene expression. THZ1, even at 100 nM, phenocopied the reduction in DHT-induced gene expression observed in the 10 μM enzalutamide treatment condition (FIG. 7f).

Next, we performed knockdown of CDK7 to orthogonally validate the specificity of THZ1 in modulating AR transcriptional program and found a complete reversal of DHT-induced transcriptional changes, including loss of hallmark androgen response signature gene expression, without affecting AR protein expression (FIG. 8a-d). Interestingly, the gene sets that were significantly affected by CDK7 knockdown were analogous to those obtained by MED1 knockdown (FIG. 3e). These data establish the CDK7 inhibitor THZ1 as a potent agent for antagonizing AR-signaling through its ability to inhibit phosphorylation-dependent recruitment of MED1 to the AR cistrome in PCa cells.

Figure 9H:
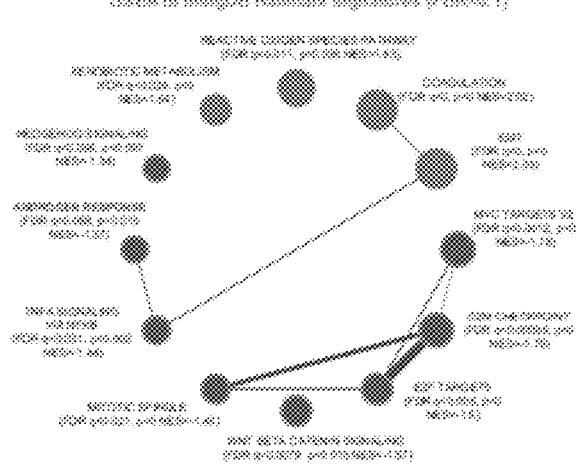
Figure 10A:
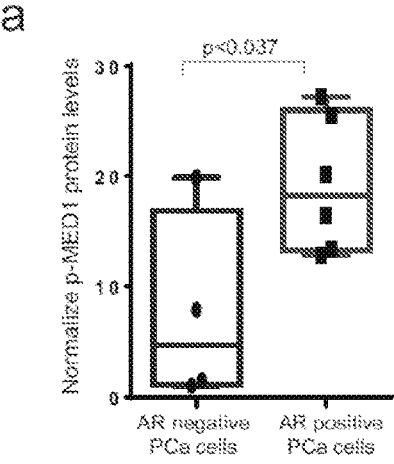
Figure 10B:
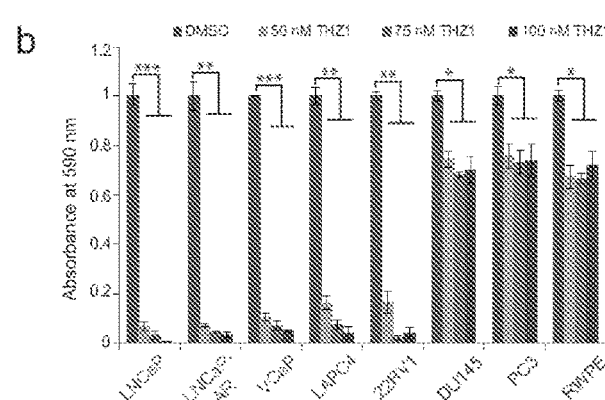
Figure 10C:
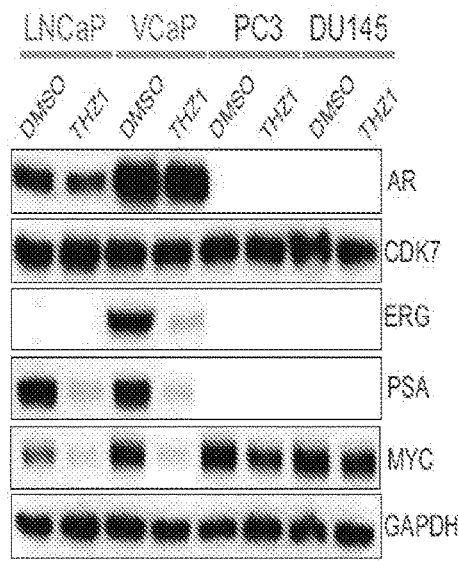
Figure 10D:
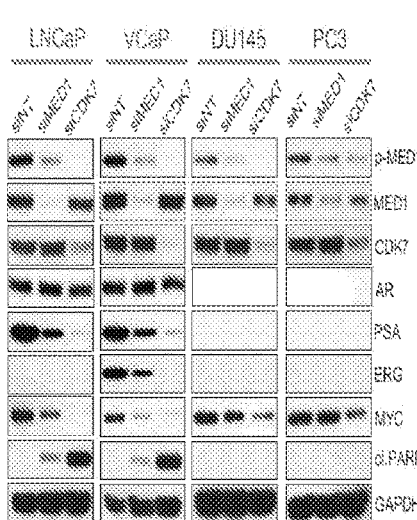
Figure 10E:
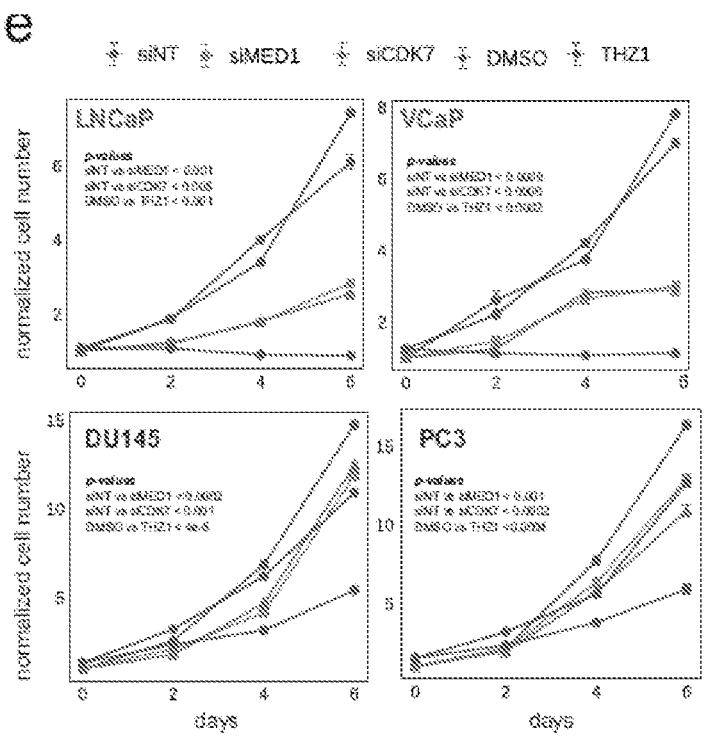
Figure 10F:
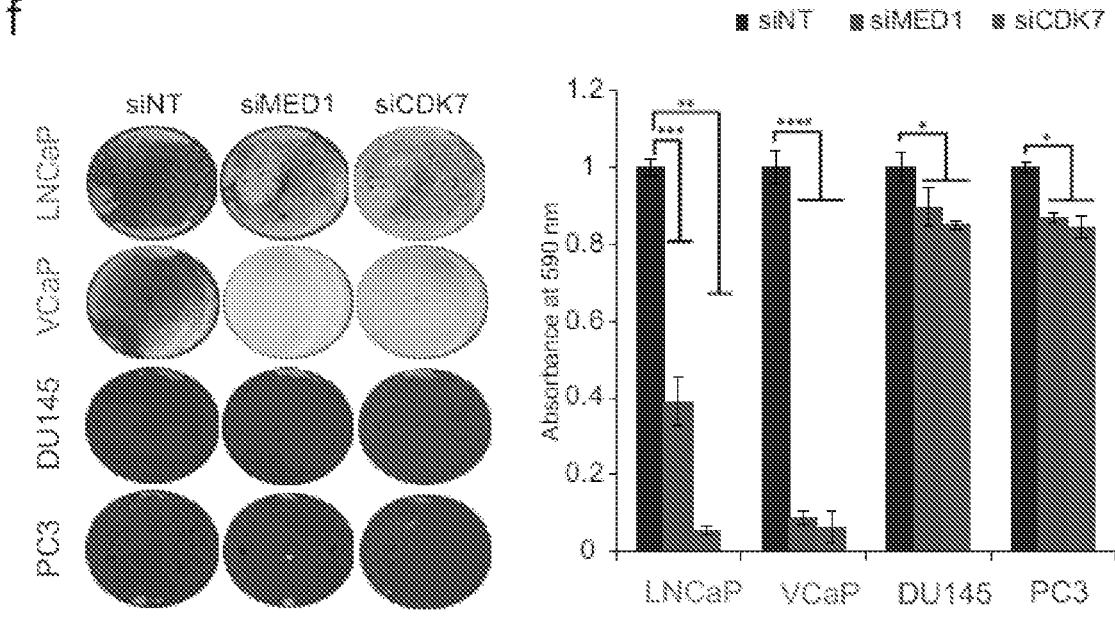
Figure 11D:
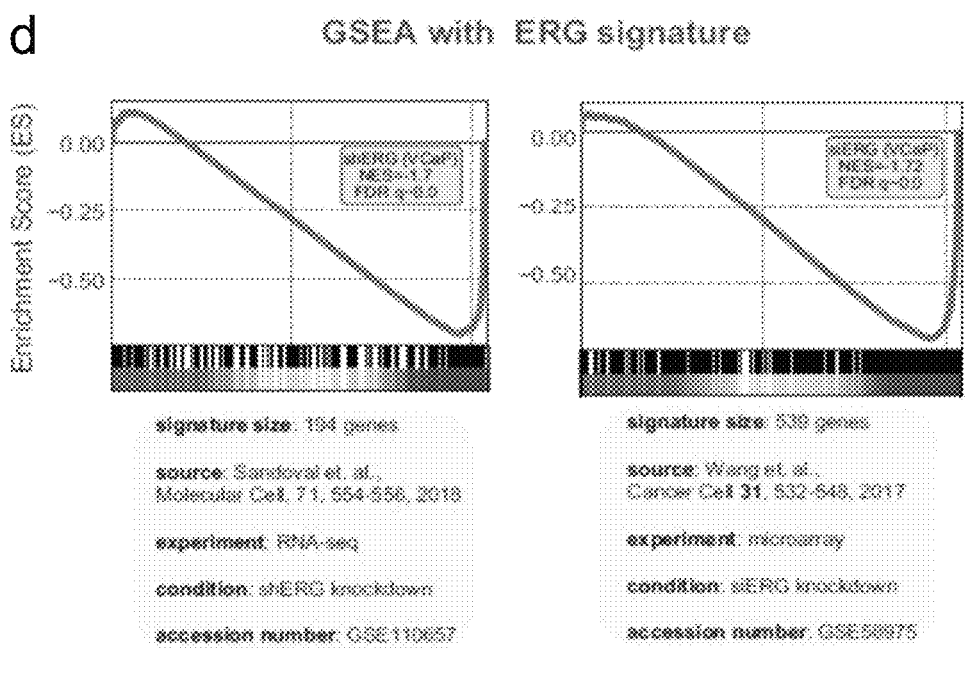
Figure 11E:
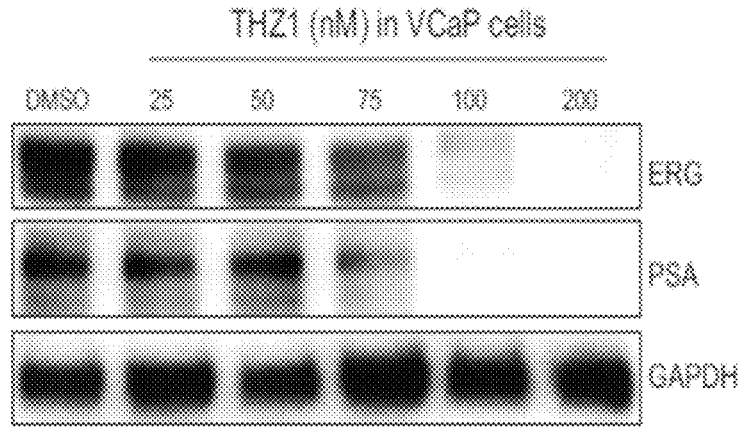
Figure 11F:
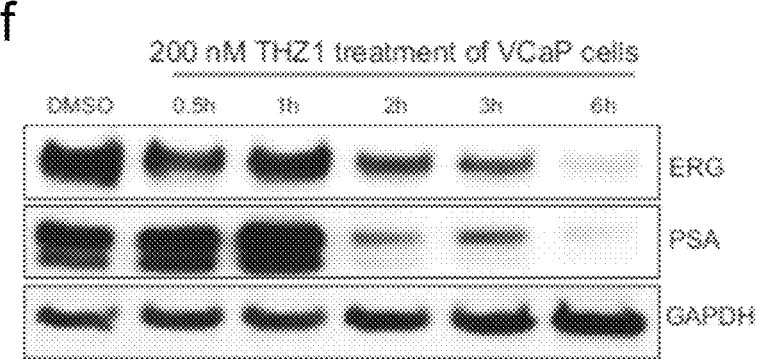

Prostate Cancer Cells with Hyperactive AR-Signaling are Sensitive to CDK7 Inhibition Based on the observations that genetic and pharmacologic inhibition of CDK7 affected AR-signaling through the disruption of MED1-AR chromatin interaction (FIGS. 5A-5I), we hypothesized that AR-dependent PCa cells would be more sensitive to THZ1 treatment. To test this hypothesis, we treated a panel of seven PCa lines and one benign prostate cell line with THZ1. Using a cell viability assay, we found that the five AR-dependent PCa lines tested were highly sensitive to THZ1 with a GI50 concentration ranging between 50-170 nM, whereas the remaining three AR-negative cells displayed a GI50 ranging from 400-600 nM (FIG. 9a). Interestingly, though all the cell lines expressed equal amounts of CDK7, AR-positive cells displayed higher p-MED1 levels (FIG. 9b and FIG. 10a). Additionally, even at a relatively low 50 nM concentration, THZ1 severely inhibited long-term colony formation of AR-positive cells (FIG. 9c and FIG. 10b). Importantly, THZ1 treatment induced robust apoptosis in the AR-positive LNCaP and VCaP cells, a response not observed in the AR-negative PC3 and DU1A-5145 cells (FIGS. 9d and 9e), suggesting that AR status defines the THZ1 sensitivity in PCa cells, i.e., is a major determinant of THZ1 sensitivity. Subsequently, treatment with THZ1 or siRNA knockdown of MED1 or CDK7 in LNCaP and VCaP cells decreased AR target protein expression, resulting in the induction of apoptosis, and preferential growth inhibition as compared to PC3 and DU145 cells (FIG. 10c-f). To determine the effect of THZ1 on global transcription, we treated LNCaP, VCaP, and DU145 cells with 100 nM THZ1, a concentration at which substantial inhibition of MED1 phosphorylation was achieved (FIGS. 6A-6F), and performed gene expression profiling by RNA-seq. Reflecting the observed phenotypic response, treatment with THZ1 led to a massive change in the gene expression in both the AR-positive VCaP and LNCaP cells, (1325 up/1203 down in VCaP and 2612 up/1695 down in LNCaP), whereas DU145 cells displayed minimal change in gene expression (191 up/190 down) (FIG. 9f and FIG. 11a). Gene Ontology terms for biological processes (GO:BP) for the 710 genes commonly down-regulated between VCaP and LNCaP strongly reiterates the dominant role of THZ1 in regulating key cellular processes, as shown by the enrichment for RNA Poll dependent transcription, cell cycle, DNA repair and chromatin organization (FIG. 9g). Moreover, GSEA in VCaP and LNCaP showed negative enrichment of the various hallmark signatures, including androgen response, MYC and E2F targets— known to be deregulated in AR-driven CRPC (FIG. 9h and FIG. 11b). Interestingly DU145 cells instead had positive enrichment for MYC and E2F target signatures (FIG. 11c), which could explain the reduced sensitivity to THZ1 observed in AR-negative PCa cells. Furthermore, VCaP cells, which harbor the AR-responsive TMPRSS2-ERG gene fusion found in greater than 55% of PCa, displayed a negative enrichment of ERG signature and a reduction in ERG levels upon THZ1 treatment in a dose and time-dependent manner (FIG. 11d-f). This efficient downregulation of ERG—an ETS family transcription factor is compelling as it is known to drive a unique transitional program, induce DNA damage, invasion and metastasis, and is difficult to target by small molecule inhibitors. Next, following a study that suggests direct phosphorylation of AR at S515 and transactivation by CDK7 kinase, we sought to address whether the observed downregulation of AR-signature by THZ1 is due to a reduction in the AR p-S515 levels. Unlike p-MED1, THZ1 treatment even at 200 nM for 12 h did not reduce AR p-S515 levels (FIGS. 28A-28B), suggesting the effects of THZ1 observed in AR signaling is primarily driven by its effect on p-MED1 and not on the presumed CDK7-mediated phosphorylation of AR at 5515. However, the influence of THZ1 on AR phosphorylation at S515 via long-term treatment with THZ1 could not be ruled out. Together, these results clearly suggest that THZ1 treatment of AR-positive cells directly interferes with AR and associated transcription factor activity via MED1 inactivation and inhibits key oncogenic pathways required for PCa survival.

Enzalutamide Resistant PCa Cells Display Higher Levels of p-MED1 and are Sensitive to THZ1

Figure 9I:
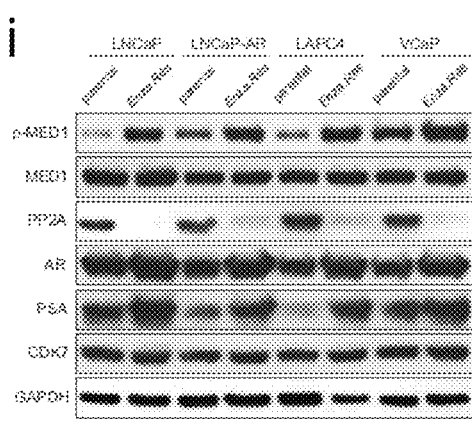
Figure 12A:
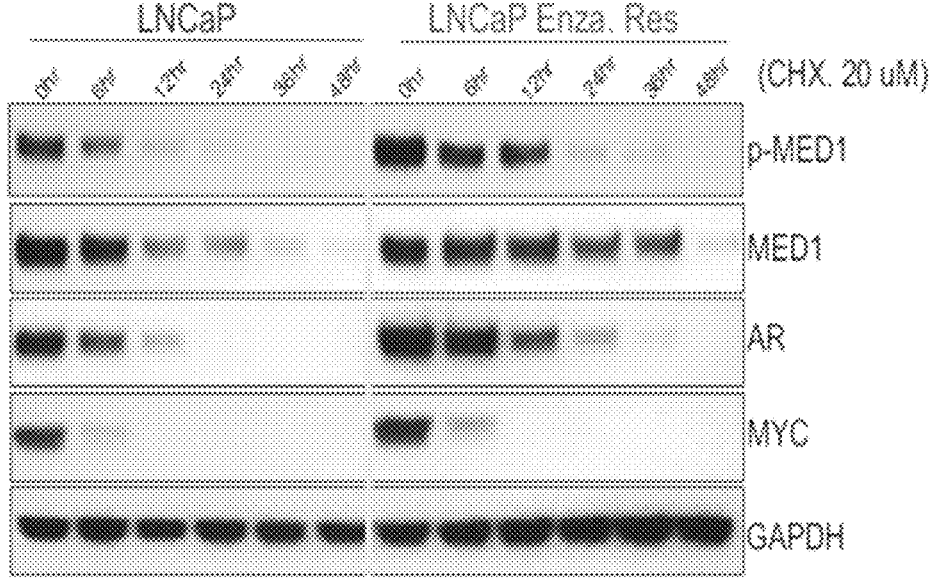
Figure 12B:
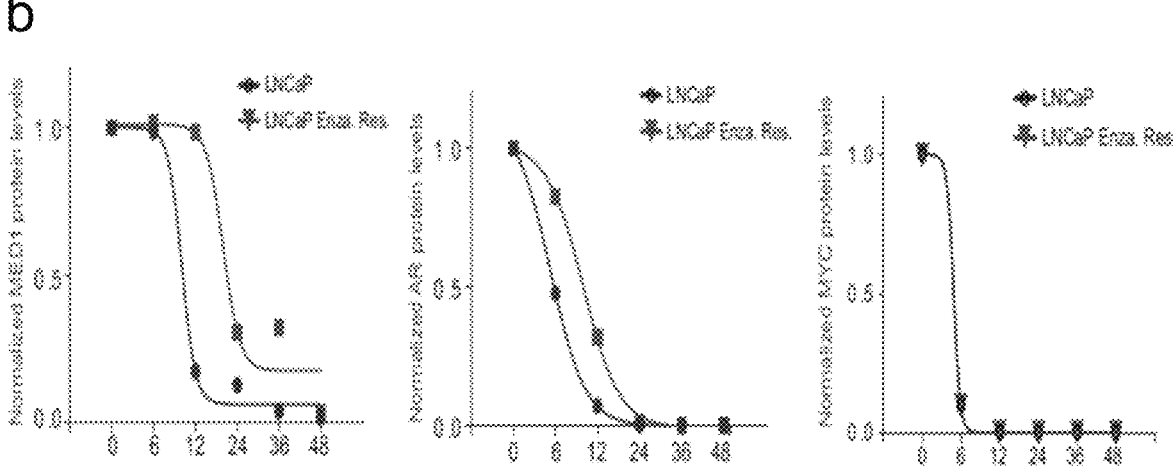

One of the current first-line therapies for metastatic CRPC is enzalutamide, a second generation anti-androgen, to which resistance invariably develops. The major mechanism of acquired resistance to enzalutamide is restoration of AR-signaling, which presents challenges for long-term disease control. To investigate whether amplification of AR-signaling is mediated through CDK7-dependent MED1 phosphorylation in enzalutamide refractory PCa, we first established resistant derivatives of LNCaP, LNCaP-AR, LAPC4 and VCaP cells by long-term exposure to enzalutamide. As expected, the enzalutamide-resistant cells displayed increased PSA expression suggestive of restored AR-signaling, surprisingly accompanied by increased p-MED1 levels (FIG. 9i). Additionally, compared to parental control, increased stability of MED1 was observed in enzalutamide-resistant cells resulting from its hyper-phosphorylated state (FIGS. 12a and 12b). The increased AR stability observed in enzalutamide-resistant cells could be due to increased phosphorylation at S515 and S81, and an indirect consequence of its more stable binding to the p-MED1. Next, we sought to confirm the role of p-T1457 in MED1 stability by conducting additional cycloheximide chase experiments. As expected, compared to the wildtype T1457 MED1, the phospho-dead T1457A mutant protein demonstrated decreased stability and lower half-life (FIG. 22C). Pathologic phosphorylation results from both aberrant activation of kinases and inactivation of phosphatases and is a hallmark of many diseases including cancer. Protein phosphatase 2A (PP2A) is a heterotrimeric serine/threonine phosphatase that prevents pathogenic signaling by dephosphorylating substrates that are key signaling effectors. PP2A is a multi-protein complex that is minimally composed of a scaffolding A subunit (PP2A-A) catalytic C subunit (PP2A-C), and a regulatory B subunit (PP2A-B). Substrate specificity is dictated by the binding of one of at least fifteen regulatory B subunits to form an active PP2A heterotrimer.

Figure 9J:
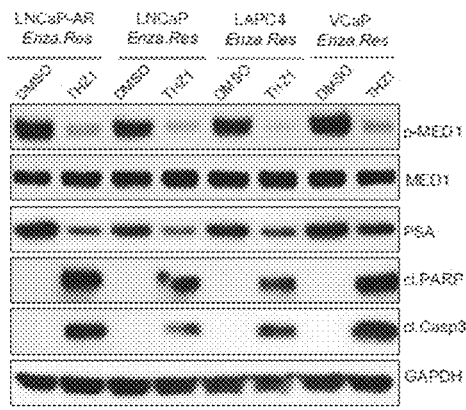
Figure 9K:
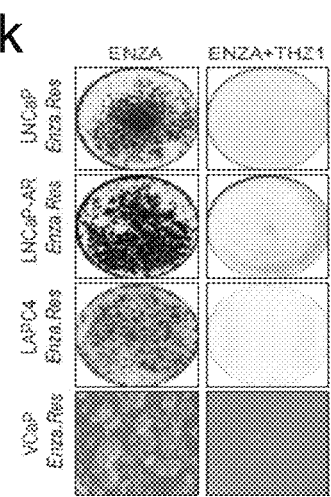
Figure 12C:
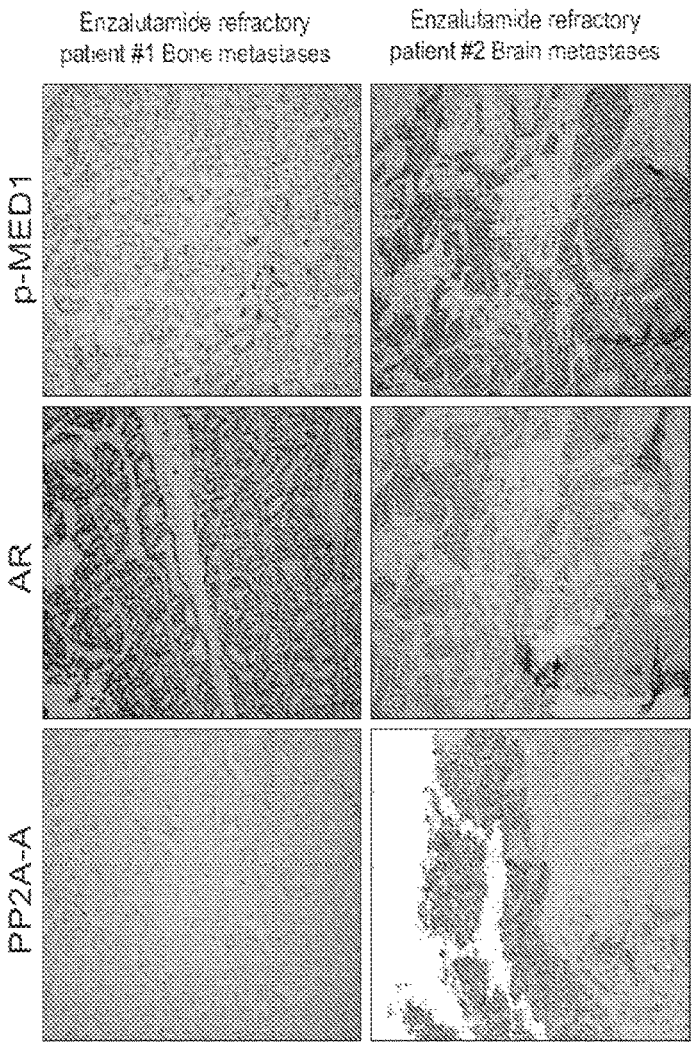
Figure 12D:
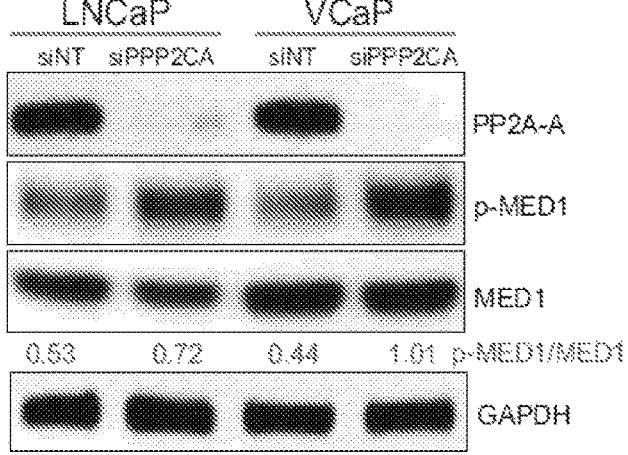
Figure 12E:
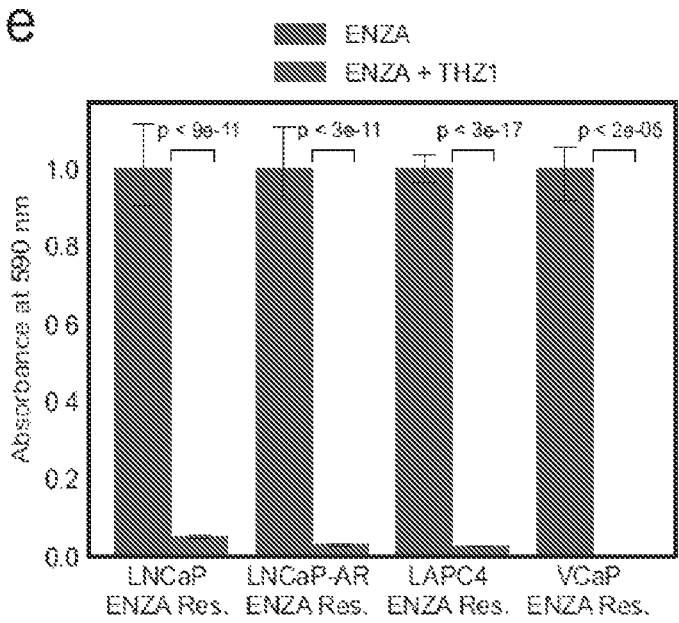

PP2A inactivation has been associated with therapy resistance in multiple malignancies including CRPC. Though no change in CDK7 was observed, enzalutamide-resistant cells displayed significantly reduced PP2A-A expression compared to their parental controls (FIG. 9I). Consistent with this cell line data, metastatic biopsies (brain and bone) from two enzalutamide refractory patients displayed increased p-MED1 with an associated loss in PP2A-A expression (FIG. 12c). Knockdown of PPP2CA, the catalytic subunit of PP2A-A, which has been shown to significantly abrogate PP2A enzymatic activity, led to enhanced p-MED1 levels (FIG. 12d), confirming PP2A mediated regulation of MED1 phosphorylation. In support of these findings, treatment with THZ1 led to the loss of p-MED1, reduced PSA, increased apoptosis, and growth inhibition in enzalutamide resistant cells (FIG. 9j, 9k and FIG. 12e). Together this data demonstrates that enzalutamide resistant cells with elevated levels of p-MED1 are highly susceptible to CDK7 inhibition due in part to restored AR-signaling and loss of PP2A.

CDK7 Inhibition by THZ1 Blocks CRPC Growth in Mice

Based on our in vitro data identifying THZ1 as a potent inhibitor of AR-mediated transcription through MED1 inactivation (FIGS. 5A-12E), we sought to study its efficacy in blocking castration-resistant prostate cancer growth in an in vivo mouse xenograft model. We utilized the VCaP model, as it harbors the TMPRSS2:ERG gene fusion and AR amplification, both of which are frequent molecular aberrations observed in CRPC patients. Although the VCaP cell line was originally derived from a patient with CRPC, these cells require constant androgen supplementation for in vitro growth. As a result of this phenomenon, the VCaP tumor xenograft responds to castration initially but eventually relapse in mouse models. VCaP tumor-bearing mice were established and then castrated, leading to tumor regression. Upon regrowth and once the tumors reached their original pre-castrated size (~150 mm$^3$), mice were randomized into two groups and treated intraperitoneally with vehicle (n=8) or THZ1 (10 mg/kg/b.i.d.) (n=8) for four weeks (FIG. 13a). Treatment with THZ1 led to a dramatic tumor regression compared to vehicle control (FIG. 13b and FIG. 14a). Additionally, THZ1 treatment was well tolerated with no treatment-related systemic toxicity observed in mice (FIG. 14b), suggesting that THZ1 treatment allows a broader therapeutic window in cancer versus normal cells. Tumors from vehicle-treated mice displayed higher PSA expression, a high proliferative activity and lower apoptosis (FIG. 13c and FIG. 14c). By contrast, the vast majority of the residual tumors from THZ1-treated animals demonstrated loss of PSA expression, necrosis, reduced proliferative activity and increased apoptosis. Importantly, there was a significant reduction in p-MED1 levels in THZ-1 treated tumors confirming target engagement in vivo. Additionally, plasma PSA expression in THZ1-treated mice was significantly reduced compared to vehicle treated mice (FIG. 13d), suggesting that THZ1 was able to potently inhibit AR-signaling in vivo. Interestingly, unlike the tumor regression phenotype observed for the VCaP xenografts, treatment with THZ1 at 10 mg/kg b.i.d for four weeks led to tumor growth inhibition of AR-negative DU145 xenografts in the castrated mice (n=8) (FIG. 30A), which was associated with reduced p-MED1 levels, lower Ki-67 and increased apoptosis when compared to vehicle treated controls (FIGS. 30A-30D). Together, these data clearly demonstrate the in vivo efficacy of THZ1 in prostate cancer xenograft models. Additionally, the more marked effect of CDK7 inhibition in the castration-resistant VCaP xenograft model compared to the AR-nega-tive DU145 model supports the in vitro results showing increased dependence in AR-driven tumors.

Discussion

Maintenance of AR-signaling is the most frequent resistance mechanism in CRPC patients that develops after conventional hormone deprivation and newer generation anti-androgen therapies. Genetic and epigenetic events lead to AR amplification, mutation, and alternative splicing resulting in the observed AR-driven transcriptional addiction seen in CRPC. Here, CDK7 directed MED1 phosphorylation at T1457 was demonstrated to be a key regulator of AR function, and inhibition of the CDK7-MED1 axis results in significant tumor growth inhibition in AR-positive prostate cancer cells in both cell culture and in vivo models. In addition to blocking AR-signaling and ligand-activated AR and MED1 recruitment to chromatin, THZ1 also negatively regulates the expression and oncogenic activity of TMPRSS2-ETS gene fusion products. This is very exciting as the oncogenic ETS transcription factors have been notoriously difficult to target therapeutically. Collectively, this data suggests a model in which CDK7 inhibition simultaneously blocks the functional activity and/or expression of multiple oncogenic transcriptional drivers in prostate cancer including AR, ETS, MYC, and E2F, all of which require MED1 as a cofactor. Moreover, our data elucidating ligand-activated phosphorylation of MED1 by CDK7 and its recruitment to the AR bound super-enhancers support the recent studies that revealed the phase—separation property of MED1 through its IDRs that result in the formation of high-density assembly of transcription apparatus at super-enhancers. The mechanistic basis for the phase-separation of MED1 is not well understood, which we hypothesize may be due to the phosphorylation of MED1 by CDK7 in response to growth stimuli or nuclear translocation of steroid hormone receptors, such as AR.

CDK7 is a ubiquitously expressed kinase (FIG. 31A) that contributes to control of the cell cycle through phosphorylation of other CDKs, and plays a crucial role in transcription as part of the transcription factor TFIIH complex. A Pan-Cancer analysis for CDK7 in TCGA revealed comparable level expression (FIG. 31B). However, little is known about CDK7 expression and activity in advanced prostate cancer. Analysis of data sets comprising benign, primary, and metastatic prostate cancer showed no significant change in the expression of CDK7 mRNA between the groups (FIG. 31C) which is in line with equal CDK7 protein levels observed in benign and PCa cells (FIGS. 9B and 21B). Nevertheless, potential increase in CDK7 activity through T-loop Thr170 phosphorylation by dysregulated MAPK and PI3K/AKT pathway in advanced prostate cancer cells could not be ruled out.

CDK7 inhibitors have demonstrated efficacy in T-cell acute lymphoblastic leukemia, small cell lung cancer, glioblastoma, and triple-negative breast cancer. The mechanism for the observed anti-tumor activity of CDK7 specific inhibitors is suggested to be the attenuation of transcriptional addiction required for the growth and survival of cancer cells. Though CDK7 is involved in normal transcription as an essential component of TFIIH, it is not clear why normal cells are less sensitive to CDK7 inhibition. One possible explanation is that cancer cells are addicted to transcription driven by super-enhancers and thus highly dependent on CDK7 activity as exemplified by the identification of a so-called "Achilles cluster" of genes in TNBC, as well as MYCN amplified glioblastoma. These observations have led to the clinical development of CDK7 specific inhibitors. Currently, SY1365, a covalent CDK7 selective inhibitor is being assessed in a phase 1 trial in adult patients with advanced solid cancer as a single agent or in combination with standard of care therapies (clinicaltrials.gov/ct2/show/ NCT03134638). Additionally, a second inhibitor, CT7001 (Carrick therapeutics, UK) is also in Phase I expansion for multiple malignancies.

While there has been much excitement around the development and successful clinical implementation of second-generation therapeutics targeting the androgen axis, such as abiraterone and enzalutamide, the responses to these agents are often not durable. Resistance mechanisms to these drugs include those that develop with conventional hormonal treatment (e.g., AR amplification/mutation/intratumor androgen synthesis) as well as novel mechanisms involving compensatory steroid hormone signaling (e.g., estrogen receptor (ER) or glucocorticoid receptor (GR)). As CDK7 inhibition functions "downstream" of AR itself through MED1 inactivation (FIG. 13e), our data suggest that CDK7 directed therapies may be effective in the context of a wide range AR-directed resistance mechanisms. Our identification of MED1 T1457 as a novel CDK7 substrate, which is essential for driving AR-mediated transcription makes CDK7 a potential "non-oncogene dependency" in advanced prostate cancer. Taken together, the data presented here strongly support the clinical evaluation of CDK7 specific inhibitors as a monotherapy or in combination with second generation anti-androgens for the treatment of refractory CRPC.

Data Deposits

RNA-seq, and ChIP-seq data have been deposited in the NCBI GEO database with the accession GSE125245 (www.ncbi nlm nih gov/geo/query/ acc.cgi?acc=GSE125245).

In the Examples, we thus investigated the molecular mechanism underlying the association between the transcriptional co-activator MED1 and AR as a vulnerability in AR-driven CRPC. MED1 undergoes CDK7 dependent phosphorylation and physically engages AR at super-enhancer sites and is an essential determinant for AR-mediated gene transcription. Additionally, a CDK7 specific inhibitor THZ1 blunts AR-dependent neoplastic growth by blocking AR/MED1 co-recruitment at a genome-wide level, as well as results in reversion of the hyper-phosphorylated MED1 associated enzalutamide resistant phenotype. In vivo, THZ1 induces tumor regression of AR amplified castration-resistant human prostate cancer in xenograft mouse models. Together, this work demonstrates that CDK7 inhibition selectively targets MED1-mediated, AR-dependent oncogenic transcriptional amplification, thus representing a new approach for the treatment of advanced prostate cancer.

Therefore, the identification and therapeutic targeting of chromatin-associated co-activators or mediators of AR function should be considered as alternative or complementary strategies to block AR transcriptional addiction that defines a large majority of CRPC.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for treating an androgen receptor (AR)-dependent cancer, comprising administering an effective amount of an inhibitor of cyclin dependent kinase 7 (CDK7) or a corresponding pharmaceutical composition to a human subject in need thereof, wherein the (AR)-dependent cancer is prostate cancer.

2. The method for treating an AR-dependent cancer according to claim 1, wherein the prostate cancer is castration resistant prostate cancer (CRPC).

3. The method for treating an AR-dependent cancer according to claim 1, wherein the CDK7 inhibitor is THZ1, SY-5609, CT7001, seliciclib, TG-02, PHA-793887, SY-351, roniciclib, SNS-032, BS-181L, and BS-194.

4. The method for treating an AR-dependent cancer according to claim 1, wherein the subject is resistant to anti-androgen therapy.

5. The method for treating an AR-dependent cancer according to claim 4, wherein the anti-androgen therapy comprises abiraterone enzalutamide, apalutamide, or darolutamide.

6. The method for treating an AR-dependent cancer according to claim 1, wherein the administering the cyclin dependent kinase 7 (CDK7) inhibitor or a pharmaceutical composition thereof, results in one or more a reduction in tumor volume, a loss of PSA expression, increased necrosis, reduced proliferative activity, increased apoptosis, a reduction in p-MED1 levels in a tumor, reduced plasma PSA expression.

7. The method for treating an AR-dependent cancer according to claim 1, wherein the composition is formulated for oral administration or is formulated for intravenous injection.

* * * * *